(12) United States Patent
Schreiter et al.

(10) Patent No.: US 12,072,340 B2
(45) Date of Patent: Aug. 27, 2024

(54) REVERSIBLY SWITCHABLE FLUORESCENT PROTEIN-BASED INDICATORS

(71) Applicant: HOWARD HUGHES MEDICAL INSTITUTE, Chevy Chase, MD (US)

(72) Inventors: Eric R. Schreiter, Leesburg, VA (US); Fern Sha, Lansdale, PA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 902 days.

(21) Appl. No.: 17/040,856

(22) PCT Filed: Mar. 22, 2019

(86) PCT No.: PCT/US2019/023677
§ 371 (c)(1),
(2) Date: Sep. 23, 2020

(87) PCT Pub. No.: WO2019/183538
PCT Pub. Date: Sep. 26, 2019

(65) Prior Publication Data
US 2021/0215725 A1   Jul. 15, 2021

Related U.S. Application Data

(60) Provisional application No. 62/647,269, filed on Mar. 23, 2018.

(51) Int. Cl.
*G01N 33/84* (2006.01)
*G01N 21/17* (2006.01)
*G01N 21/64* (2006.01)

(52) U.S. Cl.
CPC ............. *G01N 33/84* (2013.01); *G01N 21/17* (2013.01); *G01N 21/64* (2013.01); *G01N 2021/6421* (2013.01)

(58) Field of Classification Search
None
See application file for complete search history.

(56) References Cited

U.S. PATENT DOCUMENTS 9,518,996 B2 * 12/2016 Schreiter ................ G01N 33/84

OTHER PUBLICATIONS

Fosque et al. 2015. Labeling of active neural circuits in vivo with designed calcium integrators. Science vol. 347, Issue 6223 (Year: 2015).*

* cited by examiner

*Primary Examiner* — Celine X Qian
*Assistant Examiner* — Tiffany Nicole Grooms
(74) *Attorney, Agent, or Firm* — Stites & Harbison, PLLC; Mandy Wilson Decker

(57) ABSTRACT

Reversibly switchable fluorescent protein-based indicators are disclosed, and can be used as neuronal activity markers. The disclosed reversibly switchable fluorescent protein-based indicators exhibit faster or slower photoswitching the presence or absence of calcium, and depending on the wavelength of light stimulus employed.

20 Claims, 11 Drawing Sheets
Specification includes a Sequence Listing.

REVERSIBLY SWITCHABLE FLUORESCENT PROTEIN-BASED INDICATORS

RELATED APPLICATIONS

This application claims priority from International Patent Application No. PCT/US19/23677 filed Mar. 22, 2019, which claims priority from U.S. Provisional Application Ser. No. 62/647,269 filed Mar. 23, 2018, the entire disclosure of which are incorporated herein by this reference.

TECHNICAL FIELD

The presently-disclosed subject matter relates to reversibly switchable fluorescent protein-based indicators. In particular, the presently-disclosed subject matter relates to reversibly switchable fluorescent protein-based indicators that can be used as neuronal activity markers, and which exhibit faster or slower photoswitching the presence or absence of calcium, and depending on the wavelength of light stimulus.

INTRODUCTION

Genetically encoded indicators of neuronal activity are useful for imaging and tracking the activity of neurons in the brain [1]. In particular, genetically encoded indicators based on photoconvertible fluorescent protein (FP) domains have enabled optical marking and selection of active neuron populations [2].

Neuronal activity markers based on photoconvertible FPs are permanent and irreversible, thus limiting their in vivo utility in samples where multiple snapshots of activity are desirable or where different activity profiles must be compared within the same sample. Accordingly, there remains a need for improved fluorescent protein-based indicators and markers of neuronal activity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned: likewise, those features can be applied to other embodiments of the presently-disclosed subject matter, whether listed in this Summary or not. To avoid excessive repetition, this Summary does not list or suggest all possible combinations of such features.

The presently-disclosed subject matter relates to reversibly switchable fluorescent protein-based indicators, and includes isolated polypeptides that are useful for detecting ions, small molecule analytes, and/or cellular states such as membrane potential (e.g., voltage). The presently-disclosed subject matter also includes polynucleotides encoding the presently-disclosed isolated polypeptides. Furthermore, the presently-disclosed subject matter includes methods of using the presently-disclosed isolated polypeptides to detect ions, small molecule analytes, and/or cellular states such as membrane potential. Further still, the presently-disclosed subject matter includes methods for making the presently-disclosed isolated polypeptides.

In some embodiments the isolated polypeptides comprise a reversibly switchable fluorescent polypeptide, a compound-binding polypeptide, and a polypeptide target of the compound-binding (or voltage-sensing) polypeptide (polypeptide target), as well as variants and/or fragments of any of the polypeptides.

With respect to the reversibly-switchable fluorescent polypeptides (rsFP), the they can include generally include fluorescent polypeptides that can be reversibly changed from dim to bright fluorescence by irradiating with different wavelengths of light.

With regard to the compound-binding polypeptides, these polypeptides can be selected from polypeptides that can selectively bind particular substances. The compound-binding polypeptides therefore permit the isolated polypeptide to bind to one or more particular substance. Isolated polypeptides with compound-binding polypeptides can therefore act as an integrator, and possibly also as a negative indicator, for the particular substance that the compound-binding polypeptide can bind to. Exemplary detecting substances that can be bound by compound-binding polypeptides include ions and small molecule analytes. Detecting substances can include substances that have significant roles in cellular pathways.

In some embodiments the compound-binding polypeptide includes a calmodulin (CaM) polypeptide, or variants and/or fragments thereof. CaM binds to calcium, and permits the isolated polypeptide to act as an integrator for calcium. In turn, calcium detection can be used to trace neurons, measure neuronal activity, or the like.

With regard to the polypeptide targets of the compound-binding polypeptide, these polypeptide target can interact selectively with a compound-binding polypeptide that is bound to a detecting substance. For instance, in an exemplary isolated polypeptide that comprises the compound-binding polypeptide CaM, the polypeptide target can be a M13 polypeptide, or a variant and/or fragment thereof. M13 can selectively interact with the calcium-bound form of CaM. Some embodiments also comprise variants and/or fragments of any polypeptide target. Accordingly, in some embodiments the isolated polypeptide comprises an rsEosFP polypeptide, a CaM polypeptide, and a M13 polypeptide, or variants and/or fragments thereof.

The isolated polypeptides of the presently-disclosed subject matter include a reversibly switchable fluorescent protein, calmodulin, and a calmodulin-binding polypeptide.

In some embodiments, the polypeptide includes an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the polypeptide includes an amino acid sequence as encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the polypeptide includes an amino acid sequence a sequence having 95% identity to a sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the polypeptide includes an amino acid sequence a sequence having 95% identity to a sequence as encoded by the nucleic acid sequences of SEQ ID NOS:

1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the polypeptide includes a fragment of an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58, wherein 1, 2, 3, 4, 5, 6, 7, 8, 9, or 10 amino acids are removed relative to the amino acid sequence.

In some embodiments, the polypeptide includes a fragment of an amino acid sequence as encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57, wherein 1, 2, 3, 4, 5, 6, 7, 8, 9, or 10 amino acids are removed relative to the amino acid sequence.

The presently-disclosed subject matter also includes isolated nucleic acids that encode the polypeptides as disclosed herein. The presently-disclosed subject matter also includes vectors that include the isolated nucleic acids.

In some embodiments, the nucleic acid includes a sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the nucleic acid includes a sequence selected from the sequences encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the nucleic acid includes a sequence having 95% identity to a sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the nucleic acid includes a sequence having 95% identity to a sequence selected from the sequences encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the nucleic acid includes a fragment of a sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides are removed relative to the nucleic acid sequence.

In some embodiments, the nucleic acid includes a fragment of a sequence selected from the sequences encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides are removed relative to the nucleic acid sequence.

The presently-disclosed subject matter also includes detection methods. In some embodiments, presently-disclosed subject matter includes a method of detecting calcium in a sample, which involves: providing a sample that includes cells: contacting the sample with a vector including an isolated nucleic acid as disclosed herein, or contacting the sample with a polypeptide as disclosed herein: exposing the sample to a light: and detecting the presence of calcium in the sample by observing photoswitching of emitted fluorescence and/or the speed of photoswitching of the emitted fluorescence upon exposure to the light.

In some embodiments of the method, the cells are neurons. In some embodiments, the contacting step comprises a transgenic delivery of the isolated polypeptide to the sample that comprises cells.

In some embodiments, the exposing step involves exposing the sample to the light for about 1 millisecond to about 10 minutes. In some embodiments, the light includes a wavelength of about 400 nm to about 500 nm.

In some embodiments, the light includes a combination of wavelengths. In some embodiments, the combination of wavelengths includes a first wavelength and a second wavelength. In some embodiments, the combination of wavelengths includes a first wavelength or calibrated mixture of multiple wavelengths and a second wavelength or calibrated mixture of multiple wavelengths. In some embodiments, the combination of wavelengths includes a first wavelength or calibrated mixture of multiple wavelengths directed in a donut shape with a second wavelength or calibrated mixture of multiple wavelengths directed in a center spot.

In some embodiments, of the method, the photoswitching is reversible. In some embodiments, the first wavelength or calibrated mixture of multiple wavelengths produces an observable photoswitching of emitted fluorescence and/or speed of photoswitching of the emitted fluorescence, and a second wavelength or calibrated mixture of multiple wavelengths resets the photoswitching to allow for repeated detection. In some embodiments in which the cells are neurons, the photoswitching of emitted fluorescence and/or speed of photoswitching of the emitted fluorescence upon exposure to the light is a function of intracellular calcium concentration and/or neuronal activity.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 3A includes fluoresence imaging from two wells of neurons during blue light illumination with or without field stimulation at 80 Hz to drive action potential firing. In cycles 1 and 3, only Well 2 was field stimulated. In cycle 2, only Well 1 was field stimulated. Both wells were reset following each cycle using violet light illumination. Arrows on time-course trace show timepoint of field stimulations. Merged green and red fluorescence images of a representative neuron from each well are shown at time=10 s for each cycle (top panels). Error bars are standard deviation, Well 1 n=8 and Well 2 n=7. FIG. 3B includes a time-course of rsCaMPARI spontaneous recovery in the dark at 37° ° C. following blue light illumination in the presence (previously stimulated) or absence (previously non-stimulated) of field stimulation. Arrows denote field stimulation between each imaging timepoint. Error bars are standard deviation, non-stimulated n=66 and stimulated n=59.

FIG. 4A includes green fluorescence images of rsCaMPARI in cultured rat hippocampal neurons before and after blue light illumination. A single cell, denoted by pipette drawing, is patched and stimulated during blue light illumination. FIG. 4B includes single-trial recording of action potentials from current injection in patched neuron shown in (FIG. 4A) using fluorescence imaging (solid green trace) or electrophysiology to measure membrane potential (black trace). Average fluorescent traces of non-patched neurons are shown as dashed green trace. Cycles 2 and 3 were recorded following a reset of rsCaMPARI by violet light. Each cycle includes three stim trials with each trial containing 22-25 spikes.

FIG. 5A includes merged green and red fluorescence images pre and post blue light illumination from three cycles. +ChrimsonR neurons labeled with JF635 dye are shown in bottom panels. FIG. 5B includes average green-to-red fluorescent traces of neurons that do or do not co-express channelrhodopsin. Note that ChrimsonR is activated by both the excitation light for rsCaMPARI and mRuby3 and a significant decrease in rsCaMPARI fluorescence is already observed in the first image for +ChrimsonR neurons. Error bars are standard deviation, +ChrimsonR n=42 and −ChrimsonR n=79. FIG. 5C includes relative red-to-green fluorescence ratios of +ChrimsonR and −ChrimsonR neurons. Error bars are standard deviation, asterisks denote a significant difference between post-illumination images of +ChrimsonR and −ChrimsonR neurons (**** P<0.0001, two-tailed Student's t-test).

BRIEF DESCRIPTION OF THE SEQUENCE LISTING

Figure 1:
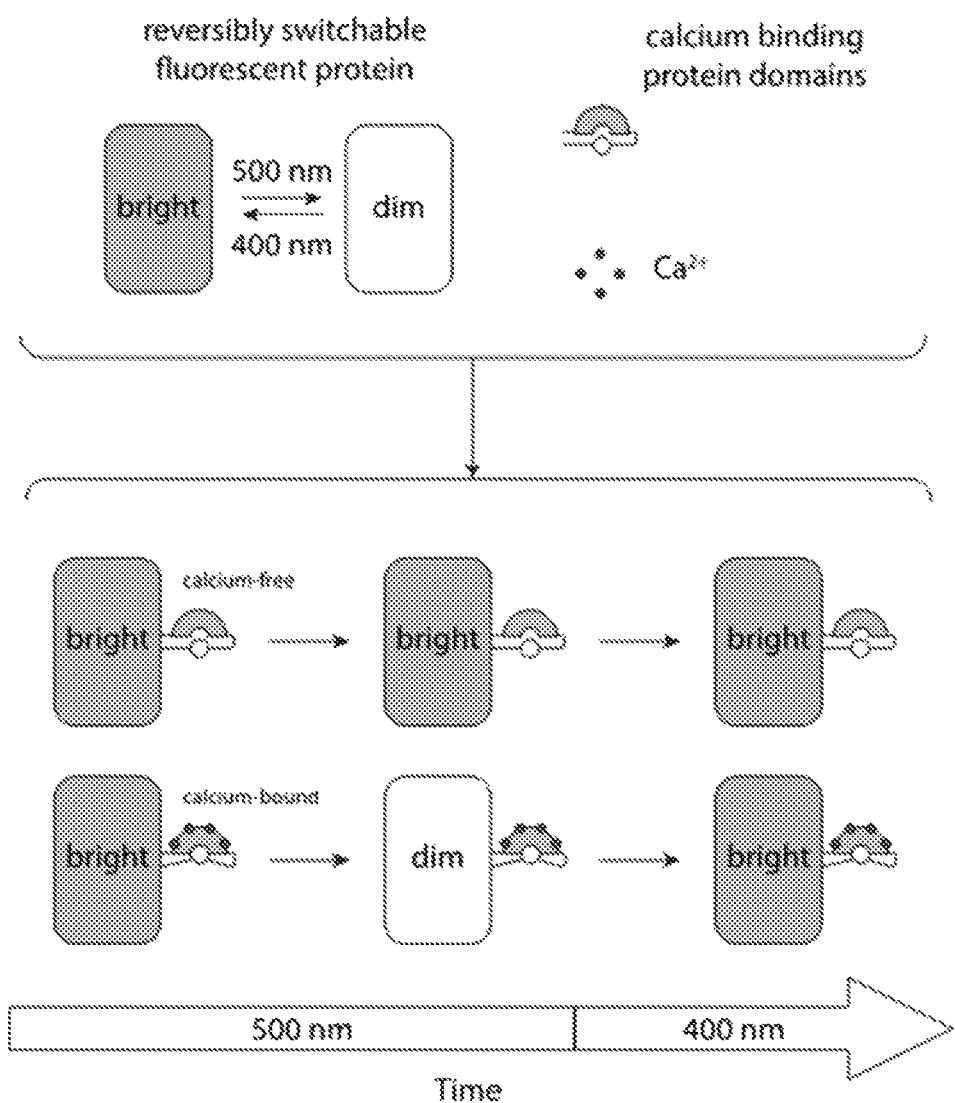
FIG. 1 is a schematic representation of the reversibly switchable activity marker described.

SEQ ID NO: 1 is the nucleotide sequence encoding an exemplary rsCaMPARI, identified herein as rsCaMPARI-03;

SEQ ID NO: 2 is the amino acid for an exemplary rsCaMPARI, identified herein as rsCaMPARI-03;

SEQ ID NO 3: is the nucleotide sequence encoding an exemplary rsCaMPARI, identified herein as rsCaMPARI-17;

SEQ ID NO 4: is the amino acid for an exemplary rsCaMPARI, identified herein as rsCaMPARI-17;

SEQ ID NO 5: is the nucleotide sequence encoding an exemplary rsCaMPARI, identified herein as rsCaMPARI-24;

SEQ ID NO: 6 is the amino acid for an exemplary rsCaMPARI, identified herein as rsCaMPARI-24;

SEQ ID NO: 7 is the nucleotide sequence encoding an exemplary rsCaMPARI, identified herein as rsCaMPARI-25;

SEQ ID NO: 8 is the amino acid for an exemplary rsCaMPARI, identified herein as rsCaMPARI-25:

SEQ ID NO: 9 is the nucleotide sequence encoding an exemplary rsCaMPARI, identified herein as rsCaMPARI-26;

SEQ ID NO: 10 is the amino acid for an exemplary rsCaMPARI, identified herein as rsCaMPARI-26;

SEQ ID NO: 11 is the nucleotide sequence encoding an exemplary rsCaMPARI, identified herein as rsCaMPARI-27;

SEQ ID NO: 12 is the amino acid for an exemplary rsCaMPARI, identified herein as rsCaMPARI-27;

SEQ ID NO: 13 is the nucleotide sequence encoding an exemplary rsCaMPARI, identified herein as rsCaMPARI-29;

SEQ ID NO: 14 is the amino acid for an exemplary rsCaMPARI, identified herein as rsCaMPARI-29;

SEQ ID NO: 15 is the nucleotide sequence encoding an exemplary rsCaMPARI, identified herein as rsCaMPARI-30;

SEQ ID NO: 16 is the amino acid for an exemplary rsCaMPARI, identified herein as rsCaMPARI-30;

SEQ ID NO: 17 is the nucleotide sequence encoding an exemplary rsCaMPARI, identified herein as rsCaMPARI-33;

SEQ ID NO: 18 is the amino acid for an exemplary rsCaMPARI, identified herein as rsCaMPARI-33;

SEQ ID NO: 19 is the nucleotide sequence encoding an exemplary rsCaMPARI, identified herein as rsCaMPARI-44;

SEQ ID NO: 20 is the amino acid for an exemplary rsCaMPARI, identified herein as rsCaMPARI-44;

SEQ ID NO: 21 is the nucleotide sequence encoding an exemplary rsCaMPARI, identified herein as rsCaMPARI-45:

SEQ ID NO: 22 is the amino acid for an exemplary rsCaMPARI, identified herein as rsCaMPARI-45;

SEQ ID NO: 23 is the nucleotide sequence encoding an exemplary rsCaMPARI, identified herein as rsCaMPARI-46;

SEQ ID NO: 24 is the amino acid for an exemplary rsCaMPARI, identified herein as rsCaMPARI-46;

SEQ ID NO: 25 is the nucleotide sequence encoding an exemplary rsCaMPARI, identified herein as rsCaMPARI-53;

SEQ ID NO: 26 is the amino acid for an exemplary rsCaMPARI, identified herein as rsCaMPARI-53;

SEQ ID NO: 27 is the nucleotide sequence encoding an exemplary rsCaMPARI, identified herein as rsCaMPARI-54;

SEQ ID NO: 28 is the amino acid for an exemplary rsCaMPARI, identified herein as rsCaMPARI-54;

SEQ ID NO: 29 is the nucleotide sequence encoding an exemplary rsCaMPARI, identified herein as rsCaMPARI-61;

SEQ ID NO: 30 is the amino acid for an exemplary rsCaMPARI, identified herein as rsCaMPARI-61;

SEQ ID NO: 31 is the nucleotide sequence encoding an exemplary rsCaMPARI, identified herein as rsCaMPARI-65;

SEQ ID NO: 32 is the amino acid for an exemplary rsCaMPARI, identified herein as rsCaMPARI-65;

SEQ ID NO: 33 is the nucleotide sequence encoding an exemplary rsCaMPARI, identified herein as rsCaMPARI-67;

SEQ ID NO: 34 is the amino acid for an exemplary rsCaMPARI, identified herein as rsCaMPARI-67;

SEQ ID NO: 35 is the nucleotide sequence encoding an exemplary rsCaMPARI, identified herein as rsCaMPARI-78;

SEQ ID NO: 36 is the amino acid for an exemplary rsCaMPARI, identified herein as rsCaMPARI-78;

SEQ ID NO: 37 is the nucleotide sequence encoding an exemplary rsCaMPARI, identified herein as rsCaMPARI-79;

SEQ ID NO: 38 is the amino acid for an exemplary rsCaMPARI, identified herein as rsCaMPARI-79;

SEQ ID NO: 39 is the nucleotide sequence encoding an exemplary rsCaMPARI, identified herein as rsCaMPARI-46v2;

SEQ ID NO: 40 is the amino acid for an exemplary rsCaMPARI, identified herein as rsCaMPARI-46v2.

SEQ ID NO: 41 is the nucleotide sequence encoding an exemplary rsCaMPARI, identified herein as rsCaMPARI-46v3.

SEQ ID NO: 42 is the amino acid for an exemplary rsCaMPARI, identified herein as rsCaMPARI-46v3.

SEQ ID NO: 43 is the nucleotide sequence encoding an exemplary rsCaMPARI, identified herein as rsCaMPARI-46v4.

SEQ ID NO: 44 is the amino acid for an exemplary rsCaMPARI, identified herein as rsCaMPARI-46v4.

SEQ ID NO: 45 is the nucleotide sequence encoding an exemplary rsCaMPARI, identified herein as rsCaMPARI-46v5.

SEQ ID NO: 46 is the amino acid for an exemplary rsCaMPARI, identified herein as rsCaMPARI-46v5.

SEQ ID NO: 47 is the nucleotide sequence encoding an exemplary rsCaMPARI, identified herein as rsCaMPARI-46v6.

SEQ ID NO: 48 is the amino acid for an exemplary rsCaMPARI, identified herein as rsCaMPARI-46v6.

SEQ ID NO: 49 is the nucleotide sequence encoding an exemplary rsCaMPARI, identified herein as rsCaMPARI-46v7.

SEQ ID NO: 50 is the amino acid for an exemplary rsCaMPARI, identified herein as rsCaMPARI-46v7.

SEQ ID NO: 51 is the nucleotide sequence encoding an exemplary rsCaMPARI, identified herein as rsCaMPARI-46v8.

SEQ ID NO: 52 is the amino acid for an exemplary rsCaMPARI, identified herein as rsCaMPARI-46v8.

SEQ ID NO: 53 is the nucleotide sequence encoding an exemplary rsCaMPARI, identified herein as rsCaMPARI-46v9.

SEQ ID NO: 54 is the amino acid for an exemplary rsCaMPARI, identified herein as rsCaMPARI-46v9.

SEQ ID NO: 55 is the nucleotide sequence encoding an exemplary rsCaMPARI, identified herein as rsCaMPARI-46v10.

SEQ ID NO: 56 is the amino acid for an exemplary rsCaMPARI, identified herein as rsCaMPARI-46v10.

SEQ ID NO: 57 is the nucleotide sequence encoding an exemplary rsCaMPARI, identified herein as rsCaMPARI-46v11.

SEQ ID NO: 58 is the amino acid for an exemplary rsCaMPARI, identified herein as rsCaMPARI-46v11.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to reversibly switchable fluorescent protein-based indicators, and includes isolated polypeptides that are useful for detecting ions, small molecule analytes, and/or cellular states such as membrane potential (e.g., voltage). The presently-disclosed subject matter also includes polynucleotides (e.g., cDNA) encoding the presently-disclosed isolated polypeptides. Furthermore, the presently-disclosed subject matter includes methods of using the presently-disclosed isolated polypeptides to detect ions, small molecule analytes, and/or cellular states such as membrane potential. Further still, the presently-disclosed subject matter includes methods for making the presently-disclosed isolated polypeptides.

The term "isolated", when used in the context of an isolated nucleotide or an isolated polypeptide, is a nucleotide or polypeptide that, by the hand of man, exists apart from its native environment and is therefore not a product of nature. An isolated nucleotide or polypeptide can exist in a purified form or can exist in a non-native environment such as, for example, in a transgenic host cell. The term "native" or "wild type" refers to a gene that is naturally present in the genome of an untransformed cell. Similarly, when used in the context of a polypeptide, "native" or "wild type" refers to a polypeptide that is encoded by a native gene of an untransformed cell's genome.

Additionally, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing. The term "fusion polypeptide" and the like refer to a polypeptide that is comprised of two or more distinct polypeptides that are covalently bound.

In some embodiments the isolated polypeptides comprise a reversibly switchable fluorescent polypeptide, a compound-binding polypeptide, and a polypeptide target of the compound-binding (or voltage-sensing) polypeptide (polypeptide target), as well as variants and/or fragments of any of the polypeptides. The individual polypeptides that comprise the isolated polypeptide can be arranged in any fashion. For instance, some embodiments of isolated polypeptide can comprise, from the N-terminus to C-terminus, the compound-binding polypeptide, the fluorescent polypeptide, and the polypeptide target. In other embodiments the isolated polypeptide can comprise, from the C-terminus to N-terminus, the compound-binding polypeptide, the fluorescent polypeptide, and the polypeptide target. In this regard, even if not specifically set forth herein, embodiments of the presently-disclosed polypeptides include fusion polypeptides.

The term "variant" refers to an amino acid sequence that is different from the reference polypeptide sequence by the location or type of one or more amino acids. Thus, a variant may include one or more amino acid substitutions. The terms "polypeptide fragment" or "fragment", when used in reference to a reference polypeptide, refer to a polypeptide in which amino acid residues are deleted as compared to the reference (e.g., native) polypeptide itself, but where the remaining amino acid sequence is usually identical to the corresponding positions in the reference polypeptide. As mentioned above, in some instances such deletions can occur at the amino-terminus, carboxy-terminus of the reference polypeptide, or alternatively both.

A fragment can also be a "functional fragment," in which case the fragment retains some or all of the activity of the reference polypeptide as described herein. For instance, a functional fragment of a fluorescent polypeptide can retain some or all of its fluorescent properties, and in some instances the fluorescent properties can be enhanced relative to the reference (e.g., native) fluorescent polypeptide.

With respect to the reversibly-switchable fluorescent polypeptides (rsFP), the they can include generally include fluorescent polypeptides that can be reversibly changed from dim to bright fluorescence by irradiating with different wavelengths of light. In some embodiments the fluorescent polypeptides are selected from Dronpa, rsEGFP, or rsCherry. In some embodiments the rsFP is a reversibly switchable Eos fluorescent polypeptide (rsEosFP) or a fragment and/or variant thereof. In some embodiments the fluorescent polypeptide can be circularly permutated and/or comprise amino acid substitutions.

With regard to the compound-binding polypeptides, these polypeptides can be selected from polypeptides that can selectively bind particular substances. The compound-binding polypeptides therefore permit the isolated polypeptide to bind to one or more particular substance. Isolated polypeptides with compound-binding polypeptides can therefore act as an integrator, and possibly also as a negative indicator, for the particular substance that the compound-binding polypeptide can bind to. Exemplary detecting substances that can be bound by compound-binding polypeptides include ions and small molecule analytes. Detecting substances can include substances that have significant roles in cellular pathways.

In some embodiments the compound-binding polypeptide includes a calmodulin (CaM) polypeptide, or variants and/or fragments thereof. CaM binds to calcium, and permits the isolated polypeptide to act as an integrator for calcium. In turn, calcium detection can be used to trace neurons, measure neuronal activity, or the like.

With regard to the polypeptide targets of the compound-binding polypeptide, these polypeptide target can interact selectively with a compound-binding polypeptide that is bound to a detecting substance. For instance, in an exemplary isolated polypeptide that comprises the compound-binding polypeptide CaM, the polypeptide target can be a M13 polypeptide, or a variant and/or fragment thereof. M13 can selectively interact with the calcium-bound form of CaM. Some embodiments also comprise variants and/or fragments of any polypeptide target. Accordingly, in some embodiments the isolated polypeptide comprises an rsEosFP polypeptide, a CaM polypeptide, and a M13 polypeptide, or variants and/or fragments thereof. In some embodiments, a fragment is provided wherein 1, 2, 3, 4, 5, 6, 7, 8, 9, or 10 amino acids are removed relative to the full-length of the isolated polypeptide. For example, the amino acids could be removed from one or both of the ends of the isolated polypeptide, the reversibly switchable fluorescent polypeptide, the compound-binding polypeptide, and/or the polypeptide target of the compound-binding polypeptide.

In some embodiments, the isolated polypeptide includes a polypeptide having an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the isolated polypeptide includes a polypeptide having 85, 86, 87, 88, 89, 90, 91, 92, 93, 94, 95, 96, 97, 98, or 99% identity to an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

In some embodiments, the isolated polypeptide includes a variant wherein 1, 2, 3, 4, 5, 6, 7, 8, 9, or 10 amino acids are removed relative to the polypeptide having an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58. For example, in some embodiments, the amino acids could be removed from one or both ends of the amino acid sequence.

In some embodiments, the isolated polypeptide includes a polypeptide having an amino acid sequence selected from the group of amino acid sequences encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the isolated polypeptide includes a polypeptide having 85, 86, 87, 88, 89, 90, 91, 92, 93, 94, 95, 96, 97, 98, or 99% identity to an amino acid sequence selected from the group of amino acid sequences encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments, the isolated polypeptide includes a variant wherein 1, 2, 3, 4, 5, 6, 7, 8, 9, or 10 amino acids are removed relative to the polypeptide having an amino acid sequence selected from the group of amino acid sequences encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57. For example, in some embodiments, the amino acids could be removed from one or both ends of the amino acid sequence.

"Percent similarity" and "percent homology" are synonymous as herein and can be determined, for example, by comparing sequence information using the GAP computer program, available from the University of Wisconsin Geneticist Computer Group. The GAP program utilizes the alignment method of Needleman et al. (1970) *J. Mol. Biol.* 48:443, as revised by Smith et al. (1981) *Adv. Appl. Math.* 2:482. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap: and (3) no penalty for end gaps. The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

In some embodiments the isolated polypeptides can comprise one or more linker polypeptides that are disposed between any of the individual polypeptides (e.g., fluorescent polypeptide, compounding binding polypeptide, polypeptide target polypeptide, etc.) that are included in the isolated polypeptide. In some embodiments the isolated polypeptides comprise a first polypeptide linker disposed between the compound-binding polypeptide and the fluorescent polypeptide. Additionally or alternatively, some embodiments comprise a second linker polypeptide disposed between the fluorescent polypeptide and the polypeptide target. The linker polypeptides can be provided for the purpose of purifying the isolated polypeptide, among other things. For instance, in some embodiments at least one of the linker polypeptides is a hexahistidine tag (6×His tag) that can be used to purify the protein using affinity chromatography. In some embodiments at least one linker can be a restriction site used in the assembly of DNA, such as XhoI or MluI. Those of ordinary skill will appreciate other linker polypeptides that can be incorporated into the isolated polypeptides for purification purposes, as restriction sites, or the like.

The present isolated polypeptides can also comprise a nuclear export signal (NES). The NES can signal for export of the isolated protein from the cell nucleus. Consequently, the addition of a NES can, among other things, allow the isolated polypeptide to detect substances outside the cell nucleus. The NES may be located at the N-terminus or the C-terminus of the isolated polypeptide.

The presently-disclosed subject matter also includes nucleic acid molecules (e.g., cDNA) that encode an isolated polypeptide.

In some embodiments the isolated nucleic acid includes comprising a sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments the isolated nucleic acid includes comprising a sequence having 85, 86, 87, 88, 89, 90, 91, 92, 93, 94, 95, 96, 97, 98, or 99% identity to the sequences selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

In some embodiments the isolated nucleic acid includes a variant wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides are removed relative to the nucleic acid sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57. For example, in some embodiments, the nucleotides could be removed from one or both ends of the nucleic acid sequence.

In some embodiments the isolated nucleic acid includes comprising a sequence selected from the sequences encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58;

In some embodiments the isolated nucleic acid includes comprising a sequence having 85, 86, 87, 88, 89, 90, 91, 92, 93, 94, 95, 96, 97, 98, or 99% identity to the sequence encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58;

In some embodiments the isolated nucleic acid includes a variant wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides are removed relative to the nucleic acid sequence selected from the sequences encoding a polypeptide having an amino acid selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58: For example, in some embodiments, the nucleotides could be removed from one or both ends of the nucleic acid sequence.

The terms "nucleotide," "polynucleotide," "nucleic acid," "nucleic acid sequence," and the like refer to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98). The terms are inclusive of cDNA molecules.

In some embodiments the nucleic acid molecule is a molecule that encodes portions of an isolated polypeptide, including any of the portions described herein. For instance, the nucleic acid molecule may encode for a compound-binding polypeptide (e.g., CaM), a reversibly switchable fluorescent polypeptide (e.g., rsEosFP), and/or a polypeptide target (e.g., M13). Other embodiments of nucleic acid molecules can encode for the first polypeptide linker, the second polypeptide linker, the inter-domain linker, the NES, or any combination thereof of any of the isolated polypeptides described herein.

Further still, the presently-disclosed subject matter includes a method of detecting an ion and/or small molecule analyte (collectively referred to herein as "detecting substance") in a sample. Exemplary detecting substances include, but are not limited to, calcium, glutamate, gamma-aminobutyric acid, glycine, acetylcholine, dopamine, other neurotransmitters and neuromodulators, ATP, ADP, CAMP, cGMP, sugars such as glucose, inositol phosphates such as IP3, diacylglycerol, other metabolites and signaling molecules, zinc, iron, potassium, magnesium, other ions, proteins, and combinations thereof. Additionally or alternatively, some methods of the presently-disclosed subject matter include methods of detecting a cellular state. Exemplary cellular states that can be detected include, but are not limited to, membrane potential, kinase activity, G-protein coupled receptor (GPCR) activation, ion channel activity, transporter activity, and combinations thereof.

In some embodiments the method comprises providing a sample that includes cells, contacting the sample with an embodiment of the present isolated polypeptides, exposing the sample that has contacted the isolated polypeptide to light, and then detecting the presence of the detecting substance. The term "sample" refers to a sample from the subject including a cell, for example, urine, serum, blood, plasma, saliva, sputum, feces, tear, hair, nails, and organ tissue, and other samples including a cell from the subject.

In some embodiments the cells that comprise the sample are brain cells. In some embodiments the samples include neuron cells. In this regard, the detecting substance can be calcium, which plays a role in neuronal signaling. Thus, the present methods can utilize the isolated polypeptides to label "active" cells during a particular stimulus, and quantify and characterize calcium activity in response to that stimulus. Similarly, the present methods can be used to trace neurons based on their calcium activity. Those of ordinary skill will appreciate further uses for detecting methods that utilize the present isolated polypeptides.

There are various ways that the isolated polypeptide can be made to contact a sample. In some embodiments the isolated polypeptide is injected directly or via a carrier to a particular site that includes the cells that are to be observed. In other embodiments the isolated polypeptide is transgenically delivered to cells that comprise a sample. The term "transgenic" and the like is used herein to refer to introducing particular genetic material into the genome of a cell or organism. Thus, cells that have had the gene for the isolated polypeptide for the isolated polypeptide transgenically delivered to the cells can express the isolated polypeptide themselves.

With regard to the exposing step, a sample may be exposed to any type of light and for any duration that induces a change in fluorescence of the isolated polypeptide. In color-changing photoconvertible polypeptides, exposure to light will induce a color shift in the polypeptides that can be dependent on the concentration of a detecting substance in the sample. The duration of time that a sample is exposed is not particularly limited. In some embodiments light is exposed for a time period sufficient to expose the cells within a particular volume of sample. In specific embodiments the light for exposing a sample can be emitted for a time period of about 1 millisecond, 1 second, 10 seconds, 20 seconds, 30 seconds, 40 seconds, 50 seconds, 60 seconds, 1 minute, 2 minutes, 3 minutes, 4 minutes, 5 minutes, 6 minutes, 7 minutes, 8 minutes, 9 minutes, or 10 minutes. In other embodiments the light for exposing a sample can be emitted for a time period of about 0.5 hours, 1 hour, 2 hours, 3 hours, 4 hours, 5 hours, or more.

The type of light that is used to expose a sample is generally only limited in that it should comprise a wavelength that can stimulate a particular photoconversion, photoactivation, or the like. The term "light" refers to any electromagnetic radiation including, but not limited to, visible light, microwave light, ultraviolet light, or the like. The light can have a wavelength of about 400 nm to about 500 nm. The light may also have a wavelength falling either above or below these recited wavelengths so long as it can induce a photoconversion or photoactivation in the isolated polypeptide. In some embodiments of the method, the light includes a wavelength of about 350, 351, 352, 353, 354, 355, 356, 357, 358, 359, 360, 361, 362, 363, 364, 365, 366, 367, 368, 369, 370, 371, 372, 373, 374, 375, 376, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, and 550.

Once the sample with the isolated polypeptide has been exposed to light, one can detect the presence of a detecting substance in the sample. The presence of a detecting substance can be evidenced by photoswitching of emitted fluorescence and/or the speed of photoswitching of the emitted fluorescence upon exposure to the light. The presence of a detecting substance can also be evidenced by a change in the intensity of a fluorescence emitted and/or degree of a change in the speed of photoswitching, which can be indicative of the presence and/or concentration of a detecting substance in a sample.

The indicators disclosed herein are reversible. The photoswitching cycle provides a convenient method to erase the marker/indicator for repeated marking experiments.

In some exemplary embodiments, the presently-disclosed subject matter provides a method of detecting calcium in a sample, which involves: (a) contacting a sample including cells with the vector including an isolated nucleic acid as disclosed herein or an isolated polypeptide as disclosed herein: (b) exposing the sample to a light: (c) detecting the presence of calcium in the sample by observing photoswitching of emitted fluorescence and/or the speed of photoswitching of the emitted fluorescence upon exposure to the light.

In some embodiments the cells can be, for example, neurons. In this regard, the photoswitching of emitted fluorescence and/or the speed of photoswitching of the emitted fluorescence upon exposure to the light is a function of intracellular calcium concentration and/or neuronal activity.

In some embodiments, the contacting step of the method involves a transgenic delivery of the isolated polypeptide to the sample that comprises cells. In some embodiments, the exposing step of the method involves exposing the sample to the light for about 1 millisecond to about 10 minutes.

In some embodiments of the method, the light includes a combination of wavelengths. In some embodiments, the combination includes one or more wavelengths. In some embodiments, the combination includes one or more calibrated mixtures of multiple wavelengths. In some embodiments, the combination includes a first wavelength and a second wavelength. In some embodiments, the combination includes a first wavelength or calibrated mixture of multiple wavelengths and a second wavelength or calibrated mixture of multiple wavelengths. In some embodiments, the combination includes a first wavelength or calibrated mixture of multiple wavelengths directed in a donut shape with a second wavelength or calibrated mixture of multiple wavelengths directed in a center spot.

In some embodiments of the method, a first wavelength or calibrated mixture of multiple wavelengths produces an observable photoswitching of emitted fluorescence and/or the speed of photoswitching of the emitted fluorescence, and a second wavelength or calibrated mixture of multiple wavelengths resets the photoswitching to allow for repeated detection.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

A set of reversibly switchable fluorescent protein-based indicators were developed, with a view toward overcoming shortcomings of known indicators and markers, including photoconvertible FPs that are permanent and irreversible. The indicators disclosed herein are reversible.

Consideration was given to reversibly switchable fluorescent proteins (rsFP), which typically photoswitch between a bright and dim state depending on the wavelength of light stimulus.[3] A disclosed herein, in the context of the presently-disclosed subject matter, rsFP photoswitching kinetics can be modulated by the insertion of calcium binding domains to function as an activity marker (FIG. 1). The photoswitching cycle provides a convenient method to erase the marker for repeated marking experiments.

Figure 2A:
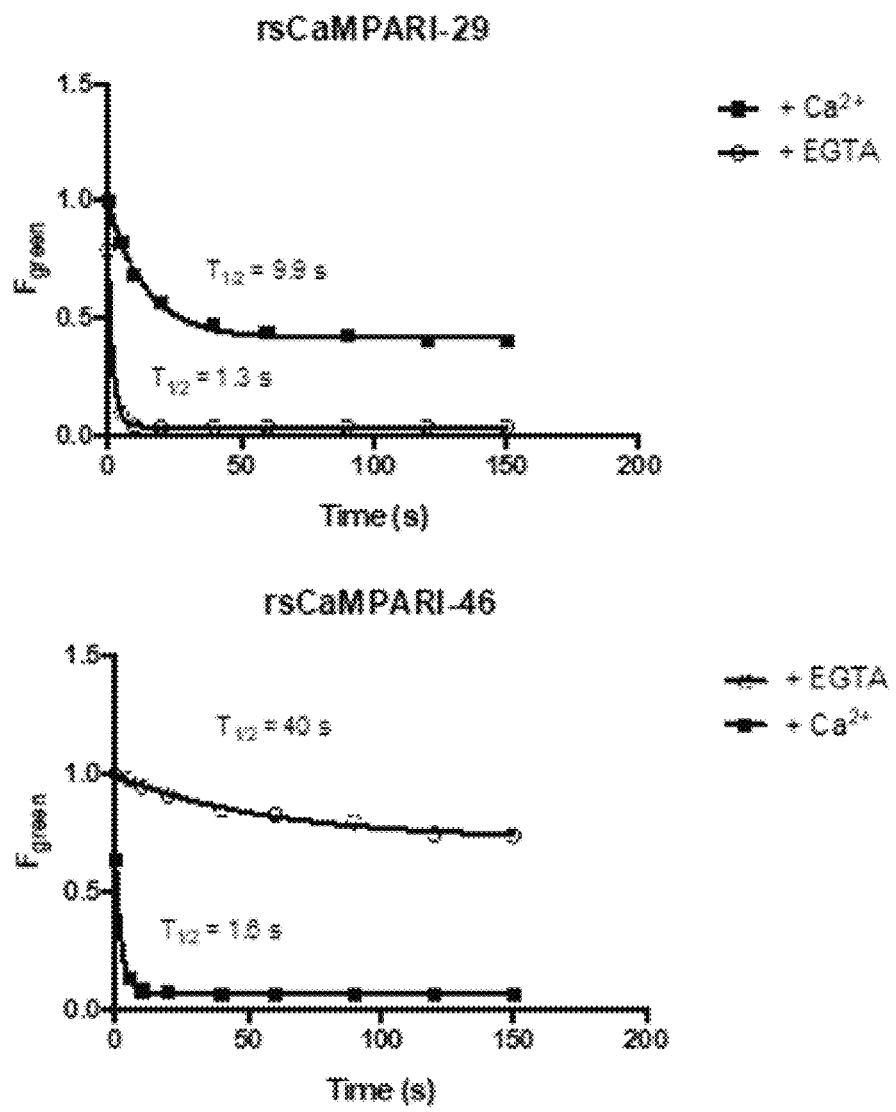
FIG. 2 includes an in vitro time-course measurements of photoswitching for two representative rsCaMPARI variants in presence or absence of calcium under different light conditions. Calcium binding resulted in faster or slower downswitching for rsCaMPARI-29 and rsCaMPARI-46, respectively, under both (A) 470 nm and (B) 490 nm light conditions. (C) 405 nm light rapidly upswitches rsCaMPARIs back to the bright state.
Figure 2B:
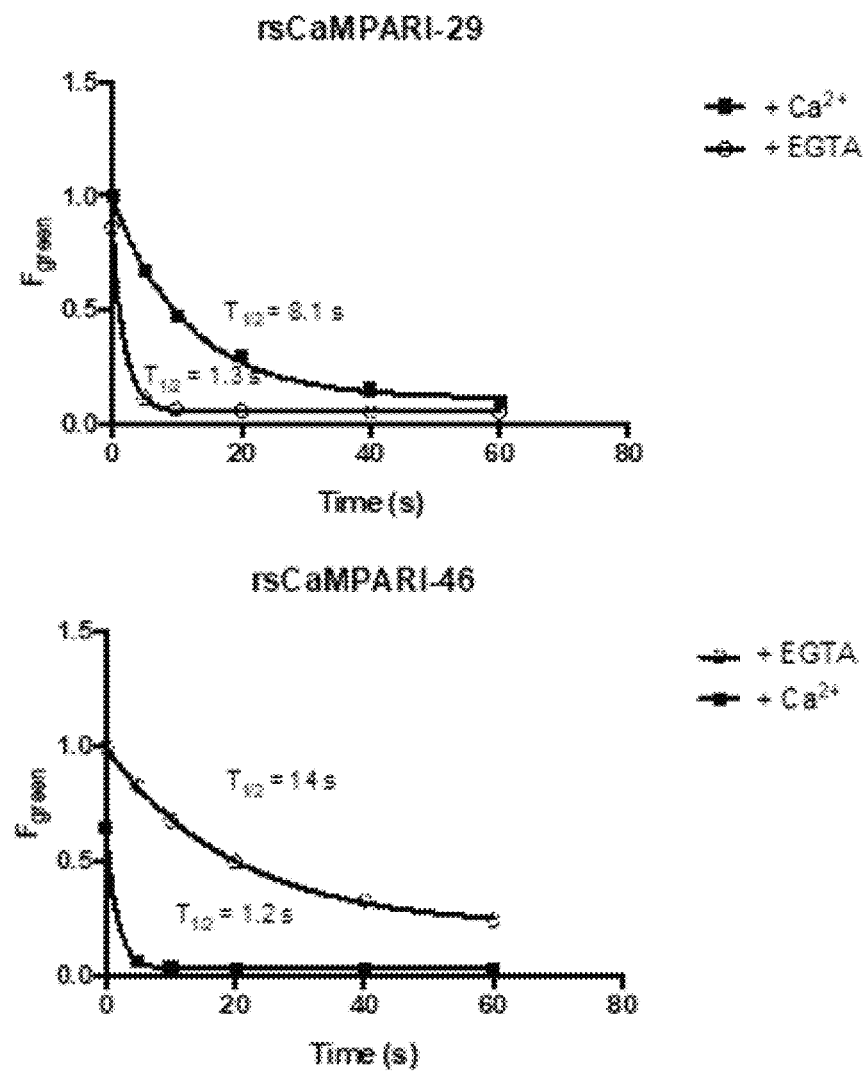
Figure 2C:
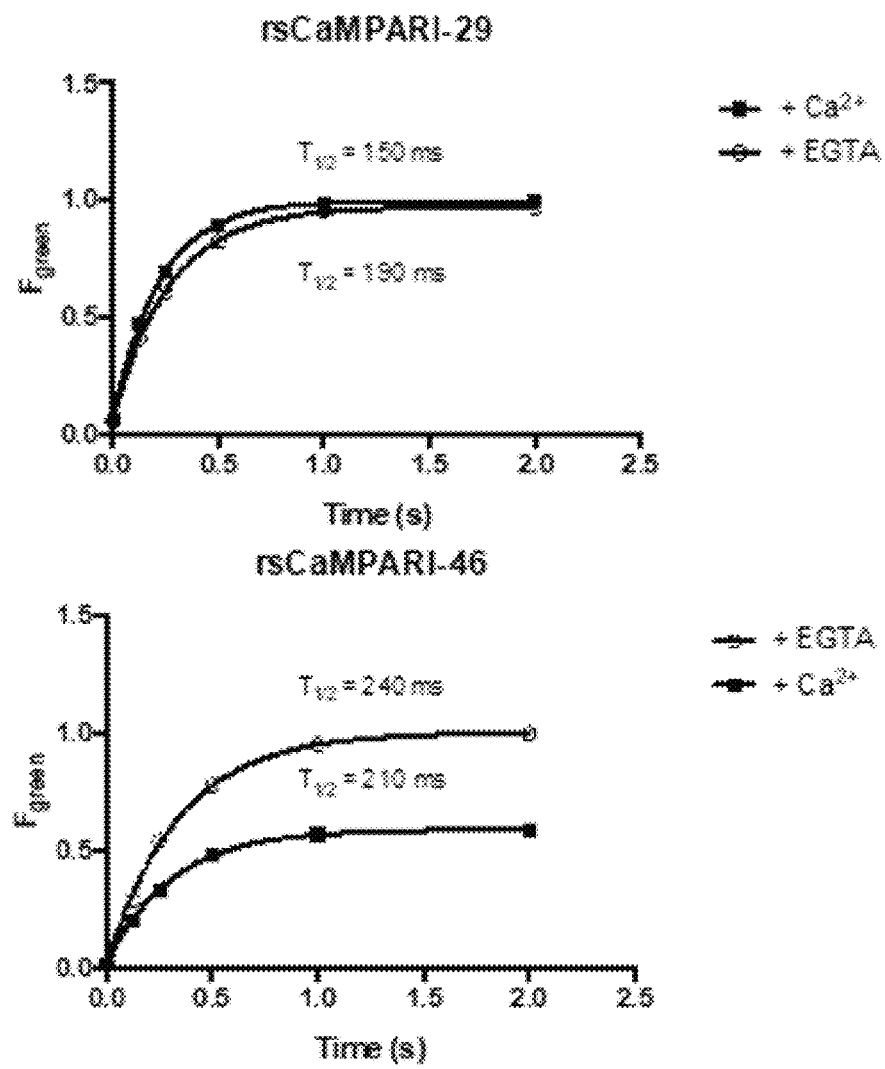

Indicators as disclosed herein, and referred to herein as rsCaMPARIs, were developed by inserting the calcium binding protein calmodulin and a calmodulin-binding peptide into the coding sequence of a reversibly switchable mutant of the fluorescent protein EosFP [4]. From purified protein measurements, two main types of variants were identified, which exhibit either faster or slower photoswitching in the presence of calcium than without (FIG. 2). Kinetic properties of exemplary variants are summarized in Table 1.

Figure 3A:
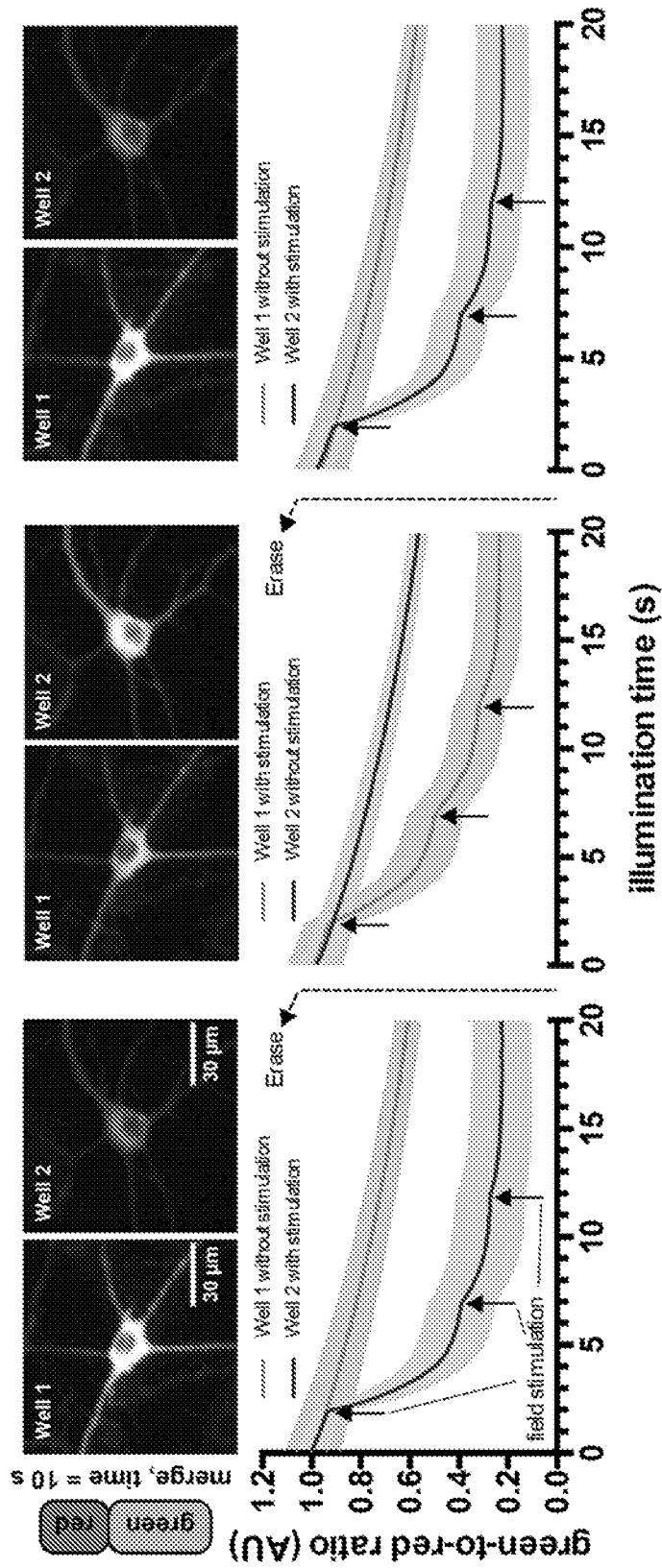
FIGS. 3A and 3B includes a characterization of rsCaMPARI-46-mRuby3 in cultured rat hippocampal neurons stimulated by a field electrode.
Figure 3B:
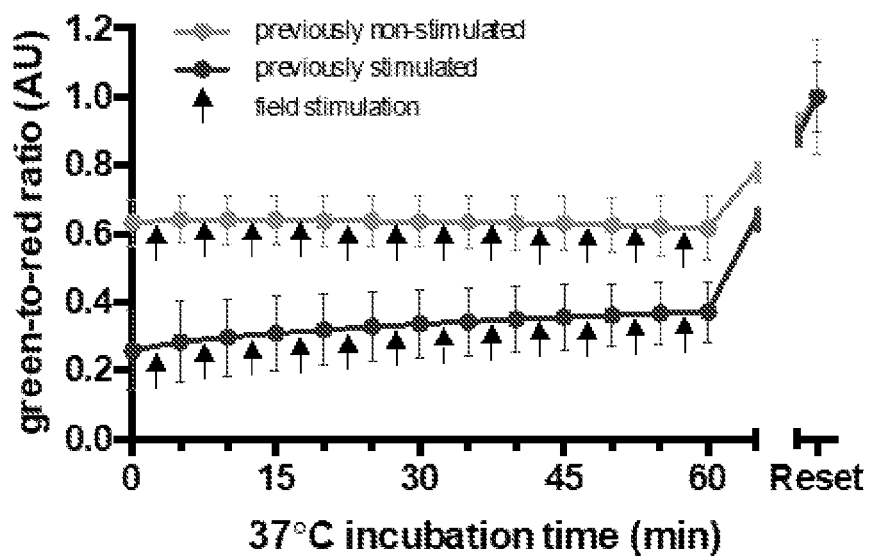
Figure 3C:
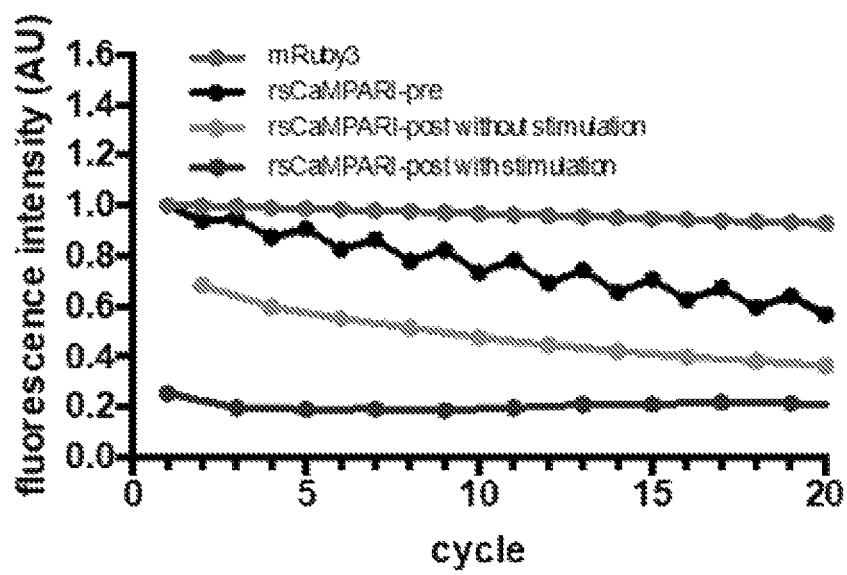
FIG. 3C shows photobleaching of rsCaMPARI-46-mRuby 3 over successive cycles of blue light illumination with or without field stimulation, followed by violet light illumination.

In one example, the variant rsCaMPARI-46 was fused to the red fluorescent protein mRuby3 and expressed in cultured rat hippocampal neurons (See FIG. 3A, top). Stimulation using a field electrode concurrent with blue light illumination (485 nm, ~200 mW/cm$^2$) caused periods of rapid downswitching of the rsCaMPARI green signal relative to the red signal, thereby marking the neuron, and could easily be reset by a violetlight for further rounds of stimulation and activity marking (See FIG. 3A, bottom). The fluorescent signal discriminating stimulated cells versus non-stimulated cells was relatively stable at 37° C. for periods up to one hour and remained stable even after field stimulations in the absence of blue light illumination (FIG. 3B). rsCaMPARI undergoes photobleaching during subsequent rounds of activity marking, but remains bright enough to discriminate active neurons for at least ten cycles (FIG. 3C).

Figure 4A:
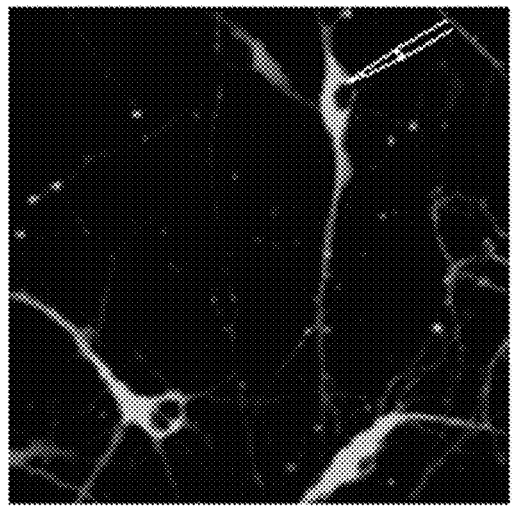
FIGS. 4A and 4B include characterization of rsCaMPARI in cultured rat hippocampal neurons stimulated by current injection via patch clamp.
Figure 4A:
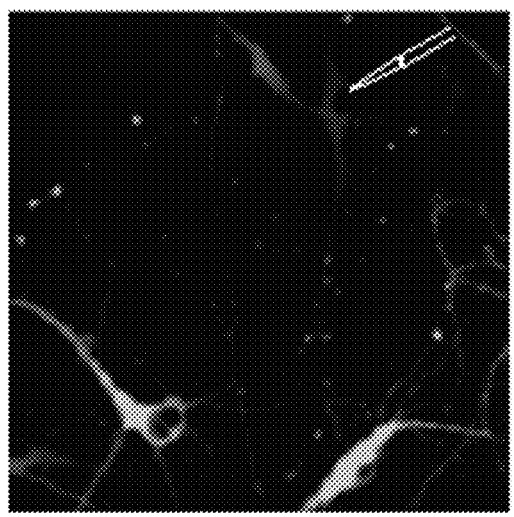
Figure 4B:
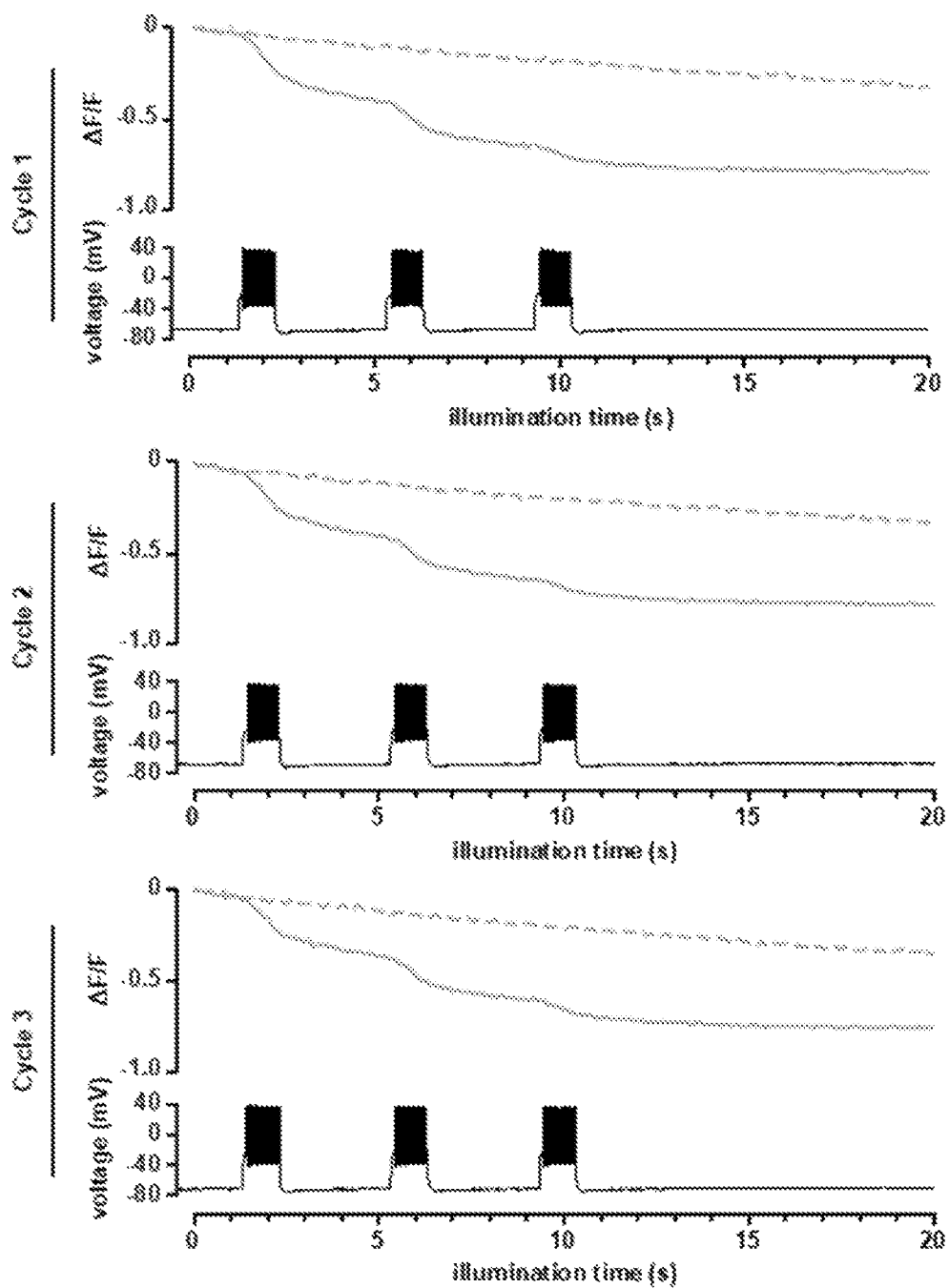
Figure 5A:
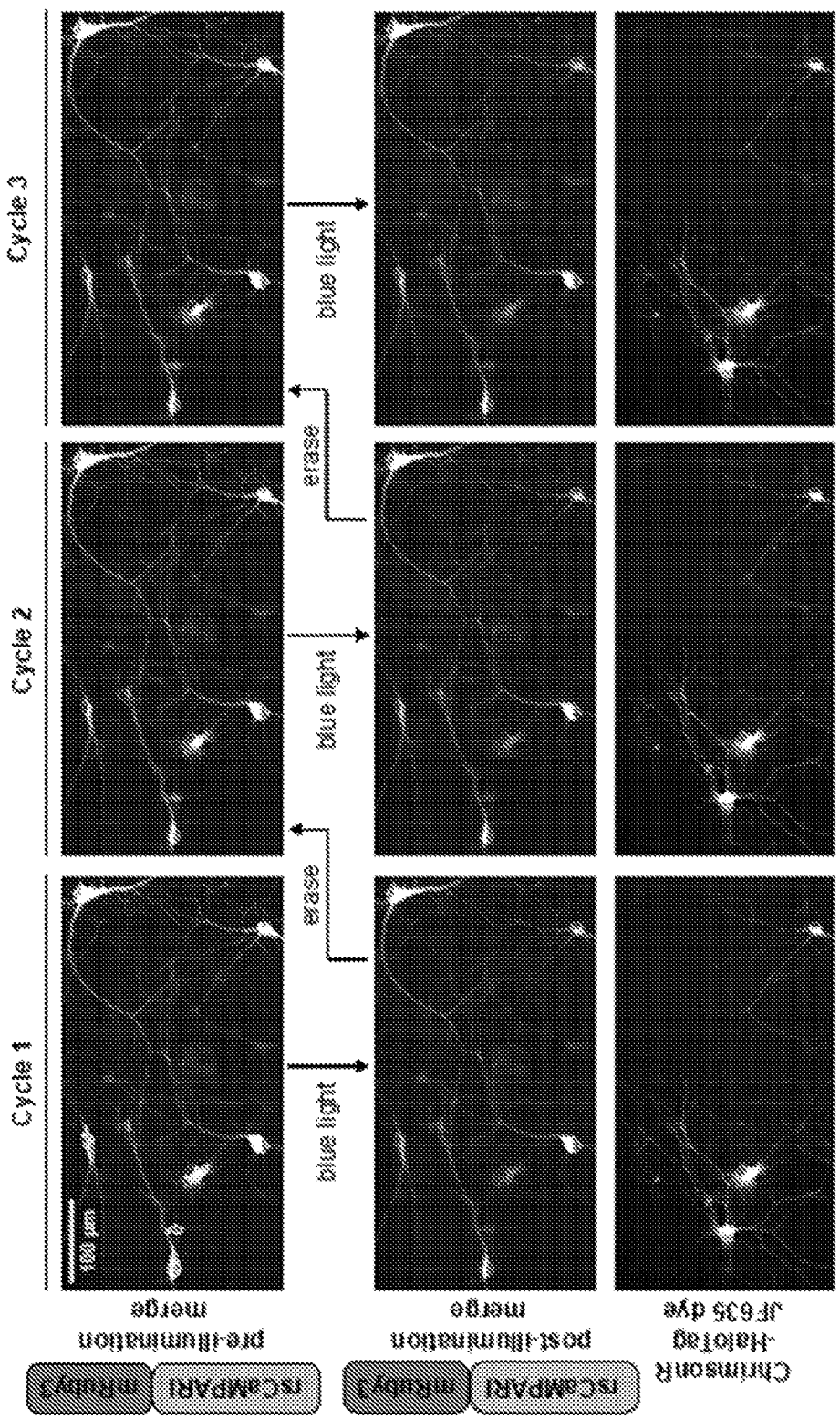
FIGS. 5A-5C include characterization of rsCaMPARI-46-mRuby3 in cultured rat hippocampal neurons with a subset co-expressing channelrhodopsin ChrimsonR-HaloTag.
Figure 5B:
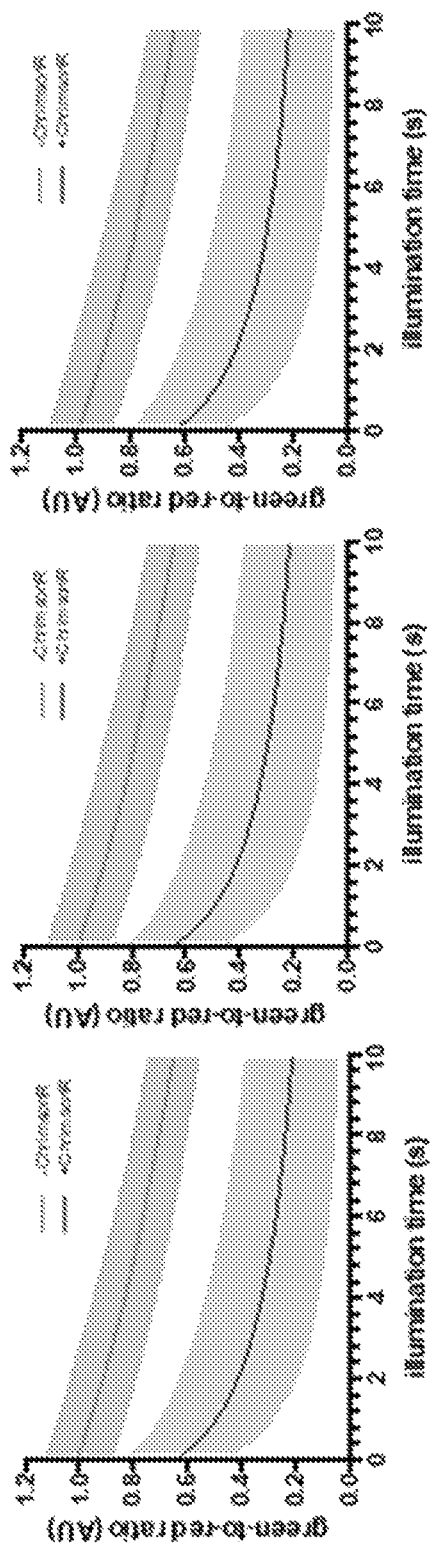
Figure 5C:
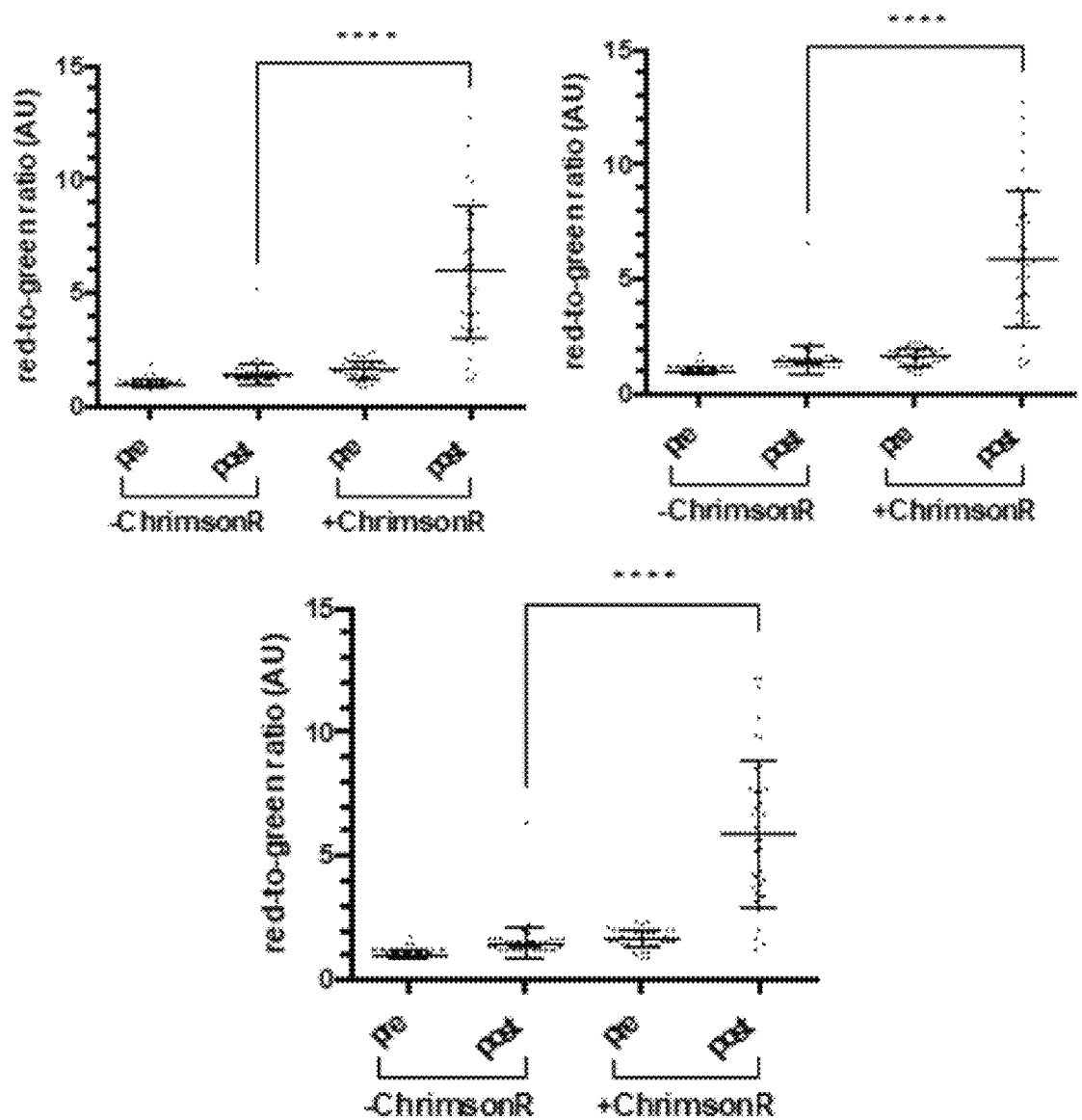

To demonstrate the utility of rsCaMPARI to mark active subsets of neurons in a field of view; we used two approaches. In the first approach, we expressed rsCaMPARI-46 in cultured rat hippocampal neurons and patched a single neuron in a field of view for current injection (FIG. 4A). Current injection and concurrent blue light illumination resulted in more rapid loss of fluorescence of the patched neuron relative to surrounding neurons and the patched neuron could be selectively photoswitched over multiple cycles of violet and blue light illumination (FIG. 4B). In the second approach, we expressed rsCaMPARI-46-mRuby3 in cultured rat hippocampal neurons and co-expressed the channelrhodopsin ChrimsonR-HaloTag construct in a subset of the neurons for optogenetic access (FIG. 5A). Under blue light illumination, the subset of neurons co-expressing the channelrhodopsin undergo more rapid green signal loss relative to the red signal (FIG. 5B) and are marked relative to cells not expressing ChrimsonR (FIG. 5A, post-illumination merge panels). +ChrimsonR neurons in the post-illumination merge have significantly higher red-to-green ratios compared to −ChrimsonR neurons (FIG. 5C).

Exemplary embodiments of the indicators as disclosed herein include polypeptide sequences encoded by SEQ ID NOS: 1-57 or as set forth in SEQ ID NOS: 2-58.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lin, M. Z. and M. J. Schnitzer, *Genetically encoded indicators of neuronal activity*. Nat Neurosci, 2016. 19(9): p. 1142-53.
2. Fosque, B. F., et al., *Neural circuits. Labeling of active neural circuits in vivo with designed calcium integrators*. Science, 2015. 347(6223): p. 755-60.

3. Zhou, X. X. and M. Z. Lin, *Photoswitchable fluorescent proteins: ten years of colorful chemistry and exciting applications.* Curr Opin Chem Biol, 2013. 17(4): p. 682-90.
4. Chang, H., et al., *A unique series of reversibly switchable fluorescent proteins with beneficial properties for various applications.* Proc Natl Acad Sci USA, 2012. 109(12): p. 4455-60.
5. U.S. Pat. No. 9,518,996 to Schreiter, et al. for "Fluorescent Proetin-Based Indicators."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleic acid comprising a sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57, and the sequences encoding a polypeptide having an amino acid sequence selected from the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58; or a variant thereof having 95% identity thereto, or a fragment thereof wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides are removed relative to the nucleic acid sequence selected from the sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57.

2. The isolated nucleic acid of claim 1, comprising a sequence selected from the sequences of SEQ ID NOS: 1, 3, 5, 7, 9, 11, 13, 15, 17, 19, 21, 23, 25, 27, 29, 31, 33, 35, and 37, and the sequences encoding a polypeptide having an amino acid sequence selected from the amino acid sequences of SEQ ID NO: 2, 4, 6, 8, 10, 12, 14, 16, 18, 20, 22, 24, 26, 28, 30, 32, 34, 36, and 38.

3. The isolated nucleic acid of claim 1, comprising a sequence selected from the sequences of SEQ ID NOS: 39, 41, 43, 45, 47, 49, 51, 53, 55, and 57, and the sequences encoding a polypeptide having an amino acid sequence selected from the amino acid sequences of SEQ ID NO: 40, 42, 44, 46, 48, 50, 52, 54, 56, and 58.

4. A vector comprising the isolated nucleic acid of claim 1.

5. A method of detecting calcium in a sample, comprising:
providing a sample that comprises cells;
contacting the sample with
a vector including an isolated nucleic acid; or
the isolated polypeptide encoded by the isolated nucleic acid sequence;
wherein the isolated nucleic acid sequence is according to claim 1;
exposing the sample to a light; and
detecting the presence of calcium in the sample by observing photoswitching of emitted fluorescence and/or the speed of photoswitching of the emitted fluorescence upon exposure to the light.

6. The method of claim 5, wherein the cells are neurons.

7. The method of claim 5, wherein the contacting step comprises a transgenic delivery of the vector including the isolated nucleic acid.

8. The method of claim 5, wherein the exposing step comprises exposing the sample to the light for about 1 millisecond to about 10 minutes.

9. The method of claim 5, wherein the light comprises a wavelength of about 400 nm to about 500 nm.

10. The method of claim 5, wherein the light comprises a combination of wavelengths.

11. The method of claim 10, wherein the combination comprises a first wavelength and a second wavelength.

12. The method of claim 10, wherein the combination comprises a first wavelength or calibrated mixture of multiple wavelengths and a second wavelength or calibrated mixture of multiple wavelengths.

13. The method of claim 10, wherein the combination includes a first wavelength or calibrated mixture of multiple wavelengths directed in a donut shape with a second wavelength or calibrated mixture of multiple wavelengths directed in a center spot.

14. The method of claim 13, wherein the first wavelength or calibrated mixture of multiple wavelengths produces an observable photoswitching of emitted fluorescence and/or speed of photoswitching of the emitted fluorescence, and the second wavelength or calibrated mixture of multiple wavelengths resets the photoswitching to allow for repeated detection.

15. The method of claim 14, wherein the cells are neurons and the photoswitching of emitted fluorescence and/or speed of photoswitching of the emitted fluorescence upon exposure to the light is a function of intracellular calcium concentration and/or neuronal activity.

16. The method of claim 5, wherein a first wavelength or calibrated mixture of multiple wavelengths produces an observable photoswitching of emitted fluorescence and/or speed of photoswitching of the emitted fluorescence, and a second wavelength or calibrated mixture of multiple wavelengths resets the photoswitching to allow for repeated detection.

17. The method of claim 5, wherein the photoswitching is reversible.

18. An isolated polypeptide, comprising a polypeptide having an amino acid sequence selected from the group of amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58, and as encoded by the nucleic acid sequences of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, and 57; or a variant thereof having 95% identity thereto, or a fragment thereof wherein 1, 2, 3, 4, 5, 6, 7, 8, 9, or 10 amino acids are removed relative to the amino acid sequences of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, and 58.

19. The isolated polypeptide of claim 18, comprising a polypeptide having an amino acid sequence selected from the group of amino acid sequences of SEQ ID NO: 2, 4, 6, 8, 10, 12, 14, 16, 18, 20, 22, 24, 26, 28, 30, 32, 34, 36, and 38, and as encoded by the nucleic acid sequences of SEQ ID NOS: 1, 3, 5, 7, 9, 11, 13, 15, 17, 19, 21, 23, 25, 27, 29, 31, 33, 35, and 37.

20. The isolated polypeptide of claim 18, comprising a polypeptide having an amino acid sequence selected from the group of amino acid sequences of SEQ ID NO: 40, 42, 44, 46, 48, 50, 52, 54, 56, and 58, and as encoded by the nucleic acid sequences of SEQ ID NOS: 39, 41, 43, 45, 47, 49, 51, 53, 55, and 57.

* * * * *

SEQUENCE LISTING

<160> NUMBER OF SEQ ID NOS: 58

<210> SEQ ID NO 1
<211> LENGTH: 1227
<212> TYPE: DNA
<213> ORGANISM: Artificial Sequence
<220> FEATURE:
<223> OTHER INFORMATION: Synthetic

<400> SEQUENCE: 1

```
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg gaacgaagca tgactttcga agacggggc      300 atttgctatg ccagaagcga cataacaatg gaagggaca ctttctataa taaagttcga      360
ttttatggta ccaactttcc cgccaatggt ccagttatgc agaagaagac gctgaaatgg     420
gagccctcca ctgagaaaat gtatgtgcgt gatggagtgc tgacgggtgc gtactcaagc     480
cgccgcaagt tcaacaaaac cggccatgcc ttgcgtgcaa ttggccgcct gtccagcgga     540
ggctctggcg gttccggcgg ttcaggtgga tcagaccagc tgaccgagga gcaaattgca     600
gaatttaagg aggcgttctc tttgtttgac aaagatggcg acggtacaat tacaaccaag     660
gaattgggca cagtaatgcg ctcccttgga cagaatccca ctgaagccga acttcaagac     720
atgatcaatg aggttgatgc tgacggggat gggactatcg actttcctga gtttcttacc     780
atgatggctc gcaaaatgaa ggatacagac agtgaggagg aaattcgtga ggcctttcgt     840
gtgtttgata aggacgggaa cggttatatc tcagcggcgg agctgcgtca cgttatgacc     900
aacttaggcg aaaagctgac tgatgaagaa gtcgatgaga tgatccgcga ggcggacatc     960
gatggtgatg tcaagtcaa ttatgaagag tttgtggtga tgatgaccgc gaagaccaac    1020
gagatggctt tgttgcttga aggaaatgcc cattaccgat gtgacttcag aactacttac    1080
aaagctaagg agaagggtgt caagttacca ggcgtgcact atgtggacca caccattgag    1140
attttaagcc atgacaaaga ttacaacaag gttaagatct atgagtatgc tgttgctcat    1200
tctggattgc ctgacaatgc cagacga                                         1227
```

<210> SEQ ID NO 2
<211> LENGTH: 409
<212> TYPE: PRT
<213> ORGANISM: Artificial Sequence
<220> FEATURE:
<223> OTHER INFORMATION: Synthetic

<400> SEQUENCE: 2

```
Met Val Ser Ala Ile Lys Pro Asp Met Lys Ile Lys Leu Arg Met Glu
  1               5                  10                  15

Gly Asn Val Asn Gly His His Phe Val Ile Asp Gly Asp Gly Thr Gly
```

```
                    20                  25                  30
Lys Pro Tyr Glu Gly Lys Gln Thr Met Asp Leu Glu Val Lys Glu Gly
                35                  40                  45

Gly Pro Leu Pro Phe Ala Phe Asp Ile Leu Thr Thr Ala Phe Leu Tyr
     50                  55                  60

Gly Asn Arg Val Phe Val Lys Tyr Pro Asp Asn Ile Gln Asp Tyr Phe
 65                  70                  75                  80

Lys Gln Ser Phe Pro Lys Gly Tyr Ser Trp Glu Arg Ser Met Thr Phe
                 85                  90                  95

Glu Asp Gly Gly Ile Cys Tyr Ala Arg Ser Asp Ile Thr Met Glu Gly
                100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Thr Gly Ala Tyr Ser Ser
145                 150                 155                 160

Arg Arg Lys Phe Asn Lys Thr Gly His Ala Leu Arg Ala Ile Gly Arg
                165                 170                 175

Leu Ser Ser Gly Gly Ser Gly Gly Ser Gly Gly Ser Gly Gly Ser Asp
                180                 185                 190

Gln Leu Thr Glu Glu Gln Ile Ala Glu Phe Lys Glu Ala Phe Ser Leu
            195                 200                 205

Phe Asp Lys Asp Gly Asp Gly Thr Ile Thr Thr Lys Glu Leu Gly Thr
        210                 215                 220

Val Met Arg Ser Leu Gly Gln Asn Pro Thr Glu Ala Glu Leu Gln Asp
225                 230                 235                 240

Met Ile Asn Glu Val Asp Ala Asp Gly Asp Gly Thr Ile Asp Phe Pro
                245                 250                 255

Glu Phe Leu Thr Met Met Ala Arg Lys Met Lys Asp Thr Asp Ser Glu
            260                 265                 270

Glu Glu Ile Arg Glu Ala Phe Arg Val Phe Asp Lys Asp Gly Asn Gly
        275                 280                 285

Tyr Ile Ser Ala Ala Glu Leu Arg His Val Met Thr Asn Leu Gly Glu
    290                 295                 300

Lys Leu Thr Asp Glu Glu Val Asp Glu Met Ile Arg Glu Ala Asp Ile
305                 310                 315                 320

Asp Gly Asp Gly Gln Val Asn Tyr Glu Glu Phe Val Val Met Met Thr
                325                 330                 335

Ala Lys Thr Asn Glu Met Ala Leu Leu Leu Glu Gly Asn Ala His Tyr
            340                 345                 350

Arg Cys Asp Phe Arg Thr Thr Tyr Lys Ala Lys Glu Lys Gly Val Lys
        355                 360                 365

Leu Pro Gly Val His Tyr Val Asp His Thr Ile Glu Ile Leu Ser His
    370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 3
<211> LENGTH: 1230
<212> TYPE: DNA
<213> ORGANISM: Artificial Sequence
```

<220> FEATURE:
<223> OTHER INFORMATION: Synthetic

<400> SEQUENCE: 3

```
atggtgagtg cgattaagcc agacatgaag atcaaactgc gtatggaagg caacgtaaac      60
gggcaccact ttgtgatcga cggagatggt acaggcaagc ttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt tcctaaggg gtattcgtgg aacgaagca tgactttcga agacggggc       300
atttgctatg ccagaagcga cataacaatg aaggggaca ctttctataa taaagttcga     360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgatgtagca gcgaccagct gaccgaggag     540
caaattgcag aatttaagga ggcgttctct ttgtttgaca agatggcga cggtacaatt     600
acaaccaagg aattgggcac agtaatgcgc tcccttggac agaatcccac tgaagccgaa     660
cttcaagaca tgatcaatga ggttgatgct gacggggatg ggactatcga ctttcctgag     720
tttcttacca tgatggctcg caaaatgaag gatacagaca gtgaggagga aattcgtgag     780
gcctttcgtg tgtttgataa ggacgggaac ggttatatct cagcggcgga gctgcgtcac     840
gttatgacca acttaggcga aaagctgact gatgaagaag tcgatgagat gatccgcgag     900
gcggacatcg atggtgatgg tcaagtcaat tatgaagagt ttgtggtgat gatgaccgcg     960
aagggaggct ctggcggttc cggcggttca ggtggatcat caagccgccg caagttcaac    1020
aaaaccggcc atgccttgcg tgcaattggc cgcctgtcca gcgtcccgtt cagaactact    1080
tacaaagcta aggagaaggg tgtcaagtta ccaggcgtgc actatgtgga ccacaccatt    1140
gagattttaa gccatgacaa agattacaac aaggttaaga tctatgagta tgctgttgct    1200
cattctggat tgcctgacaa tgccagacga                                     1230
```

<210> SEQ ID NO 4
<211> LENGTH: 410
<212> TYPE: PRT
<213> ORGANISM: Artificial Sequence
<220> FEATURE:
<223> OTHER INFORMATION: Synthetic

<400> SEQUENCE: 4

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
```

```
                       115                 120                 125
Asn Gly Pro Val Met Gln Lys Lys Thr Leu Lys Trp Glu Pro Ser Thr
           130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Ser Ser Asp Gln
               165                 170                 175

Leu Thr Glu Glu Gln Ile Ala Glu Phe Lys Glu Ala Phe Ser Leu Phe
           180                 185                 190

Asp Lys Asp Gly Asp Gly Thr Ile Thr Thr Lys Glu Leu Gly Thr Val
       195                 200                 205

Met Arg Ser Leu Gly Gln Asn Pro Thr Glu Ala Glu Leu Gln Asp Met
210                 215                 220

Ile Asn Glu Val Asp Ala Asp Gly Asp Gly Thr Ile Asp Phe Pro Glu
225                 230                 235                 240

Phe Leu Thr Met Met Ala Arg Lys Met Lys Asp Thr Asp Ser Glu Glu
               245                 250                 255

Glu Ile Arg Glu Ala Phe Arg Val Phe Asp Lys Asp Gly Asn Gly Tyr
           260                 265                 270

Ile Ser Ala Ala Glu Leu Arg His Val Met Thr Asn Leu Gly Glu Lys
       275                 280                 285

Leu Thr Asp Glu Glu Val Asp Glu Met Ile Arg Glu Ala Asp Ile Asp
290                 295                 300

Gly Asp Gly Gln Val Asn Tyr Glu Glu Phe Val Val Met Met Thr Ala
305                 310                 315                 320

Lys Gly Gly Ser Gly Gly Ser Gly Gly Ser Gly Ser Ser Arg
               325                 330                 335

Arg Lys Phe Asn Lys Thr Gly His Ala Leu Arg Ala Ile Gly Arg Leu
           340                 345                 350

Ser Ser Val Pro Phe Arg Thr Thr Tyr Lys Ala Lys Glu Lys Gly Val
       355                 360                 365

Lys Leu Pro Gly Val His Tyr Val Asp His Thr Ile Glu Ile Leu Ser
370                 375                 380

His Asp Lys Asp Tyr Asn Lys Val Lys Ile Tyr Glu Tyr Ala Val Ala
385                 390                 395                 400

His Ser Gly Leu Pro Asp Asn Ala Arg Arg
               405                 410

<210> SEQ ID NO 5
<211> LENGTH: 1236
<212> TYPE: DNA
<213> ORGANISM: Artificial Sequence
<220> FEATURE:
<223> OTHER INFORMATION: Synthetic

<400> SEQUENCE: 5
atggtgagtg cgattaagcc agacatgaag atcaaactgc gtatggaagg caacgtaaac      60
gggcaccact ttgtgatcga cggagatggt acaggcaagc ttatgaggg aaaacagacc      120 atggatcttg aagtcaaaga gggcggacct ctgcctttg cctttgatat cctgaccact      180
gcattcctgt acggcaacag ggtattcgtg aaatatccag acaacataca agactatttt      240
aagcagtcgt ttcctaaggg gtattcgtgg gaacgaagca tgactttcga agacggggc      300 atttgctatg ccagaagcga cataacaatg aagggggaca ctttctataa taaagttcga      360
ttttatggta ccaacttcc cgccaatggt ccagttatgc agaagaagac gctgaaatgg      420
```

```
gagccctcca ctgagaaaat gtatgtgcgt gatggagtgc tgacgggtga tgtagagatg    480
gctttgttgc ttgaaggaaa tgcccattac cgatgtgaca tcgtcgacca gctgaccgag    540
gagcaaattg cagaatttaa ggaggcgttc tctttgtttg acaaagatgg cgacggtaca    600
attacaacca aggaattggg cacagtaatg cgctcccttg acagaatcc cactgaagcc    660 gaacttcaag acatgatcaa tgaggttgat gctgacgggg atgggactat cgactttcct    720
gagtttctta ccatgatggc tcgcaaaatg aaggatacag acagtgagga ggaaattcgt    780
gaggcctttc gtgtgtttga taaggacggg aacggttata tctcagcggc ggagctgcgt    840
cacgttatga ccaacttagg cgaaaagctg actgatgaag aagtcgatga gatgatccgc    900
gaggcggaca tcgatggtga tggtcaagtc aattatgaag agtttgtggt gatgatgacc    960
gcgaagggag gctctggcgg ttccggcggt tcaggtggat catcaagccg ccgcaagttc   1020
aacaaaaccg gccatgcctt gcgtgcaatt ggccgcctgt ccagctacac cgacttcaga   1080
actacttaca aagctaagga gaagggtgtc aagttaccag gcgtgcacta tgtggaccac   1140
accattgaga ttttaagcca tgacaaagat tacaacaagg ttaagatcta tgagtatgct   1200
gttgctcatt ctggattgcc tgacaatgcc agacga                             1236
```

<210> SEQ ID NO 6
<211> LENGTH: 412
<212> TYPE: PRT
<213> ORGANISM: Artificial Sequence
<220> FEATURE:
<223> OTHER INFORMATION: Synthetic

<400> SEQUENCE: 6

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Ile Val Asp
                165                 170                 175

Gln Leu Thr Glu Glu Gln Ile Ala Glu Phe Lys Glu Ala Phe Ser Leu
            180                 185                 190

Phe Asp Lys Asp Gly Asp Gly Thr Ile Thr Thr Lys Glu Leu Gly Thr
        195                 200                 205

Val Met Arg Ser Leu Gly Gln Asn Pro Thr Glu Ala Glu Leu Gln Asp
```

```
            210                 215                 220
Met Ile Asn Glu Val Asp Ala Asp Gly Asp Gly Thr Ile Asp Phe Pro
225                 230                 235                 240

Glu Phe Leu Thr Met Met Ala Arg Lys Met Lys Asp Thr Asp Ser Glu
                245                 250                 255

Glu Glu Ile Arg Glu Ala Phe Arg Val Phe Asp Lys Asp Gly Asn Gly
            260                 265                 270

Tyr Ile Ser Ala Ala Glu Leu Arg His Val Met Thr Asn Leu Gly Glu
        275                 280                 285

Lys Leu Thr Asp Glu Glu Val Asp Glu Met Ile Arg Glu Ala Asp Ile
290                 295                 300

Asp Gly Asp Gly Gln Val Asn Tyr Glu Glu Phe Val Val Met Met Thr
305                 310                 315                 320

Ala Lys Gly Gly Ser Gly Gly Ser Gly Gly Ser Ser Ser
                325                 330                 335

Arg Arg Lys Phe Asn Lys Thr Gly His Ala Leu Arg Ala Ile Gly Arg
                340                 345                 350

Leu Ser Ser Tyr Thr Asp Phe Arg Thr Thr Tyr Lys Ala Lys Glu Lys
        355                 360                 365

Gly Val Lys Leu Pro Gly Val His Tyr Val Asp His Thr Ile Glu Ile
370                 375                 380

Leu Ser His Asp Lys Asp Tyr Asn Lys Val Lys Ile Tyr Glu Tyr Ala
385                 390                 395                 400

Val Ala His Ser Gly Leu Pro Asp Asn Ala Arg Arg
                405                 410

<210> SEQ ID NO 7
<211> LENGTH: 1239
<212> TYPE: DNA
<213> ORGANISM: Artificial Sequence
<220> FEATURE:
<223> OTHER INFORMATION: Synthetic

<400> SEQUENCE: 7
atggtgagtg cgattaagcc agacatgaag atcaaactgc gtatggaagg caacgtaaac      60
gggcaccact ttgtgatcga cggagatggt acaggcaagc ttatgaggg aaaacagacc      120 atggatcttg aagtcaaaga gggcggacct ctgcctttg cctttgatat cctgaccact      180
gcattcctgt acggcaacag ggtattcgtg aaatatccag acaacatac agactatttt      240 aagcagtcgt ttcctaaggg gtattcgtgg aacgaagca tgactttcga agacgggggc      300
atttgctatg ccagaagcga cataacaatg aaggggaca ctttctataa taagttcga       360 tttatggta ccaactttcc cgccaatggt ccagttatgc agaagaagac gctgaaatgg      420
gagccctcca ctgagaaaat gtatgtgcgt gatggagtgc tgacgggtga tgtagagatg      480
gctttgttgc ttgaaggaaa tgcccattac cgatgtgact tccagagcga ccagctgacc      540
gaggagcaaa ttgcagaatt taaggaggcg ttctcttttgt ttgacaaaga tggcgacggt      600
acaattacaa ccaaggaatt gggcacagta atgcgctccc ttggacagaa tcccactgaa      660
gccgaacttc aagacatgat caatgaggtt gatgctgacg ggatgggac tatcgacttt      720 cctgagtttc ttaccatgat ggctcgcaaa atgaaggata cagacagtga ggaggaaatt      780
cgtgaggcct ttcgtgtgtt tgataaggac gggaacggtt atatctcagc ggcggagctg      840
cgtcacgtta tgaccaactt aggcgaaaag ctgactgatg aagaagtcga tgagatgatc      900
cgcgaggcgg acatcgatgg tgatggtcaa gtcaattatg aagagtttgt ggtgatgatg      960
```

```
accgcgaagg gaggctctgg cggttccggc ggttcaggtg gatcatcaag ccgccgcaag   1020
ttcaacaaaa ccggccatgc cttgcgtgca attggccgcc tgtccagccg caccgacttc   1080
agaactactt acaaagctaa ggagaagggt gtcaagttac caggcgtgca ctatgtggac   1140
cacaccattg agattttaag ccatgacaaa gattacaaca aggttaagat ctatgagtat   1200
gctgttgctc attctggatt gcctgacaat gccagacga                          1239
```

<210> SEQ ID NO 8
<211> LENGTH: 413
<212> TYPE: PRT
<213> ORGANISM: Artificial Sequence
<220> FEATURE:
<223> OTHER INFORMATION: Synthetic

<400> SEQUENCE: 8

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Phe Gln Ser
                165                 170                 175

Asp Gln Leu Thr Glu Glu Gln Ile Ala Glu Phe Lys Glu Ala Phe Ser
            180                 185                 190

Leu Phe Asp Lys Asp Gly Asp Gly Thr Ile Thr Thr Lys Glu Leu Gly
        195                 200                 205

Thr Val Met Arg Ser Leu Gly Gln Asn Pro Thr Glu Ala Glu Leu Gln
    210                 215                 220

Asp Met Ile Asn Glu Val Asp Ala Asp Gly Asp Gly Thr Ile Asp Phe
225                 230                 235                 240

Pro Glu Phe Leu Thr Met Met Ala Arg Lys Met Lys Asp Thr Asp Ser
                245                 250                 255

Glu Glu Glu Ile Arg Glu Ala Phe Arg Val Phe Asp Lys Asp Gly Asn
            260                 265                 270

Gly Tyr Ile Ser Ala Ala Glu Leu Arg His Val Met Thr Asn Leu Gly
        275                 280                 285

Glu Lys Leu Thr Asp Glu Glu Val Asp Glu Met Ile Arg Glu Ala Asp
    290                 295                 300

Ile Asp Gly Asp Gly Gln Val Asn Tyr Glu Glu Phe Val Val Met Met
```

```
                    305                 310                 315                 320
Thr Ala Lys Gly Gly Ser Gly Gly Ser Gly Gly Ser Gly Gly Ser Ser
                325                 330                 335

Ser Arg Arg Lys Phe Asn Lys Thr Gly His Ala Leu Arg Ala Ile Gly
            340                 345                 350

Arg Leu Ser Ser Arg Thr Asp Phe Arg Thr Thr Tyr Lys Ala Lys Glu
        355                 360                 365

Lys Gly Val Lys Leu Pro Gly Val His Tyr Val Asp His Thr Ile Glu
    370                 375                 380

Ile Leu Ser His Asp Lys Asp Tyr Asn Lys Val Lys Ile Tyr Glu Tyr
385                 390                 395                 400

Ala Val Ala His Ser Gly Leu Pro Asp Asn Ala Arg Arg
                405                 410
```

<210> SEQ ID NO 9
<211> LENGTH: 1236
<212> TYPE: DNA
<213> ORGANISM: Artificial Sequence
<220> FEATURE:
<223> OTHER INFORMATION: Synthetic

<400> SEQUENCE: 9

```
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacgggggc      300
atttgctatg ccagaagcga cataacaatg aaggggaca cttttctataa taagttcga     360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgatgtgacg ggcaggacca gctgaccgag     540
gagcaaattg cagaatttaa ggaggcgttc tctttgtttg acaaagatgg cgacggtaca     600
attacaacca aggaattggg cacagtaatg cgctcccttg acagaatcc cactgaagcc      660
gaacttcaag acatgatcaa tgaggttgat gctgacgggg atgggactat cgactttcct     720
gagtttctta ccatgatggc tcgcaaaatg aaggatacag acagtgagga ggaaattcgt     780
gaggcctttc gtgtgtttga taaggacggg aacggttata tctcagcggc ggagctgcgt     840
cacgttatga ccaacttagg cgaaaagctg actgatgaag aagtcgatga tgatgatccgc    900
gaggcggaca tcgatggtga tggtcaagtc aattatgaag agtttgtggt gatgatgacc     960
gcgaagggag gctctggcgg ttccggcggt tcaggtggat catcaagccg ccgcaagttc    1020
aacaaaaccg gccatgcctt gcgtgcaatt ggccgcctgt ccagctacac ggacttcaga    1080
actacttaca agctaaggat gaagggtgtc aagttaccag cgtgcactata tgtgaccac    1140
accattgaga ttttaagcca tgacaaagat tacaacaagg ttaagatcta tgagtatgct    1200
gttgctcatt ctggattgcc tgacaatgcc agacga                              1236
```

<210> SEQ ID NO 10
<211> LENGTH: 412
<212> TYPE: PRT
<213> ORGANISM: Artificial Sequence
<220> FEATURE:
<223> OTHER INFORMATION: Synthetic

<400> SEQUENCE: 10

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Gly Gln Asp
                165                 170                 175

Gln Leu Thr Glu Glu Gln Ile Ala Glu Phe Lys Glu Ala Phe Ser Leu
            180                 185                 190

Phe Asp Lys Asp Gly Asp Gly Thr Ile Thr Thr Lys Glu Leu Gly Thr
        195                 200                 205

Val Met Arg Ser Leu Gly Gln Asn Pro Thr Glu Ala Glu Leu Gln Asp
210                 215                 220

Met Ile Asn Glu Val Asp Ala Asp Gly Asp Gly Thr Ile Asp Phe Pro
225                 230                 235                 240

Glu Phe Leu Thr Met Met Ala Arg Lys Met Lys Asp Thr Asp Ser Glu
                245                 250                 255

Glu Glu Ile Arg Glu Ala Phe Arg Val Phe Asp Lys Asp Gly Asn Gly
            260                 265                 270

Tyr Ile Ser Ala Ala Glu Leu Arg His Val Met Thr Asn Leu Gly Glu
        275                 280                 285

Lys Leu Thr Asp Glu Glu Val Asp Glu Met Ile Arg Glu Ala Asp Ile
290                 295                 300

Asp Gly Asp Gly Gln Val Asn Tyr Glu Glu Phe Val Val Met Met Thr
305                 310                 315                 320

Ala Lys Gly Gly Ser Gly Gly Ser Gly Gly Ser Gly Gly Ser Ser Ser
                325                 330                 335

Arg Arg Lys Phe Asn Lys Thr Gly His Ala Leu Arg Ala Ile Gly Arg
            340                 345                 350

Leu Ser Ser Tyr Thr Asp Phe Arg Thr Thr Tyr Lys Ala Lys Glu Lys
        355                 360                 365

Gly Val Lys Leu Pro Gly Val His Tyr Val Asp His Thr Ile Glu Ile
    370                 375                 380

Leu Ser His Asp Lys Asp Tyr Asn Lys Val Lys Ile Tyr Glu Tyr Ala
385                 390                 395                 400

Val Ala His Ser Gly Leu Pro Asp Asn Ala Arg Arg

<210> SEQ ID NO 11
<211> LENGTH: 1233
<212> TYPE: DNA
<213> ORGANISM: Artificial Sequence
<220> FEATURE:
<223> OTHER INFORMATION: Synthetic

<400> SEQUENCE: 11

```
atggtgagtg cgattaagcc agacatgaag atcaaactgc gtatggaagg caacgtaaac      60
gggcaccact tgtgtatcga cggagatggt acaggcaagc ttatgaggg aaaacagacc     120
atggatcttg aagtcaaaga gggcggacct ctgcctttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacgggggc     300
atttgctatg ccagaagcga cataacaatg aaggggaca cttctataa taaagttcga     360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgatgtgaca agttcgacca gctgaccgag     540
gagcaaattg cagaatttaa ggaggcgttc tctttgtttg acaaagatgg cgacggtaca     600
attacaacca aggaattggg cacagtaatg cgctcccttg acagaatcc cactgaagcc     660
gaacttcaag acatgatcaa tgaggttgat gctgacgggg atgggactat cgactttcct     720
gagtttctta ccatgatggc tcgcaaaatg aaggatacag acagtgagga ggaaattcgt     780
gaggcctttc gtgtgtttga taggacggg aacggttata tctcagcggc ggagctgcgt     840
cacgttatga ccaacttagg cgaaaagctg actgatgaag aagtcgatga atgatccgc     900
gaggcggaca tcgatggtga tggtcaagtc aattatgaag agtttgtggt gatgatgacc     960
gcgaagggag gctctggcgg ttccggcggt tcaggtggat catcaagccg ccgcaagttc    1020
aacaaaaccg ccatgccttt cgtgcaattt ggccgcctgt ccagcgtgcc cttcagaact    1080
acttacaaag ctaaggagaa gggtgtcaag ttaccaggcg tgcactatgt ggaccacacc    1140
attgagattt taagccatga caaagattac aacaaggtta agatctatga gtatgctgtt    1200
gctcattctg gattgcctga caatgccaga cga                                 1233
```

<210> SEQ ID NO 12
<211> LENGTH: 411
<212> TYPE: PRT
<213> ORGANISM: Artificial Sequence
<220> FEATURE:
<223> OTHER INFORMATION: Synthetic

<400> SEQUENCE: 12

```
Met Val Ser Ala Ile Lys Pro Asp Met Lys Ile Lys Leu Arg Met Glu
 1               5                  10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
 65                  70                  75                  80
```

```
Lys Gln Ser Phe Pro Lys Gly Tyr Ser Trp Glu Arg Ser Met Thr Phe
                85                  90                  95
Glu Asp Gly Gly Ile Cys Tyr Ala Arg Ser Asp Ile Thr Met Glu Gly
            100                 105                 110
Asp Thr Phe Tyr Asn Lys Val Arg Phe Tyr Gly Thr Asn Phe Pro Ala
            115                 120                 125
Asn Gly Pro Val Met Gln Lys Thr Leu Lys Trp Glu Pro Ser Thr
            130             135                 140
Glu Lys Met Tyr Val Arg Asp Gly Val Leu Thr Gly Asp Val Glu Met
145                 150                 155                 160
Ala Leu Leu Leu Glu Gly Asn Ala His Tyr Arg Cys Asp Lys Phe Asp
                165                 170                 175
Gln Leu Thr Glu Glu Gln Ile Ala Glu Phe Lys Glu Ala Phe Ser Leu
            180                 185                 190
Phe Asp Lys Asp Gly Asp Gly Thr Ile Thr Thr Lys Glu Leu Gly Thr
            195                 200                 205
Val Met Arg Ser Leu Gly Gln Asn Pro Thr Glu Ala Glu Leu Gln Asp
            210                 215                 220
Met Ile Asn Glu Val Asp Ala Asp Gly Asp Gly Thr Ile Asp Phe Pro
225                 230                 235                 240
Glu Phe Leu Thr Met Met Ala Arg Lys Met Lys Asp Thr Asp Ser Glu
                245                 250                 255
Glu Glu Ile Arg Glu Ala Phe Arg Val Phe Asp Lys Asp Gly Asn Gly
            260                 265                 270
Tyr Ile Ser Ala Ala Glu Leu Arg His Val Met Thr Asn Leu Gly Glu
            275                 280                 285
Lys Leu Thr Asp Glu Glu Val Asp Glu Met Ile Arg Glu Ala Asp Ile
            290                 295                 300
Asp Gly Asp Gly Gln Val Asn Tyr Glu Glu Phe Val Val Met Met Thr
305                 310                 315                 320
Ala Lys Gly Gly Ser Gly Gly Ser Gly Gly Ser Ser Ser
                325                 330                 335
Arg Arg Lys Phe Asn Lys Thr Gly His Ala Leu Arg Ala Ile Gly Arg
            340                 345                 350
Leu Ser Ser Val Pro Phe Arg Thr Thr Tyr Lys Ala Lys Glu Lys Gly
            355                 360                 365
Val Lys Leu Pro Gly Val His Tyr Val Asp His Thr Ile Glu Ile Leu
            370                 375                 380
Ser His Asp Lys Asp Tyr Asn Lys Val Lys Ile Tyr Glu Tyr Ala Val
385                 390                 395                 400
Ala His Ser Gly Leu Pro Asp Asn Ala Arg Arg
                405                 410
```

<210> SEQ ID NO 13
<211> LENGTH: 1236
<212> TYPE: DNA
<213> ORGANISM: Artificial Sequence
<220> FEATURE:
<223> OTHER INFORMATION: Synthetic

<400> SEQUENCE: 13

```
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgcctttg cctttgatat cctgaccact     180
```

```
gcattcctgt acggcaacag ggtattcgtg aaatatccag acaacataca agactatttt    240
aagcagtcgt ttcctaaggg gtattcgtgg gaacgaagca tgactttcga agacggggc     300
atttgctatg ccagaagcga cataacaatg aaggggaca ctttctataa taaagttcga     360
ttttatggta ccaactttcc cgccaatggt ccagttatgc agaagaagac gctgaaatgg    420
gagccctcca ctgagaaaat gtatgtgcgt gatggagtgc tgacgggtga tgtagagatg    480
gctttgttgc ttgaaggaaa tgcccattac cgatgtgact tctacttgga ccagctgacc    540
gaggagcaaa ttgcagaatt taaggaggcg ttctctttgt ttgacaaaga tggcgacggt    600
acaattacaa ccaaggaatt gggcacagta atgcgctccc ttggacagaa tcccactgaa    660
gccgaacttc aagacatgat caatgaggtt gatgctgacg gggatgggac tatcgacttt    720
cctgagtttc ttaccatgat ggctcgcaaa atgaaggata cagacagtga ggaggaaatt    780
cgtgaggcct ttcgtgtgtt tgataaggac gggaacggtt atatctcagc ggcggagctg    840
cgtcacgtta tgaccaactt aggcgaaaag ctgactgatg aagaagtcga tgagatgatc    900
cgcgaggcgg acatcgatgg tgatggtcaa gtcaattatg aagagtttgt ggtgatgatg    960
accgcgaagg gaggctctgg cggttccggc ggttcaggtg gatcatcaag ccgccgcaag   1020
ttcaacaaaa ccggccatgc cttgcgtgca attggccgcc tgtccagcgg gacgttcaga   1080
actacttaca aagctaagga gaagggtgtc aagttaccag gcgtgcacta tgtggaccac   1140
accattgaga ttttaagcca tgacaaagat tacaacaagg ttaagatcta tgagtatgct   1200
gttgctcatt ctggattgcc tgacaatgcc agacga                             1236
```

<210> SEQ ID NO 14
<211> LENGTH: 412
<212> TYPE: PRT
<213> ORGANISM: Artificial Sequence
<220> FEATURE:
<223> OTHER INFORMATION: Synthetic

<400> SEQUENCE: 14

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Phe Tyr Leu
                165                 170                 175
```

```
Asp Gln Leu Thr Glu Glu Gln Ile Ala Glu Phe Lys Glu Ala Phe Ser
            180                 185                 190
Leu Phe Asp Lys Asp Gly Asp Gly Thr Ile Thr Thr Lys Glu Leu Gly
        195                 200                 205
Thr Val Met Arg Ser Leu Gly Gln Asn Pro Thr Glu Ala Glu Leu Gln
    210                 215                 220
Asp Met Ile Asn Glu Val Asp Ala Asp Gly Asp Gly Thr Ile Asp Phe
225                 230                 235                 240
Pro Glu Phe Leu Thr Met Met Ala Arg Lys Met Lys Asp Thr Asp Ser
            245                 250                 255
Glu Glu Glu Ile Arg Glu Ala Phe Arg Val Phe Asp Lys Asp Gly Asn
        260                 265                 270
Gly Tyr Ile Ser Ala Ala Glu Leu Arg His Val Met Thr Asn Leu Gly
    275                 280                 285
Glu Lys Leu Thr Asp Glu Glu Val Asp Glu Met Ile Arg Glu Ala Asp
290                 295                 300
Ile Asp Gly Asp Gly Gln Val Asn Tyr Glu Glu Phe Val Val Met Met
305                 310                 315                 320
Thr Ala Lys Gly Gly Ser Gly Gly Ser Gly Gly Ser Gly Gly Ser Ser
            325                 330                 335
Ser Arg Arg Lys Phe Asn Lys Thr Gly His Ala Leu Arg Ala Ile Gly
        340                 345                 350
Arg Leu Ser Ser Gly Thr Phe Arg Thr Thr Tyr Lys Ala Lys Glu Lys
    355                 360                 365
Gly Val Lys Leu Pro Gly Val His Tyr Val Asp His Thr Ile Glu Ile
    370                 375                 380
Leu Ser His Asp Lys Asp Tyr Asn Lys Val Lys Ile Tyr Glu Tyr Ala
385                 390                 395                 400
Val Ala His Ser Gly Leu Pro Asp Asn Ala Arg Arg
            405                 410

<210> SEQ ID NO 15
<211> LENGTH: 1233
<212> TYPE: DNA
<213> ORGANISM: Artificial Sequence
<220> FEATURE:
<223> OTHER INFORMATION: Synthetic

<400> SEQUENCE: 15
atggtgagtg cgattaagcc agacatgaag atcaaactgc gtatggaagg caacgtaaac      60
gggcaccact ttgtgatcga cggagatggt acaggcaagc ttatgaggg aaaacagacc      120 atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga agacgggggc       300
atttgctatg ccagaagcga cataacaatg aaggggacac ttttctataa taagttcga      360 ttttatggta ccaactttcc cgccaatggt ccagttatgc agaagaagac gctgaaatgg      420
gagccctcca ctgagaaaat gtatgtgcgt gatggagtgc tgacgggtga tgtagagatg      480
gctttgttgc ttgaaggaaa tgcccattac cgatgtgact gggcgacca gctgaccgag      540 gagcaaattg cagaatttaa ggaggcgttc tctttgtttg acaaagatgg cgacggtaca      600
attacaacca aggaattggg cacagtaatg cgctcccttg acagaatcc cactgaagcc      660 gaacttcaag acatgatcaa tgaggttgat gctgacgggg atgggactat cgactttcct      720
```

-continued

```
gagtttctta ccatgatggc tcgcaaaatg aaggatacag acagtgagga ggaaattcgt      780
gaggcctttc gtgtgtttga taaggacggg aacggttata tctcagcggc ggagctgcgt      840
cacgttatga ccaacttagg cgaaaagctg actgatgaag aagtcgatga gatgatccgc      900
gaggcggaca tcgatggtga tggtcaagtc aattatgaag agtttgtggt gatgatgacc      960
gcgaagggag gctctggcgg ttccggcggt tcaggtggat catcaagccg ccgcaagttc     1020
aacaaaaccg gccatgcctt gcgtgcaatt ggccgcctgt ccagcaacca gttcagaact     1080
acttacaaag ctaaggagaa gggtgtcaag ttaccaggcg tgcactatgt ggaccacacc     1140
attgagattt taagccatga caaagattac aacaaggtta agatctatga gtatgctgtt     1200
gctcattctg gattgcctga caatgccaga cga                                 1233
```

<210> SEQ ID NO 16
<211> LENGTH: 411
<212> TYPE: PRT
<213> ORGANISM: Artificial Sequence
<220> FEATURE:
<223> OTHER INFORMATION: Synthetic

<400> SEQUENCE: 16

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Leu Gly Asp
                165                 170                 175

Gln Leu Thr Glu Glu Gln Ile Ala Glu Phe Lys Glu Ala Phe Ser Leu
            180                 185                 190

Phe Asp Lys Asp Gly Asp Gly Thr Ile Thr Thr Lys Glu Leu Gly Thr
        195                 200                 205

Val Met Arg Ser Leu Gly Gln Asn Pro Thr Glu Ala Glu Leu Gln Asp
    210                 215                 220

Met Ile Asn Glu Val Asp Ala Asp Gly Asp Gly Thr Ile Asp Phe Pro
225                 230                 235                 240

Glu Phe Leu Thr Met Met Ala Arg Lys Met Lys Asp Thr Asp Ser Glu
                245                 250                 255

Glu Glu Ile Arg Glu Ala Phe Arg Val Phe Asp Lys Asp Gly Asn Gly
            260                 265                 270
```

```
Tyr Ile Ser Ala Ala Glu Leu Arg His Val Met Thr Asn Leu Gly Glu
            275                 280                 285

Lys Leu Thr Asp Glu Glu Val Asp Glu Met Ile Arg Glu Ala Asp Ile
        290                 295                 300

Asp Gly Asp Gly Gln Val Asn Tyr Glu Glu Phe Val Val Met Met Thr
305                 310                 315                 320

Ala Lys Gly Gly Ser Gly Ser Gly Ser Gly Gly Ser Ser Ser
            325                 330                 335

Arg Arg Lys Phe Asn Lys Thr Gly His Ala Leu Arg Ala Ile Gly Arg
                340                 345                 350

Leu Ser Ser Asn Gln Phe Arg Thr Thr Tyr Lys Ala Lys Glu Lys Gly
            355                 360                 365

Val Lys Leu Pro Gly Val His Tyr Val Asp His Thr Ile Glu Ile Leu
        370                 375                 380

Ser His Asp Lys Asp Tyr Asn Lys Val Lys Ile Tyr Glu Tyr Ala Val
385                 390                 395                 400

Ala His Ser Gly Leu Pro Asp Asn Ala Arg Arg
            405                 410

<210> SEQ ID NO 17
<211> LENGTH: 1236
<212> TYPE: DNA
<213> ORGANISM: Artificial Sequence
<220> FEATURE:
<223> OTHER INFORMATION: Synthetic

<400> SEQUENCE: 17
atggtgagtg cgattaagcc agacatgaag atcaaactgc gtatggaagg caacgtaaac      60
gggcaccact ttgtgatcga cggagatggt acaggcaagc ttatgaggg aaaacagacc      120 atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga agacgggggc      300
atttgctatg ccagaagcga cataacaatg aagggggaca cttttctataa taaagttcga      360 ttttatggta ccaactttcc cgccaatggt ccagttatgc agaagaagac gctgaaatgg      420
gagccctcca ctgagaaaat gtatgtgcgt gatggagtgc tgacgggtga tgtagagatg      480
gctttgttgc ttgaaggaaa tgcccattac cgatgtgacc ccgtcgacca gctgaccgag      540
gagcaaattg cagaatttaa ggaggcgttc tctttgtttg acaaagatgg cgacggtaca      600
attacaacca aggaattggg cacagtaatg cgctcccttg acagaatcc cactgaagcc      660 gaacttcaag acatgatcaa tgaggttgat gctgacgggg atgggactat cgactttcct      720
gagtttctta ccatgatggc tcgcaaaatg aaggatacag acagtgagga ggaaattcgt      780
gaggcctttc gtgtgtttga taggacggg aacggttata tctcagcggc ggagctgcgt      840
cacgttatga ccaacttagg cgaaaagctg actgatgaag aagtcgatga gatgatccgc      900
gaggcggaca tcgatggtga tggtcaagtc aattatgaag agtttgtggt gatgatgacc      960
gcgaagggag gctctggcgg ttccggcggt tcaggtggat catcaagccg ccgcaagttc     1020
aacaaaaccg gccatgcctt gcgtgcaatt ggccgcctgt ccagcagcat cgacttcaga     1080
actacttaca agctaagga agggtgtc aagttaccag gcgtgcacta tgtggaccac     1140
accattgaga ttttaagcca tgacaaagat tacaacaagg ttaagatcta tgagtatgct     1200
gttgctcatt ctggattgcc tgacaatgcc agacga                               1236
```

<210> SEQ ID NO 18
<211> LENGTH: 412
<212> TYPE: PRT
<213> ORGANISM: Artificial Sequence
<220> FEATURE:
<223> OTHER INFORMATION: Synthetic

<400> SEQUENCE: 18

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Pro Val Asp
                165                 170                 175

Gln Leu Thr Glu Glu Gln Ile Ala Glu Phe Lys Glu Ala Phe Ser Leu
            180                 185                 190

Phe Asp Lys Asp Gly Asp Gly Thr Ile Thr Thr Lys Glu Leu Gly Thr
        195                 200                 205

Val Met Arg Ser Leu Gly Gln Asn Pro Thr Glu Ala Glu Leu Gln Asp
    210                 215                 220

Met Ile Asn Glu Val Asp Ala Asp Gly Asp Gly Thr Ile Asp Phe Pro
225                 230                 235                 240

Glu Phe Leu Thr Met Met Ala Arg Lys Met Lys Asp Thr Asp Ser Glu
                245                 250                 255

Glu Glu Ile Arg Glu Ala Phe Arg Val Phe Asp Lys Asp Gly Asn Gly
            260                 265                 270

Tyr Ile Ser Ala Ala Glu Leu Arg His Val Met Thr Asn Leu Gly Glu
        275                 280                 285

Lys Leu Thr Asp Glu Glu Val Asp Glu Met Ile Arg Glu Ala Asp Ile
    290                 295                 300

Asp Gly Asp Gly Gln Val Asn Tyr Glu Glu Phe Val Val Met Met Thr
305                 310                 315                 320

Ala Lys Gly Gly Ser Gly Gly Ser Gly Gly Ser Gly Gly Ser Ser Ser
                325                 330                 335

Arg Arg Lys Phe Asn Lys Thr Gly His Ala Leu Arg Ala Ile Gly Arg
            340                 345                 350

Leu Ser Ser Ser Ile Asp Phe Arg Thr Thr Tyr Lys Ala Lys Glu Lys
        355                 360                 365
```

Gly Val Lys Leu Pro Gly Val His Tyr Val Asp His Thr Ile Glu Ile
            370             375             380

Leu Ser His Asp Lys Asp Tyr Asn Lys Val Lys Ile Tyr Glu Tyr Ala
385             390             395             400

Val Ala His Ser Gly Leu Pro Asp Asn Ala Arg Arg
            405             410

<210> SEQ ID NO 19
<211> LENGTH: 1233
<212> TYPE: DNA
<213> ORGANISM: Artificial Sequence
<220> FEATURE:
<223> OTHER INFORMATION: Synthetic

<400> SEQUENCE: 19

| | | | | | |
|---|---|---|---|---|---|
| atggtgagtg | cgattaagcc | agacatgaag | atcaaactgc | gtatggaagg | caacgtaaac | 60 |
| gggcaccact | tgtgatcga | cggagatggt | acaggcaagc | ttatgaggg | aaaacagacc | 120 |
| atggatcttg | aagtcaaaga | gggcggacct | ctgccttttg | cctttgatat | cctgaccact | 180 |
| gcattcctgt | acggcaacag | ggtattcgtg | aaatatccag | acaacataca | agactatttt | 240 |
| aagcagtcgt | tcctaaggg | gtattcgtgg | gaacgaagca | tgactttcga | agacgggggc | 300 |
| atttgctatg | ccagaagcga | cataacaatg | aaggggaca | cttctataa | taaagttcga | 360 |
| ttttatggta | ccaactttcc | cgccaatggt | ccagttatgc | agaagaagac | gctgaaatgg | 420 |
| gagccctcca | ctgagaaaat | gtatgtgcgt | gatggagtgc | tgacgggtga | tgtagagatg | 480 |
| gctttgttgc | ttgaaggaaa | tgcccattac | cgatgtgacc | ggcggtcaag | ccgccgcaag | 540 |
| ttcaacaaaa | ccggccatgc | cttgcgtgca | attggccgcc | tgtccagcgg | aggctctggc | 600 |
| ggttccggcg | gttcaggtgg | atcagaccag | ctgaccgagg | agcaaattgc | agaatttaag | 660 |
| gaggcgttct | ctttgtttga | caaagatggc | gacggtacaa | ttacaaccaa | ggaattgggc | 720 |
| acagtaatgc | gctcccttgg | acagaatccc | actgaagccg | aacttcaaga | catgatcaat | 780 |
| gaggttgatg | ctgacgggga | tgggactatc | gactttcctg | agtttcttac | catgatggct | 840 |
| cgcaaaatga | aggatacaga | cagtgaggag | gaaattcgtg | aggcctttcg | tgtgtttgat | 900 |
| aaggacggga | acggttatat | ctcagcggcg | gagctgcgtc | acgttatgac | caacttaggc | 960 |
| gaaaagctga | ctgatgaaga | agtcgatgag | atgatccgcg | aggcggacat | cgatggtgat | 1020 |
| ggtcaagtca | attatgaaga | gttgtggtg | atgatgaccg | cgaaggcctg | gttcagaact | 1080 |
| acttacaaag | ctaaggagaa | gggtgtcaag | ttaccaggcg | tgcactatgt | ggaccacacc | 1140 |
| attgagattt | taagccatga | caaagattac | aacaaggtta | agatctatga | gtatgctgtt | 1200 |
| gctcattctg | gattgcctga | caatgccaga | cga | | | 1233 |

<210> SEQ ID NO 20
<211> LENGTH: 411
<212> TYPE: PRT
<213> ORGANISM: Artificial Sequence
<220> FEATURE:
<223> OTHER INFORMATION: Synthetic

<400> SEQUENCE: 20

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20              25                  30

Lys Pro Tyr Glu Gly Lys Gln Thr Met Asp Leu Glu Val Lys Glu Gly
            35              40                  45

Gly Pro Leu Pro Phe Ala Phe Asp Ile Leu Thr Thr Ala Phe Leu Tyr
 50                  55                  60

Gly Asn Arg Val Phe Val Lys Tyr Pro Asp Asn Ile Gln Asp Tyr Phe
 65                  70                  75                  80

Lys Gln Ser Phe Pro Lys Gly Tyr Ser Trp Glu Arg Ser Met Thr Phe
                 85                  90                  95

Glu Asp Gly Gly Ile Cys Tyr Ala Arg Ser Asp Ile Thr Met Glu Gly
             100                 105                 110

Asp Thr Phe Tyr Asn Lys Val Arg Phe Tyr Gly Thr Asn Phe Pro Ala
         115                 120                 125

Asn Gly Pro Val Met Gln Lys Lys Thr Leu Lys Trp Glu Pro Ser Thr
130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Asp Arg Arg Ser
                165                 170                 175

Ser Arg Arg Lys Phe Asn Lys Thr Gly His Ala Leu Arg Ala Ile Gly
            180                 185                 190

Arg Leu Ser Ser Gly Ser Gly Gly Ser Gly Gly Ser Gly Gly Gly Ser
        195                 200                 205

Asp Gln Leu Thr Glu Glu Gln Ile Ala Glu Phe Lys Glu Ala Phe Ser
    210                 215                 220

Leu Phe Asp Lys Asp Gly Asp Gly Thr Ile Thr Thr Lys Glu Leu Gly
225                 230                 235                 240

Thr Val Met Arg Ser Leu Gly Gln Asn Pro Thr Glu Ala Glu Leu Gln
                245                 250                 255

Asp Met Ile Asn Glu Val Asp Ala Asp Gly Asp Gly Thr Ile Asp Phe
            260                 265                 270

Pro Glu Phe Leu Thr Met Met Ala Arg Lys Met Lys Asp Thr Asp Ser
        275                 280                 285

Glu Glu Glu Ile Arg Glu Ala Phe Arg Val Phe Asp Lys Asp Gly Asn
    290                 295                 300

Gly Tyr Ile Ser Ala Ala Glu Leu Arg His Val Met Thr Asn Leu Gly
305                 310                 315                 320

Glu Lys Leu Thr Asp Glu Glu Val Asp Glu Met Ile Arg Glu Ala Asp
                325                 330                 335

Ile Asp Gly Asp Gly Gln Val Asn Tyr Glu Glu Phe Val Val Met Met
            340                 345                 350

Thr Ala Lys Ala Trp Phe Arg Thr Thr Tyr Lys Ala Lys Glu Lys Gly
        355                 360                 365

Val Lys Leu Pro Gly Val His Tyr Val Asp His Thr Ile Glu Ile Leu
    370                 375                 380

Ser His Asp Lys Asp Tyr Asn Lys Val Lys Ile Tyr Glu Tyr Ala Val
385                 390                 395                 400

Ala His Ser Gly Leu Pro Asp Asn Ala Arg Arg
                405                 410

<210> SEQ ID NO 21
<211> LENGTH: 1227
<212> TYPE: DNA
<213> ORGANISM: Artificial Sequence
<220> FEATURE:
<223> OTHER INFORMATION: Synthetic

<400> SEQUENCE: 21

```
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga gacgggggc      300 atttgctatg ccagaagcga cataacaatg aagggggaca ctttctataa taaagttcga     360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgagacctgt caagccgccg caagttcaac     540
aaaaccggcc atgccttgcg tgcaattggc cgcctgtcca gcggaggctc tggcggttcc     600
ggcggttcag gtggatcaga ccagctgacc gaggagcaaa ttgcagaatt taaggaggcg     660
ttctctttgt ttgacaaaga tggcgacggt acaattacaa ccaaggaatt gggcacagta     720
atgcgctccc ttggacagaa tcccactgaa gccgaacttc aagacatgat caatgaggtt     780
gatgctgacg gggatgggac tatcgacttt cctgagtttc ttaccatgat ggctcgcaaa     840
atgaaggata cagacagtga ggaggaaatt cgtgaggcct tcgtgtgtt tgataaggac     900 gggaacggtt atatctcagc ggcggagctg cgtcacgtta tgaccaactt aggcgaaaag     960
ctgactgatg aagaagtcga tgagatgatc cgcgaggcgg acatcgatgg tgatggtcaa    1020
gtcaattatg aagagtttgt ggtgatgatg accgcgaagg cgttgttcag aactacttac    1080
aaagctaagg agaagggtgt caagttacca ggcgtgcact atgtggacca caccattgag    1140
attttaagcc atgacaaaga ttacaacaag gttaagatct atgagtatgc tgttgctcat    1200
tctggattgc ctgacaatgc cagacga                                        1227
```

<210> SEQ ID NO 22
<211> LENGTH: 409
<212> TYPE: PRT
<213> ORGANISM: Artificial Sequence
<220> FEATURE:
<223> OTHER INFORMATION: Synthetic

<400> SEQUENCE: 22

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140
```

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Asp Leu Ser Ser Arg
            165                 170                 175

Arg Lys Phe Asn Lys Thr Gly His Ala Leu Arg Ala Ile Gly Arg Leu
        180                 185                 190

Ser Ser Gly Gly Ser Gly Gly Ser Gly Gly Ser Gly Gly Ser Asp Gln
    195                 200                 205

Leu Thr Glu Glu Gln Ile Ala Glu Phe Lys Glu Ala Phe Ser Leu Phe
210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
            245                 250                 255

Ile Asn Glu Val Asp Ala Asp Gly Asp Gly Thr Ile Asp Phe Pro Glu
        260                 265                 270

Phe Leu Thr Met Met Ala Arg Lys Met Lys Asp Thr Asp Ser Glu Glu
    275                 280                 285

Glu Ile Arg Glu Ala Phe Arg Val Phe Asp Lys Asp Gly Asn Gly Tyr
290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
            325                 330                 335

Gly Asp Gly Gln Val Asn Tyr Glu Glu Phe Val Val Met Met Thr Ala
        340                 345                 350

Lys Ala Leu Phe Arg Thr Thr Tyr Lys Ala Lys Glu Lys Gly Val Lys
    355                 360                 365

Leu Pro Gly Val His Tyr Val Asp His Thr Ile Glu Ile Leu Ser His
370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
            405

<210> SEQ ID NO 23
<211> LENGTH: 2031
<212> TYPE: DNA
<213> ORGANISM: Artificial Sequence
<220> FEATURE:
<223> OTHER INFORMATION: Synthetic

<400> SEQUENCE: 23
atgctgcaga acgagcttgc tcttaagttg gctggacttg atattaacaa gactggaggt      60
tctcatcatc accaccacca tggatccatg gtgagtgcga ttaagccaga catgaagatc     120
aaactgcgta tggaaggcaa cgtaaacggg caccactttg tgatcgacgg agatggtaca     180
ggcaagcctt atgagggaaa acagaccatg gatcttgaag tcaaagaggg cggacctctg     240
ccttttgcct tgatatcct gaccactgca ttcctgtacg caacagggt attcgtgaaa      300 tatccagaca acatacaaga ctattttaag cagtcgtttc ctaaggggta ttcgtgggaa     360
cgaagcatga ctttcgaaga cggggggcatt tgctatgcca aagcgacat aacaatggaa     420 ggggacactt tctataataa agttcgattt tatggtacca actttcccgc caatggtcca     480
gttatgcaga agaagacgct gaaatgggag ccctccactg agaaaatgta tgtgcgtgat     540

-continued

```
ggagtgctga cgggtgatgt agagatggct tgttgcttg aaggaaatgc ccattaccga    600
gcgttgtcaa gccgccgcaa gttcaacaaa accggccatg ccttgcgtgc aattggccgc    660
ctgtccagcg gaggctctgg cggttccggc ggttcaggtg atcagacca gctgaccgag     720
gagcaaattg cagaatttaa ggaggcgttc tctttgtttg acaaagatgg cgacggtaca    780
attacaacca aggaattggg cacagtaatg cgctcccttg acagaatcc cactgaagcc     840
gaacttcaag acatgatcaa tgaggttgat gctgacgggg atgggactat cgactttcct    900
gagtttctta ccatgatggc tcgcaaaatg aaggatacag acagtgagga ggaaattcgt    960
gaggccttc gtgtgtttga taaggacggg aacggttata tctcagcggc ggagctgcgt   1020
cacgttatga ccaacttagg cgaaaagctg actgatgaag aagtcgatga tgatgatccgc  1080
gaggcggaca tcgatggtga tggtcaagtc aattatgaag agtttgtggt gatgatgacc   1140
gcgaagtgcc tcttcagaac tacttacaaa gctaaggaga agggtgtcaa gttaccaggc   1200
gtgcactatg tggaccacac cattgagatt ttaagccatg acaaagatta caacaaggtt   1260
aagatctatg agtatgctgt tgctcattct ggattgcctg acaatgccag acgaggaggt   1320
agcgtgtcta agggcgaaga gctgatcaag gaaaatatgc gtatgaaggt ggtcatggaa   1380
ggttcggtca acggccacca attcaaatgc acaggtgaag gagaaggcag accgtacgag   1440
ggagtgcaaa ccatgaggat caaagtcatc gagggaggac ccctgccatt tgcctttgac   1500
attcttgcca cgtcgttcat gtatggcagc cgtaccttta tcaagtaccc ggccgacatc   1560
cctgatttct ttaaacagtc ctttcctgag ggttttactt gggaaagagt tacgagatac   1620
gaagatggtg gagtcgtcac cgtcacgcag gacaccagcc ttgaggatgg cgagctcgtc   1680
tacaacgtca aggtcagagg ggtaaacttt ccctccaatg gtcccgtgat gcagaagaag   1740
accaagggtt gggagcctaa tacagagatg atgtatccag cagatggtgg tctgagagga   1800
tacactgaca tcgcactgaa agttgatggt ggtggccatc tgcactgcaa cttcgtgaca   1860
acttacaggt caaaaaagac cgtcgggaac atcaagatgc ccggtgtcca tgccgttgat   1920
caccgcctgg aaaggatcga ggagagtgac aatgaaacct acgtagtgca aagagaagtg   1980
gcagttgcca aatacagcaa ccttggtggt ggcatggacg agctgtacaa g            2031
```

<210> SEQ ID NO 24
<211> LENGTH: 677
<212> TYPE: PRT
<213> ORGANISM: Artificial Sequence
<220> FEATURE:
<223> OTHER INFORMATION: Synthetic

<400> SEQUENCE: 24

```
Met Leu Gln Asn Glu Leu Ala Leu Lys Leu Ala Gly Leu Asp Ile Asn
1               5                   10                  15

Lys Thr Gly Gly Ser His His His His His His Gly Ser Met Val Ser
            20                  25                  30

Ala Ile Lys Pro Asp Met Lys Ile Lys Leu Arg Met Glu Gly Asn Val
        35                  40                  45

Asn Gly His His Phe Val Ile Asp Gly Asp Gly Thr Gly Lys Pro Tyr
    50                  55                  60

Glu Gly Lys Gln Thr Met Asp Leu Glu Val Lys Glu Gly Gly Pro Leu
65                  70                  75                  80

Pro Phe Ala Phe Asp Ile Leu Thr Thr Ala Phe Leu Tyr Gly Asn Arg
                85                  90                  95
```

```
Val Phe Val Lys Tyr Pro Asp Asn Ile Gln Asp Tyr Phe Lys Gln Ser
             100                 105                 110

Phe Pro Lys Gly Tyr Ser Trp Glu Arg Ser Met Thr Phe Glu Asp Gly
        115                 120                 125

Gly Ile Cys Tyr Ala Arg Ser Asp Ile Thr Met Glu Gly Asp Thr Phe
    130                 135                 140

Tyr Asn Lys Val Arg Phe Tyr Gly Thr Asn Phe Pro Ala Asn Gly Pro
145                 150                 155                 160

Val Met Gln Lys Lys Thr Leu Lys Trp Glu Pro Ser Thr Glu Lys Met
                165                 170                 175

Tyr Val Arg Asp Gly Val Leu Thr Gly Asp Val Glu Met Ala Leu Leu
            180                 185                 190

Leu Glu Gly Asn Ala His Tyr Arg Ala Leu Ser Ser Arg Arg Lys Phe
        195                 200                 205

Asn Lys Thr Gly His Ala Leu Arg Ala Ile Gly Arg Leu Ser Ser Gly
    210                 215                 220

Gly Ser Gly Gly Ser Gly Gly Ser Gly Gly Ser Asp Gln Leu Thr Glu
225                 230                 235                 240

Glu Gln Ile Ala Glu Phe Lys Glu Ala Phe Ser Leu Phe Asp Lys Asp
                245                 250                 255

Gly Asp Gly Thr Ile Thr Thr Lys Glu Leu Gly Thr Val Met Arg Ser
            260                 265                 270

Leu Gly Gln Asn Pro Thr Glu Ala Glu Leu Gln Asp Met Ile Asn Glu
        275                 280                 285

Val Asp Ala Asp Gly Asp Gly Thr Ile Asp Phe Pro Glu Phe Leu Thr
    290                 295                 300

Met Met Ala Arg Lys Met Lys Asp Thr Asp Ser Glu Glu Glu Ile Arg
305                 310                 315                 320

Glu Ala Phe Arg Val Phe Asp Lys Asp Gly Asn Gly Tyr Ile Ser Ala
                325                 330                 335

Ala Glu Leu Arg His Val Met Thr Asn Leu Gly Glu Lys Leu Thr Asp
            340                 345                 350

Glu Glu Val Asp Glu Met Ile Arg Glu Ala Asp Ile Asp Gly Asp Gly
        355                 360                 365

Gln Val Asn Tyr Glu Glu Phe Val Val Met Met Thr Ala Lys Cys Leu
    370                 375                 380

Phe Arg Thr Thr Tyr Lys Ala Lys Glu Lys Gly Val Lys Leu Pro Gly
385                 390                 395                 400

Val His Tyr Val Asp His Thr Ile Glu Ile Leu Ser His Asp Lys Asp
                405                 410                 415

Tyr Asn Lys Val Lys Ile Tyr Glu Tyr Ala Val Ala His Ser Gly Leu
            420                 425                 430

Pro Asp Asn Ala Arg Arg Gly Gly Ser Val Ser Lys Gly Glu Glu Leu
        435                 440                 445

Ile Lys Glu Asn Met Arg Met Lys Val Val Met Glu Gly Ser Val Asn
    450                 455                 460

Gly His Gln Phe Lys Cys Thr Gly Glu Gly Glu Gly Arg Pro Tyr Glu
465                 470                 475                 480

Gly Val Gln Thr Met Arg Ile Lys Val Ile Glu Gly Gly Pro Leu Pro
                485                 490                 495

Phe Ala Phe Asp Ile Leu Ala Thr Ser Phe Met Tyr Gly Ser Arg Thr
            500                 505                 510

Phe Ile Lys Tyr Pro Ala Asp Ile Pro Asp Phe Phe Lys Gln Ser Phe
```

```
                515                 520                 525
Pro Glu Gly Phe Thr Trp Glu Arg Val Thr Arg Tyr Glu Asp Gly Gly
        530                 535                 540

Val Val Thr Val Thr Gln Asp Thr Ser Leu Glu Asp Gly Glu Leu Val
545                 550                 555                 560

Tyr Asn Val Lys Val Arg Gly Val Asn Phe Pro Ser Asn Gly Pro Val
                565                 570                 575

Met Gln Lys Lys Thr Lys Gly Trp Glu Pro Asn Thr Glu Met Met Tyr
        580                 585                 590

Pro Ala Asp Gly Gly Leu Arg Gly Tyr Thr Asp Ile Ala Leu Lys Val
            595                 600                 605

Asp Gly Gly His Leu His Cys Asn Phe Val Thr Thr Tyr Arg Ser
        610                 615                 620

Lys Lys Thr Val Gly Asn Ile Lys Met Pro Gly Val His Ala Val Asp
625                 630                 635                 640

His Arg Leu Glu Arg Ile Glu Glu Ser Asp Asn Glu Thr Tyr Val Val
                645                 650                 655

Gln Arg Glu Val Ala Val Ala Lys Tyr Ser Asn Leu Gly Gly Gly Met
        660                 665                 670

Asp Glu Leu Tyr Lys
        675

<210> SEQ ID NO 25
<211> LENGTH: 1227
<212> TYPE: DNA
<213> ORGANISM: Artificial Sequence
<220> FEATURE:
<223> OTHER INFORMATION: Synthetic

<400> SEQUENCE: 25
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacggggc      300
atttgctatg ccagaagcga cataacaatg aaggggaca cttctctataa aaagttcga     360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgagcgacgt caagccgccg caagttcaac     540
aaaaccggcc atgccttgcg tgcaattggc cgcctgtcca gcggaggctc tggcggttcc     600
ggcggttcag gtggatcaga ccagctgacc gaggagcaaa ttgcagaatt taaggaggcg     660
ttctctttgt ttgacaaaga tggcgacggt acaattacaa ccaaggaatt gggcacagta     720
atgcgctccc ttggacagaa tcccactgaa gccgaacttc aagacatgat caatgaggtt     780
gatgctgacg gggatgggac tatcgacttt cctgagtttc ttaccatgat ggctcgcaaa     840
atgaaggata cagacagtga ggaggaaatt cgtgaggcct tcgtgtgtt tgataaggac     900
gggaacggtt atatctcagc ggcggagctg cgtcacgtta tgaccaactt aggcgaaaag     960
ctgactgatg aagaagtcga tgagatgatc cgcgaggcgg acatcgatgg tgatggtcaa    1020
gtcaattatg aagagtttgt ggtgatgatg accgcgaagt gcatcttcag aactacttac    1080
aaagctaagg agaagggtgt caagttacca ggcgtgcact atgtggacca ccaccattgag   1140
```

-continued

```
attttaagcc atgacaaaga ttacaacaag gttaagatct atgagtatgc tgttgctcat    1200
tctggattgc ctgacaatgc cagacga                                        1227
```

<210> SEQ ID NO 26
<211> LENGTH: 409
<212> TYPE: PRT
<213> ORGANISM: Artificial Sequence
<220> FEATURE:
<223> OTHER INFORMATION: Synthetic

<400> SEQUENCE: 26

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
                100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Ala Thr Ser Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
            260                 265                 270

Phe Leu Thr Met Met Ala Arg Lys Met Lys Asp Thr Asp Ser Glu Glu
        275                 280                 285

Glu Ile Arg Glu Ala Phe Arg Val Phe Asp Lys Asp Gly Asn Gly Tyr
    290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala

Lys Cys Ile Phe Arg Thr Thr Tyr Lys Ala Lys Glu Lys Gly Val Lys
         340             345                 350
                 355                 360                 365

Leu Pro Gly Val His Tyr Val Asp His Thr Ile Glu Ile Leu Ser His
        370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
            405

<210> SEQ ID NO 27
<211> LENGTH: 1233
<212> TYPE: DNA
<213> ORGANISM: Artificial Sequence
<220> FEATURE:
<223> OTHER INFORMATION: Synthetic

<400> SEQUENCE: 27

| | | | | | |
|---|---|---|---|---|---|
| atggtgagtg | cgattaagcc | agacatgaag | atcaaactgc | gtatggaagg | caacgtaaac | 60 |
| gggcaccact | ttgtgatcga | cggagatggt | acaggcaagc | cttatgaggg | aaaacagacc | 120 |
| atggatcttg | aagtcaaaga | gggcggacct | ctgccttttg | cctttgatat | cctgaccact | 180 |
| gcattcctgt | acggcaacag | ggtattcgtg | aaatatccag | acaacataca | agactatttt | 240 |
| aagcagtcgt | ttcctaaggg | gtattcgtgg | aacgaagca | tgactttcga | agacggggc | 300 |
| atttgctatg | ccagaagcga | cataacaatg | aaggggaca | cttctataa | taaagttcga | 360 |
| ttttatggta | ccaactttcc | cgccaatggt | ccagttatgc | agaagaagac | gctgaaatgg | 420 |
| gagccctcca | ctgagaaaat | gtatgtgcgt | gatggagtgc | tgacgggtga | tgtagagatg | 480 |
| gctttgttgc | ttgaaggaaa | tgcccattac | cgatgtttga | agtcaagccg | ccgcaagttc | 540 |
| aacaaaaccg | ccatgccctt | gcgtgcaatt | ggccgcctgt | ccagcggagg | ctctggcggt | 600 |
| tccggcggtt | caggtggatc | agaccagctg | accgaggagc | aaattgcaga | atttaaggag | 660 |
| gcgttctctt | tgtttgacaa | agatggcgac | ggtacaatta | caaccaagga | attgggcaca | 720 |
| gtaatgcgct | cccttggaca | gaatcccact | gaagccgaac | ttcaagacat | gatcaatgag | 780 |
| gttgatgctg | acggggatgg | gactatcgac | tttcctgagt | ttcttaccat | gatggctcgc | 840 |
| aaaatgaagg | atacagacag | tgaggaggaa | attcgtgagg | cctttcgtgt | gtttgataag | 900 |
| gacgggaacg | gttatatctc | agcggcggag | ctgcgtcacg | ttatgaccaa | cttaggcgaa | 960 |
| aagctgactg | atgaagaagt | cgatgagatg | atccgcgagg | cggacatcga | tggtgatggt | 1020 |
| caagtcaatt | atgaagagtt | tgtggtgatg | atgaccgcga | agggcatgga | cttcagaact | 1080 |
| acttacaaag | ctaaggagaa | gggtgtcaag | ttaccaggcg | tgcactatgt | ggaccacacc | 1140 |
| attgagattt | taagccatga | caaagattac | aacaaggtta | agatctatga | gtatgctgtt | 1200 |
| gctcattctg | gattgcctga | caatgccaga | cga | | | 1233 |

<210> SEQ ID NO 28
<211> LENGTH: 411
<212> TYPE: PRT
<213> ORGANISM: Artificial Sequence
<220> FEATURE:
<223> OTHER INFORMATION: Synthetic

<400> SEQUENCE: 28

Met Val Ser Ala Ile Lys Pro Asp Met Lys Ile Lys Leu Arg Met Glu
1               5                   10                  15

-continued

Gly Asn Val Asn Gly His His Phe Val Ile Asp Gly Asp Thr Gly
            20                  25                  30
Lys Pro Tyr Glu Gly Lys Gln Thr Met Asp Leu Glu Val Lys Glu Gly
         35                  40                  45
Gly Pro Leu Pro Phe Ala Phe Asp Ile Leu Thr Thr Ala Phe Leu Tyr
 50                  55                  60
Gly Asn Arg Val Phe Val Lys Tyr Pro Asp Asn Ile Gln Asp Tyr Phe
 65                  70                  75                  80
Lys Gln Ser Phe Pro Lys Gly Tyr Ser Trp Glu Arg Ser Met Thr Phe
                 85                  90                  95
Glu Asp Gly Gly Ile Cys Tyr Ala Arg Ser Asp Ile Thr Met Glu Gly
            100                 105                 110
Asp Thr Phe Tyr Asn Lys Val Arg Phe Tyr Gly Thr Asn Phe Pro Ala
        115                 120                 125
Asn Gly Pro Val Met Gln Lys Lys Thr Leu Lys Trp Glu Pro Ser Thr
130                 135                 140
Glu Lys Met Tyr Val Arg Asp Gly Val Leu Thr Gly Asp Val Glu Met
145                 150                 155                 160
Ala Leu Leu Leu Glu Gly Asn Ala His Tyr Arg Cys Leu Lys Ser Ser
                165                 170                 175
Arg Arg Lys Phe Asn Lys Thr Gly His Ala Leu Arg Ala Ile Gly Arg
            180                 185                 190
Leu Ser Ser Gly Gly Ser Gly Ser Gly Ser Gly Ser Gly Ser Gly Asp
        195                 200                 205
Gln Leu Thr Glu Glu Gln Ile Ala Glu Phe Lys Glu Ala Phe Ser Leu
210                 215                 220
Phe Asp Lys Asp Gly Asp Gly Thr Ile Thr Thr Lys Glu Leu Gly Thr
225                 230                 235                 240
Val Met Arg Ser Leu Gly Gln Asn Pro Thr Glu Ala Glu Leu Gln Asp
                245                 250                 255
Met Ile Asn Glu Val Asp Ala Asp Gly Asp Gly Thr Ile Asp Phe Pro
            260                 265                 270
Glu Phe Leu Thr Met Met Ala Arg Lys Met Lys Asp Thr Asp Ser Glu
        275                 280                 285
Glu Glu Ile Arg Glu Ala Phe Arg Val Phe Asp Lys Asp Gly Asn Gly
290                 295                 300
Tyr Ile Ser Ala Ala Glu Leu Arg His Val Met Thr Asn Leu Gly Glu
305                 310                 315                 320
Lys Leu Thr Asp Glu Glu Val Asp Glu Met Ile Arg Glu Ala Asp Ile
                325                 330                 335
Asp Gly Asp Gly Gln Val Asn Tyr Glu Glu Phe Val Val Met Met Thr
            340                 345                 350
Ala Lys Gly Met Asp Phe Arg Thr Thr Tyr Lys Ala Lys Glu Lys Gly
        355                 360                 365
Val Lys Leu Pro Gly Val His Tyr Val Asp His Thr Ile Glu Ile Leu
370                 375                 380
Ser His Asp Lys Asp Tyr Asn Lys Val Lys Ile Tyr Glu Tyr Ala Val
385                 390                 395                 400
Ala His Ser Gly Leu Pro Asp Asn Ala Arg Arg
                405                 410

<210> SEQ ID NO 29
<211> LENGTH: 1227
<212> TYPE: DNA

<213> ORGANISM: Artificial Sequence
<220> FEATURE:
<223> OTHER INFORMATION: Synthetic

<400> SEQUENCE: 29

```
atggtgagtg cgattaagcc agacatgaag atcaaactgc gtatggaagg caacgtaaac      60
gggcaccact ttgtgatcga cggagatggt acaggcaagc ttatgaggg aaaacagacc      120
atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga agacggggc       300
atttgctatg ccagaagcga cataacaatg aaggggaca ctttctataa taaagttcga      360
ttttatggta ccaactttcc cgccaatggt ccagttatgc agaagaagac gctgaaatgg      420
gagccctcca ctgagaaaat gtatgtgcgt gatggagtgc tgacgggtga tgtagagatg      480
gctttgttgc ttgaaggaaa tgcccattac cgacgcgagt caagccgccg caagttcaac      540
aaaaccggcc atgccttgcg tgcaattggc cgcctgtcca gcggaggctc tggcggttcc      600
ggcggttcag gtggatcaga ccagctgacc gaggagcaaa ttgcagaatt taaggaggcg      660
ttctctttgt ttgacaaaga tggcgacggt acaattacaa ccaaggaatt gggcacagta      720
atgcgctccc ttggacagaa tcccactgaa gccgaacttc aagacatgat caatgaggtt      780
gatgctgacg gggatgggac tatcgacttt cctgagtttc ttaccatgat ggctcgcaaa      840
atgaaggata cagacagtga ggaggaaatt cgtgaggcct tcgtgtgtt tgataaggac      900
gggaacggtt atatctcagc ggcggagctg cgtcacgtta tgaccaactt aggcgaaaag      960
ctgactgatg aagaagtcga tgagatgatc cgcgaggcgg acatcgatgg tgatggtcaa     1020
gtcaattatg aagagtttgt ggtgatgatg accgcgaagg tcaccttcag aactacttac     1080
aaagctaagg agaagggtgt caagttacca ggcgtgcact atgtggacca ccaccattgag     1140
attttaagcc atgacaaaga ttacaacaag gttaagatct atgagtatgc tgttgctcat     1200
tctggattgc ctgacaatgc cagacga                                        1227
```

<210> SEQ ID NO 30
<211> LENGTH: 409
<212> TYPE: PRT
<213> ORGANISM: Artificial Sequence
<220> FEATURE:
<223> OTHER INFORMATION: Synthetic

<400> SEQUENCE: 30

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110
```

```
Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
        130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Arg Glu Ser Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
            260                 265                 270

Phe Leu Thr Met Met Ala Arg Lys Met Lys Asp Thr Asp Ser Glu Glu
        275                 280                 285

Glu Ile Arg Glu Ala Phe Arg Val Phe Asp Lys Asp Gly Asn Gly Tyr
    290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
            340                 345                 350

Lys Val Thr Phe Arg Thr Thr Tyr Lys Ala Lys Glu Lys Gly Val Lys
        355                 360                 365

Leu Pro Gly Val His Tyr Val Asp His Thr Ile Glu Ile Leu Ser His
    370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 31
<211> LENGTH: 1233
<212> TYPE: DNA
<213> ORGANISM: Artificial Sequence
<220> FEATURE:
<223> OTHER INFORMATION: Synthetic

<400> SEQUENCE: 31
atggtgagtg cgattaagcc agacatgaag atcaaactgc gtatggaagg caacgtaaac      60
gggcaccact tgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacgggggc     300
atttgctatg ccagaagcga cataacaatg gaaggggaca ctttctataa taagttcga     360
```

```
ttttatggta ccaactttcc cgccaatggt ccagttatgc agaagaagac gctgaaatgg      420
gagccctcca ctgagaaaat gtatgtgcgt gatggagtgc tgacgggtga tgtagagatg      480
gctttgttgc ttgaaggaaa tgcccattac cgatgtttga agtcaagccg ccgcaagttc      540
aacaaaaccg gccatgcctt gcgtgcaatt ggccgcctgt ccagcggagg ctctggcggt      600
tccggcggtt caggtggatc agaccagctg accgaggagc aaattgcaga atttaaggag      660
gcgttctctt tgtttgacaa agatggcgac ggtacaatta caaccaagga attgggcaca      720
gtaatgcgct cccttggaca gaatcccact gaagccgaac ttcaagacat gatcaatgag      780
gttgatgctg acggggatgg gactatcgac tttcctgagt tcttaccat gatggctcgc       840 aaaatgaagg atacagacag tgaggaggaa attcgtgagg cctttcgtgt gtttgataag      900
gacgggaacg gttatatctc agcggcggag ctgcgtcacg ttatgaccaa cttaggcgaa      960
aagctgactg atgaagaagt cgatgagatg atccgcgagg cggacatcga tggtgatggt     1020
caagtcaatt atgaagagtt tgtggtgatg atgaccgcga aggcgtccga cttcagaact     1080
acttacaaag ctaaggagaa gggtgtcaag ttaccaggcg tgcactatgt ggaccacacc     1140
attgagattt taagccatga caaagattac aacaaggtta agatctatga gtatgctgtt     1200
gctcattctg gattgcctga caatgccaga cga                                  1233
```

<210> SEQ ID NO 32
<211> LENGTH: 411
<212> TYPE: PRT
<213> ORGANISM: Artificial Sequence
<220> FEATURE:
<223> OTHER INFORMATION: Synthetic

<400> SEQUENCE: 32

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Leu Lys Ser Ser
                165                 170                 175

Arg Arg Lys Phe Asn Lys Thr Gly His Ala Leu Arg Ala Ile Gly Arg
            180                 185                 190

Leu Ser Ser Gly Gly Ser Gly Gly Ser Gly Gly Ser Gly Gly Ser Asp
        195                 200                 205
```

```
Gln Leu Thr Glu Glu Gln Ile Ala Glu Phe Lys Glu Ala Phe Ser Leu
        210                 215                 220
Phe Asp Lys Asp Gly Asp Gly Thr Ile Thr Thr Lys Glu Leu Gly Thr
225                 230                 235                 240
Val Met Arg Ser Leu Gly Gln Asn Pro Thr Glu Ala Glu Leu Gln Asp
                245                 250                 255
Met Ile Asn Glu Val Asp Ala Asp Gly Asp Gly Thr Ile Asp Phe Pro
            260                 265                 270
Glu Phe Leu Thr Met Met Ala Arg Lys Met Lys Asp Thr Asp Ser Glu
        275                 280                 285
Glu Glu Ile Arg Glu Ala Phe Arg Val Phe Asp Lys Asp Gly Asn Gly
    290                 295                 300
Tyr Ile Ser Ala Ala Glu Leu Arg His Val Met Thr Asn Leu Gly Glu
305                 310                 315                 320
Lys Leu Thr Asp Glu Glu Val Asp Glu Met Ile Arg Glu Ala Asp Ile
                325                 330                 335
Asp Gly Asp Gly Gln Val Asn Tyr Glu Glu Phe Val Val Met Met Thr
            340                 345                 350
Ala Lys Ala Ser Asp Phe Arg Thr Thr Tyr Lys Ala Lys Glu Lys Gly
        355                 360                 365
Val Lys Leu Pro Gly Val His Tyr Val Asp His Thr Ile Glu Ile Leu
    370                 375                 380
Ser His Asp Lys Asp Tyr Asn Lys Val Lys Ile Tyr Glu Tyr Ala Val
385                 390                 395                 400
Ala His Ser Gly Leu Pro Asp Asn Ala Arg Arg
                405                 410

<210> SEQ ID NO 33
<211> LENGTH: 1224
<212> TYPE: DNA
<213> ORGANISM: Artificial Sequence
<220> FEATURE:
<223> OTHER INFORMATION: Synthetic

<400> SEQUENCE: 33
atggtgagtg cgattaagcc agacatgaag atcaaactgc gtatggaagg caacgtaaac      60
gggcaccact tgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga gacgggggc     300 atttgctatg ccagaagcga cataacaatg aaggggaca cttctataa taaagttcga     360 ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgatgtaagg actcaagccg ccgcaagttc     540
aacaaaaccg gccatgcctt gcgtgcaatt ggccgcctgt ccagcggagg ctctggcggt     600
tccggcggtt caggtggatc agaccagctg accgaggagc aaattgcaga atttaaggag     660
gcgttctctt tgtttgacaa agatggcgac ggtacaatta caaccaagga attgggcaca     720
gtaatgcgct cccttggaca gaatcccact gaagccgaac ttcaagacat gatcaatgag     780
gttgatgctg acggggatgg gactatcgac tttcctgagt tcttaccat gatggctcgc     840 aaaatgaagg atacagacag tgaggaggaa attcgtgagg cctttcgtgt gtttgataag     900
```

```
gacgggaacg gttatatctc agcggcggag ctgcgtcacg ttatgaccaa cttaggcgaa    960
aagctgactg atgaagaagt cgatgagatg atccgcgagg cggacatcga tggtgatggt   1020
caagtcaatt atgaagagtt tgtggtgatg atgaccgcga agatgcgcac tacttacaaa   1080
gctaaggaga agggtgtcaa gttaccaggc gtgcactatg tggaccacac cattgagatt   1140
ttaagccatg acaagattaa caacaaggtt aagatctatg agtatgctgt tgctcattct   1200
ggattgcctg acaatgccag acga                                          1224

<210> SEQ ID NO 34
<211> LENGTH: 408
<212> TYPE: PRT
<213> ORGANISM: Artificial Sequence
<220> FEATURE:
<223> OTHER INFORMATION: Synthetic

<400> SEQUENCE: 34

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Cys Lys Asp Ser Ser
                165                 170                 175

Arg Arg Lys Phe Asn Lys Thr Gly His Ala Leu Arg Ala Ile Gly Arg
            180                 185                 190

Leu Ser Ser Gly Gly Ser Gly Gly Ser Gly Gly Ser Gly Gly Ser Asp
        195                 200                 205

Gln Leu Thr Glu Glu Gln Ile Ala Glu Phe Lys Glu Ala Phe Ser Leu
    210                 215                 220

Phe Asp Lys Asp Gly Asp Gly Thr Ile Thr Thr Lys Glu Leu Gly Thr
225                 230                 235                 240

Val Met Arg Ser Leu Gly Gln Asn Pro Thr Glu Ala Glu Leu Gln Asp
                245                 250                 255

Met Ile Asn Glu Val Asp Ala Asp Gly Asp Gly Thr Ile Asp Phe Pro
            260                 265                 270

Glu Phe Leu Thr Met Met Ala Arg Lys Met Lys Asp Thr Asp Ser Glu
        275                 280                 285

Glu Glu Ile Arg Glu Ala Phe Arg Val Phe Asp Lys Asp Gly Asn Gly
    290                 295                 300
```

Tyr Ile Ser Ala Ala Glu Leu Arg His Val Met Thr Asn Leu Gly Glu
305                 310                 315                 320

Lys Leu Thr Asp Glu Glu Val Asp Glu Met Ile Arg Glu Ala Asp Ile
            325                 330                 335

Asp Gly Asp Gly Gln Val Asn Tyr Glu Glu Phe Val Val Met Met Thr
            340                 345                 350

Ala Lys Met Arg Thr Thr Tyr Lys Ala Lys Glu Lys Gly Val Lys Leu
        355                 360                 365

Pro Gly Val His Tyr Val Asp His Thr Ile Glu Ile Leu Ser His Asp
        370                 375                 380

Lys Asp Tyr Asn Lys Val Lys Ile Tyr Glu Tyr Ala Val Ala His Ser
385                 390                 395                 400

Gly Leu Pro Asp Asn Ala Arg Arg
                405

<210> SEQ ID NO 35
<211> LENGTH: 1227
<212> TYPE: DNA
<213> ORGANISM: Artificial Sequence
<220> FEATURE:
<223> OTHER INFORMATION: Synthetic

<400> SEQUENCE: 35
atggtgagtg cgattaagcc agacatgaag atcaaactgc gtatggaagg caacgtaaac      60
gggcaccact ttgtgatcga cggagatggt acaggcaagc ttatgaggg aaaacagacc      120 atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga agacgggggc       300
atttgctatg ccagaagcga cataacaatg aaggggaca ctttctataa taagttcga      360 ttttatggta ccaactttcc cgccaatggt ccagttatgc agaagaagac gctgaaatgg      420
gagccctcca ctgagaaaat gtatgtgcgt gatgagtgc tgacgggtga tgtagagatg      480
gctttgttgc ttgaaggaaa tgcccattac cgacggggt caagccgccg caagttcaac      540
aaaaccggcc atgccttgcg tgcaattggc cgcctgtcca gcggaggctc tggcggttcc      600
ggcggttcag gtggatcaga ccagctgacc gaggagcaaa ttgcagaatt taaggaggcg      660
ttctctcttt gt ttgacaaaga tggcgacggt acaattacaa ccaaggaatt gggcacagta      720
atgcgctccc ttggacagaa tcccactgaa gccgaacttc aagacatgat caatgaggtt      780
gatgctgacg ggatgggac tatcgacttt cctgagtttc ttaccatgat ggctcgcaaa      840
atgaaggata cagacagtga ggaggaaatt cgtgaggcct tcgtgtgtt tgataaggac      900 gggaacggtt atatctcagc ggcggagctg cgtcacgtta tgaccaactt aggcgaaaag      960
ctgactgatg aagaagtcga tgagatgatc cgcgaggcgg acatcgatgg tgatggtcaa     1020
gtcaattatg aagagtttgt ggtgatgatg accgcgaagg ccttcttcag aactacttac     1080
aaagctaagg agaagggtgt caagttacca ggcgtgcact atgtggacca ccaccattgag    1140 atttaagcc atgacaaaga ttacaacaag gttaagatct atgagtatgc tgttgctcat     1200
tctggattgc ctgacaatgc cagacga                                            1227

<210> SEQ ID NO 36
<211> LENGTH: 409
<212> TYPE: PRT
<213> ORGANISM: Artificial Sequence
<220> FEATURE:

<223> OTHER INFORMATION: Synthetic

<400> SEQUENCE: 36

Met Val Ser Ala Ile Lys Pro Asp Met Lys Ile Lys Leu Arg Met Glu
1               5                   10                  15
Gly Asn Val Asn Gly His His Phe Val Ile Asp Gly Asp Gly Thr Gly
            20                  25                  30
Lys Pro Tyr Glu Gly Lys Gln Thr Met Asp Leu Glu Val Lys Glu Gly
        35                  40                  45
Gly Pro Leu Pro Phe Ala Phe Asp Ile Leu Thr Thr Ala Phe Leu Tyr
    50                  55                  60
Gly Asn Arg Val Phe Val Lys Tyr Pro Asp Asn Ile Gln Asp Tyr Phe
65                  70                  75                  80
Lys Gln Ser Phe Pro Lys Gly Tyr Ser Trp Glu Arg Ser Met Thr Phe
                85                  90                  95
Glu Asp Gly Gly Ile Cys Tyr Ala Arg Ser Asp Ile Thr Met Glu Gly
            100                 105                 110
Asp Thr Phe Tyr Asn Lys Val Arg Phe Tyr Gly Thr Asn Phe Pro Ala
        115                 120                 125
Asn Gly Pro Val Met Gln Lys Lys Thr Leu Lys Trp Glu Pro Ser Thr
    130                 135                 140
Glu Lys Met Tyr Val Arg Asp Gly Val Leu Thr Gly Asp Val Glu Met
145                 150                 155                 160
Ala Leu Leu Leu Glu Gly Asn Ala His Tyr Arg Arg Gly Ser Ser Arg
                165                 170                 175
Arg Lys Phe Asn Lys Thr Gly His Ala Leu Arg Ala Ile Gly Arg Leu
            180                 185                 190
Ser Ser Gly Gly Ser Gly Gly Ser Gly Gly Ser Asp Gln
        195                 200                 205
Leu Thr Glu Glu Gln Ile Ala Glu Phe Lys Glu Ala Phe Ser Leu Phe
    210                 215                 220
Asp Lys Asp Gly Asp Gly Thr Ile Thr Thr Lys Glu Leu Gly Thr Val
225                 230                 235                 240
Met Arg Ser Leu Gly Gln Asn Pro Thr Glu Ala Glu Leu Gln Asp Met
                245                 250                 255
Ile Asn Glu Val Asp Ala Asp Gly Asp Gly Thr Ile Asp Phe Pro Glu
            260                 265                 270
Phe Leu Thr Met Met Ala Arg Lys Met Lys Asp Thr Asp Ser Glu Glu
        275                 280                 285
Glu Ile Arg Glu Ala Phe Arg Val Phe Asp Lys Asp Gly Asn Gly Tyr
    290                 295                 300
Ile Ser Ala Ala Glu Leu Arg His Val Met Thr Asn Leu Gly Glu Lys
305                 310                 315                 320
Leu Thr Asp Glu Glu Val Asp Glu Met Ile Arg Glu Ala Asp Ile Asp
                325                 330                 335
Gly Asp Gly Gln Val Asn Tyr Glu Glu Phe Val Val Met Met Thr Ala
            340                 345                 350
Lys Ala Phe Phe Arg Thr Thr Tyr Lys Ala Lys Glu Lys Gly Val Lys
        355                 360                 365
Leu Pro Gly Val His Tyr Val Asp His Thr Ile Glu Ile Leu Ser His
    370                 375                 380
Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 37
<211> LENGTH: 1233
<212> TYPE: DNA
<213> ORGANISM: Artificial Sequence
<220> FEATURE:
<223> OTHER INFORMATION: Synthetic

<400> SEQUENCE: 37

```
atggtgagtg cgattaagcc agacatgaag atcaaactgc gtatggaagg caacgtaaac     60
gggcaccact ttgtgatcga cggagatggt acaggcaagc ttatgaggg aaaacagacc    120
atggatcttg aagtcaaaga gggcggacct ctgccttttg cctttgatat cctgaccact    180
gcattcctgt acggcaacag ggtattcgtg aaatatccag acaacataca agactatttt    240
aagcagtcgt ttcctaaggg gtattcgtgg aacgaagca tgactttcga agacggggc    300
atttgctatg ccagaagcga cataacaatg aaggggaca ctttctataa taagttcga    360
ttttatggta ccaactttcc cgccaatggt ccagttatgc agaagaagac gctgaaatgg    420
gagccctcca ctgagaaaat gtatgtgcgt gatggagtgc tgacgggtga tgtagagatg    480
gctttgttgc ttgaaggaaa tgcccattac cgatgtgacg acgtgtcaag ccgccgcaag    540
ttcaacaaaa ccggccatgc cttgcgtgca attggccgcc tgtccagcgg aggctctggc    600
ggttccggcg gttcaggtgg atcagaccag ctgaccgagg agcaaattgc agaatttaag    660
gaggcgttct ctttgtttga caaagatggc gacggtacaa ttacaaccaa ggaattgggc    720
acagtaatgc gctcccttgg acagaatccc actgaagccg aacttcaaga catgatcaat    780
gaggttgatg ctgacgggga tgggactatc gactttcctg agtttcttac catgatggct    840
cgcaaaatga aggatacaga cagtgaggag gaaattcgtg aggcctttcg tgtgtttgat    900
aaggacggga acggttatat ctcagcggcg gagctgcgtc acgttatgac caacttaggc    960
gaaaagctga ctgatgaaga agtcgatgag atgatccgcg aggcggacat cgatggtgat   1020
ggtcaagtca attatgaaga gtttgtggtg atgatgaccg cgaaggcgca cttcagaact   1080
acttacaaag ctaaggagaa gggtgtcaag ttaccaggcg tgcactatgt ggaccacacc   1140
attgagattt taagccatga caaagattac aacaaggtta agatctatga gtatgctgtt   1200
gctcattctg gattgcctga caatgccaga cga                                1233
```

<210> SEQ ID NO 38
<211> LENGTH: 411
<212> TYPE: PRT
<213> ORGANISM: Artificial Sequence
<220> FEATURE:
<223> OTHER INFORMATION: Synthetic

<400> SEQUENCE: 38

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

```
Lys Gln Ser Phe Pro Lys Gly Tyr Ser Trp Glu Arg Ser Met Thr Phe
                85                  90                  95
Glu Asp Gly Gly Ile Cys Tyr Ala Arg Ser Asp Ile Thr Met Glu Gly
            100                 105                 110
Asp Thr Phe Tyr Asn Lys Val Arg Phe Tyr Gly Thr Asn Phe Pro Ala
        115                 120                 125
Asn Gly Pro Val Met Gln Lys Lys Thr Leu Lys Trp Glu Pro Ser Thr
    130                 135                 140
Glu Lys Met Tyr Val Arg Asp Gly Val Leu Thr Gly Asp Val Glu Met
145                 150                 155                 160
Ala Leu Leu Leu Glu Gly Asn Ala His Tyr Arg Cys Asp Asp Val Ser
                165                 170                 175
Ser Arg Arg Lys Phe Asn Lys Thr Gly His Ala Leu Arg Ala Ile Gly
            180                 185                 190
Arg Leu Ser Ser Gly Ser Gly Ser Gly Ser Gly Ser Gly Gly Ser
        195                 200                 205
Asp Gln Leu Thr Glu Glu Gln Ile Ala Glu Phe Lys Glu Ala Phe Ser
    210                 215                 220
Leu Phe Asp Lys Asp Gly Asp Gly Thr Ile Thr Thr Lys Glu Leu Gly
225                 230                 235                 240
Thr Val Met Arg Ser Leu Gly Gln Asn Pro Thr Glu Ala Glu Leu Gln
                245                 250                 255
Asp Met Ile Asn Glu Val Asp Ala Asp Gly Asp Gly Thr Ile Asp Phe
            260                 265                 270
Pro Glu Phe Leu Thr Met Met Ala Arg Lys Met Lys Asp Thr Asp Ser
        275                 280                 285
Glu Glu Glu Ile Arg Glu Ala Phe Arg Val Phe Asp Lys Asp Gly Asn
    290                 295                 300
Gly Tyr Ile Ser Ala Ala Glu Leu Arg His Val Met Thr Asn Leu Gly
305                 310                 315                 320
Glu Lys Leu Thr Asp Glu Glu Val Asp Glu Met Ile Arg Glu Ala Asp
                325                 330                 335
Ile Asp Gly Asp Gly Gln Val Asn Tyr Glu Glu Phe Val Val Met Met
            340                 345                 350
Thr Ala Lys Ala His Phe Arg Thr Thr Tyr Lys Ala Lys Glu Lys Gly
        355                 360                 365
Val Lys Leu Pro Gly Val His Tyr Val Asp His Thr Ile Glu Ile Leu
    370                 375                 380
Ser His Asp Lys Asp Tyr Asn Lys Val Lys Ile Tyr Glu Tyr Ala Val
385                 390                 395                 400
Ala His Ser Gly Leu Pro Asp Asn Ala Arg Arg
                405                 410

<210> SEQ ID NO 39
<211> LENGTH: 1227
<212> TYPE: DNA
<213> ORGANISM: Artificial Sequence
<220> FEATURE:
<223> OTHER INFORMATION: Synthetic

<400> SEQUENCE: 39
atggtgagtg cgattaagcc agacatgaag atcaaactgc gtatggaagg caacgtaaac      60
gggcaccact ttgtgatcga cggagatggt acaggcaagc ttatgaggg aaaacagacc     120 atggatcttg aagtcaaaga gggcggacct ctgccttttg cctttgatat cctgaccact     180
```

```
gcattcctgt acggcaacag ggtattcgtg aaatatccag acaacataca agactatttt    240
aagcagtcgt ttcctaaggg gtattcgtgg gaacgaagca tgactttcga agacgggggc    300
atttgctatg ccagaagcga cataacaatg gaaggggaca ctttctataa taaagttcga    360
ttttatggta ccaactttcc cgccaatggt ccagttatgc agaagaagac gctgaaatgg    420
gagccctcca ctgagaaaat gtatgtgcgt gatggagtgc tgacgggtga tgtagagatg    480
gctttgttgc ttgaaggaaa tgcccattac cgagggttgt caagccgccg caagttcaac    540
aaaaccggcc atgccttgcg tgcaattggc cgcctgtcca gcggaggctc tggcggttcc    600
ggcggttcag gtggatcaga ccagctgacc gaggagcaaa ttgcagaatt taaggaggcg    660
ttctctttgt ttgacaaaga tggcgacggt acaattacaa ccaaggaatt gggcacagta    720
atgcgctccc ttggacagaa tcccactgaa gccgaacttc aagacatgat caatgaggtt    780
gatgctgacg gggatgggac tatcgacttt cctgagtttc ttaccatgat ggctcgcaaa    840
atgaaggata cagacagtga ggaggaaatt cgtgaggcct tcgtgtgtt tgataaggac    900 gggaacggtt atatctcagc ggcggagctg cgtcacgtta tgaccaactt aggcgaaaag    960
ctgactgatg aagaagtcga tgagatgatc cgcgaggcgg acatcgatgg tgatggtcaa    1020
gtcaattatg aagagtttgt ggtgatgatg accgcgaagt gcctcttcag aactacttac    1080
aaagctaagg agaagggtgt caagttacca ggcgtgcact atgtggacca caccattgag    1140
attttaagcc atgacaaaga ttacaacaag gttaagatct atgagtatgc tgttgctcat    1200
tctggattgc ctgacaatgc cagacga                                        1227

<210> SEQ ID NO 40
<211> LENGTH: 409
<212> TYPE: PRT
<213> ORGANISM: Artificial Sequence
<220> FEATURE:
<223> OTHER INFORMATION: Synthetic

<400> SEQUENCE: 40

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Gly Leu Ser Ser Arg
                165                 170                 175
```

Arg Lys Phe Asn Lys Thr Gly His Ala Leu Arg Ala Ile Gly Arg Leu
            180                 185                 190

Ser Ser Gly Ser Gly Gly Ser Gly Gly Ser Gly Gly Ser Asp Gln
        195                 200                 205

Leu Thr Glu Glu Gln Ile Ala Glu Phe Lys Ala Phe Ser Leu Phe
210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Leu Gln Asp Met
                245                 250                 255

Ile Asn Glu Val Asp Ala Asp Gly Asp Gly Thr Ile Asp Phe Pro Glu
                260                 265                 270

Phe Leu Thr Met Met Ala Arg Lys Met Lys Asp Thr Asp Ser Glu Glu
                275                 280                 285

Glu Ile Arg Glu Ala Phe Arg Val Phe Asp Lys Asp Gly Asn Gly Tyr
290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
                340                 345                 350

Lys Cys Leu Phe Arg Thr Thr Tyr Lys Ala Lys Glu Lys Gly Val Lys
                355                 360                 365

Leu Pro Gly Val His Tyr Val Asp His Thr Ile Glu Ile Leu Ser His
                370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 41
<211> LENGTH: 1227
<212> TYPE: DNA
<213> ORGANISM: Artificial Sequence
<220> FEATURE:
<223> OTHER INFORMATION: Synthetic

<400> SEQUENCE: 41
atggtgagtg cgattaagcc agacatgaag atcaaactgc gtatggaagg caacgtaaac      60
gggcaccact ttgtgatcga cggagatggt acaggcaagc ttatgaggg aaaacagacc      120
atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga agacgggggc      300
atttgctatg ccagaagcga cataacaatg aaggggaca cttctataa taagtcga      360
ttttatggta ccaactttcc cgccaatggt ccagttatgc agaagaagac gctgaaatgg      420
cagccctcca ctgagaaaat gtatgtgcgt gatggagtgc tgacgggtga tgtagagatg      480
gctttgttgc ttgaaggaaa tgccgtttac cgagggctga tcagccgccg caagttcaac      540
aaaaccggcc atgccttgcg tgcaattggc cgcctgtcca gcggaggctc tggcggttcc      600
ggcggttcag gtggatcaga ccagctgacc gaggagcaaa ttgcagaatt taaggaggcg      660
ttctctcttt ttgacaaaga tggcgacggt acaattacaa ccaaggaatt gggcacagta      720

```
atgcgctccc ttggacagaa tcccactgaa gccgaacttc aagacatgat caatgaggtt      780
gatgctgacg gggatgggac tatcgacttt cctgagtttc ttaccatgat ggctcgcaaa      840
atgaaggata cagacagtga ggaggaaatt cgtgaggcct ttcgtgtgtt tgataaggac      900
gggaacggtt atatctcagc ggcggagctg cgtcacgtta tgaccaactt aggcgaaaag      960
ctgactgatg aagaagtcga tgagatgatc cgcgaggcgg acatcgatgg tgatggtcaa     1020
gtcaattatg aagagtttgt ggtgatgatg accgcgaagt gcctcttcag aactacttac     1080
aaagctaagg agaagggtgt caagttacca ggcgtgcact atgtggacca caccattgag     1140
attttaagcc atgacaaaga ttacaacaag gttaagatct atgagtatgc tgttgctcat     1200
tctggattgc ctgacaatgc cagacga                                          1227
```

<210> SEQ ID NO 42
<211> LENGTH: 409
<212> TYPE: PRT
<213> ORGANISM: Artificial Sequence
<220> FEATURE:
<223> OTHER INFORMATION: Synthetic

<400> SEQUENCE: 42

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Gln Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala Val Tyr Arg Gly Leu Ile Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
            260                 265                 270
```

```
Phe Leu Thr Met Met Ala Arg Lys Met Lys Asp Thr Asp Ser Glu Glu
            275                 280                 285

Glu Ile Arg Glu Ala Phe Arg Val Phe Asp Lys Asp Gly Asn Gly Tyr
        290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
            340                 345                 350

Lys Cys Leu Phe Arg Thr Thr Tyr Lys Ala Lys Glu Lys Gly Val Lys
        355                 360                 365

Leu Pro Gly Val His Tyr Val Asp His Thr Ile Glu Ile Leu Ser His
    370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 43
<211> LENGTH: 1227
<212> TYPE: DNA
<213> ORGANISM: Artificial Sequence
<220> FEATURE:
<223> OTHER INFORMATION: Synthetic

<400> SEQUENCE: 43
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacggggc      300 atttgctatg ccagaagcga cataacaatg aaggggaca cttctctataa taaagttcga     360 tttatggta ccaactttcc cgccaatggt ccagttatgc agaagaagac gctgaaatgg     420 cagcccctcca ctgagaaaat gtatgtgcgt gatggagtgc tgacgggtga tgtagagatg     480
gctttgttgc ttgaaggaaa tgccgtttac ggagggggga tcagccgccg caagttcaac     540
aaaaccggcc atgccttgcg tgcaattggc cgcctgtcca gcggaggctc tggcggttcc     600
ggcggttcag gtggatcaga ccagctgacc gaggagcaaa ttgcagaatt aaggaggcg     660 ttctctttgt ttgacaaaga tggcgacggt acaattacaa ccaaggaatt gggcacagta     720
atgcgctccc ttggacagaa tcccactgaa gccgaacttc aagacatgat caatgaggtt     780
gatgctgacg gggatgggac tatcgacttt cctgagtttc ttaccatgat ggctcgcaaa     840
atgaaggata cagacagtga ggaggaaatt cgtgaggcct tcgtgtgttt tgataaggac     900
gggaacggtt atatctcagc ggcggagctg cgtcacgtta tgaccaactt aggcgaaaag     960
ctgactgatg aagaagtcga tgagatgatc cgcgaggcgg acatcgatgg tgatggtcaa    1020
gtcaattatg aagagtttgt ggtgatgatg accgcgaagt gcgtcttcag aactacttac    1080
aaagctaagg agaagggtgt caagttacca ggcgtgcact atgtggacca catcattgag    1140
attttaagcc atgacaaaga ttacaacaag gttaagatct atgagtatgc tgttgctcat    1200
tctggattgc ctgacaatgc cagacga                                         1227
```

<210> SEQ ID NO 44
<211> LENGTH: 409
<212> TYPE: PRT
<213> ORGANISM: Artificial Sequence
<220> FEATURE:
<223> OTHER INFORMATION: Synthetic

<400> SEQUENCE: 44

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Gln Pro Ser Thr
130                 135                 140

Glu Lys Met Tyr Val Arg Asp Gly Val Leu Thr Gly Asp Val Glu Met
145                 150                 155                 160

Ala Leu Leu Leu Glu Gly Asn Ala Val Tyr Gly Gly Ile Ser Arg
                165                 170                 175

Arg Lys Phe Asn Lys Thr Gly His Ala Leu Arg Ala Ile Gly Arg Leu
                180                 185                 190

Ser Ser Gly Gly Ser Gly Gly Ser Gly Gly Ser Gly Ser Asp Gln
            195                 200                 205

Leu Thr Glu Glu Gln Ile Ala Glu Phe Lys Glu Ala Phe Ser Leu Phe
        210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
                260                 265                 270

Phe Leu Thr Met Met Ala Arg Lys Met Lys Asp Thr Asp Ser Glu Glu
        275                 280                 285

Glu Ile Arg Glu Ala Phe Arg Val Phe Asp Lys Asp Gly Asn Gly Tyr
    290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
            340                 345                 350

Lys Cys Val Phe Arg Thr Thr Tyr Lys Ala Lys Glu Lys Gly Val Lys
        355                 360                 365

Leu Pro Gly Val His Tyr Val Asp His Ile Ile Glu Ile Leu Ser His
            370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
            405

<210> SEQ ID NO 45
<211> LENGTH: 1227
<212> TYPE: DNA
<213> ORGANISM: Artificial Sequence
<220> FEATURE:
<223> OTHER INFORMATION: Synthetic

<400> SEQUENCE: 45

```
atggtgagtg cgattaagcc agacatgaag atcaaactgc gtatggaagg caacgtaaac        60
gggcaccact ttgtgatcga cggagatggt acaggcaagc cttatgaggg aaaacagacc       120
atggatcttg aagtcaaaga gggcggacct ctgccttttg cctttgatat cctgaccact       180
gcattcctgt acggcaacag ggtattcgtg aaatatccag acaacataca agactatttt       240
aagcagtcgt ttcctaaggg gtattcgtgg aacgaagca tgactttcga agacgggggc        300
atttgctatg ccagaagcga cataacaatg gaaggggaca ctttctataa taaagttcga       360
ttttatggta ccaactttcc cgccaatggt ccagttatgc agaagaagac gctgaaatgg       420
cagccctcca ctgagaaaat gtatgtgcgt gatggagtgc tgacgggtga tgtagagatg       480
gctttgttgc ttgaaggaaa tgcccattac ggaggggggg tcagccgccg caagttcaac       540
aaaaccggcc atgccttgcg tgcaattggc cgcctgtcca gcggaggctc tggcggttcc       600
ggcggttcag gtggatcaga ccagctgacc gaggagcaaa ttgcagaatt aaggaggcg        660
ttctctttgt tgacaaaga tggcgacggt acaattacaa ccaaggaatt gggcacagta       720
atgcgctccc ttggacagaa tcccactgaa gccgaacttc aagacatgat caatgaggtt       780
gatgctgacg gggatgggac tatcgacttt cctgagtttc ttaccatgat ggctcgcaaa       840
atgaaggata cagacagtga ggaggaaatt cgtgaggcct tcgtgtgtt tgataaggac        900
gggaacggtt atatctcagc ggcggagctg cgtcacgtta tgaccaactt aggcgaaaag       960
ctgactgatg aagaagtcga tgagatgatc cgcgaggcgg acatcgatgg tgatggtcaa      1020
gtcaattatg aagagtttgt ggtgatgatg accgcgaagt gcgtcttcag aactacttac      1080
aaagctaagg agaagggtgt caagttacca ggcgtgcact atgtggacca tcattgag        1140
attttaagcc atgacaaaga ttacaacaag gttaagatct atgagtatgc tgttgctcat      1200
tctggattgc ctgacaatgc cagacga                                          1227
```

<210> SEQ ID NO 46
<211> LENGTH: 409
<212> TYPE: PRT
<213> ORGANISM: Artificial Sequence
<220> FEATURE:
<223> OTHER INFORMATION: Synthetic

<400> SEQUENCE: 46

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly 35                  40                  45

Gly Pro Leu Pro Phe Ala Phe Asp Ile Leu Thr Thr Ala Phe Leu Tyr
 50                  55                  60

Gly Asn Arg Val Phe Val Lys Tyr Pro Asp Asn Ile Gln Asp Tyr Phe
 65                  70                  75                  80

Lys Gln Ser Phe Pro Lys Gly Tyr Ser Trp Glu Arg Ser Met Thr Phe
                 85                  90                  95

Glu Asp Gly Gly Ile Cys Tyr Ala Arg Ser Asp Ile Thr Met Glu Gly
                100                 105                 110

Asp Thr Phe Tyr Asn Lys Val Arg Phe Tyr Gly Thr Asn Phe Pro Ala
                115                 120                 125

Asn Gly Pro Val Met Gln Lys Thr Leu Lys Trp Gln Pro Ser Thr
130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Gly Gly Ile Ser Arg
                165                 170                 175

Arg Lys Phe Asn Lys Thr Gly His Ala Leu Arg Ala Ile Gly Arg Leu
                180                 185                 190

Ser Ser Gly Gly Ser Gly Gly Ser Gly Gly Ser Gly Gly Ser Asp Gln
                195                 200                 205

Leu Thr Glu Glu Gln Ile Ala Glu Phe Lys Glu Ala Phe Ser Leu Phe
210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
                260                 265                 270

Phe Leu Thr Met Met Ala Arg Lys Met Lys Asp Thr Asp Ser Glu Glu
                275                 280                 285

Glu Ile Arg Glu Ala Phe Arg Val Phe Asp Lys Asp Gly Asn Gly Tyr
290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
                340                 345                 350

Lys Cys Val Phe Arg Thr Thr Tyr Lys Ala Lys Glu Lys Gly Val Lys
                355                 360                 365

Leu Pro Gly Val His Tyr Val Asp His Ile Ile Glu Ile Leu Ser His
                370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 47
<211> LENGTH: 1227
<212> TYPE: DNA
<213> ORGANISM: Artificial Sequence
<220> FEATURE:
<223> OTHER INFORMATION: Synthetic

<400> SEQUENCE: 47

```
atggtgagtg cgattaagcc agacatgaag atcaaactgc gtatggaagg caacgtaaac      60
gggcaccact ttgtgatcga cggagatggt acaggcaagc cttatgaggg aaaacagacc     120
atggatcttg aagtcaaaga gggcggacct ctgccttttg cctttgatat cctgaccact     180
gcattcctgt acggcaacag ggtattcgtg aaatatccag acaacataca agactatttt     240
aagcagtcgt ttcctaaggg gtattcgtgg aacgaagca tgactttcga agacgggggc      300
atttgctatg ccagaagcga cataacaatg aaggggaca ctttctataa taaagttcga      360
ttttatggta ccaactttcc cgccaatggt ccagttatgc agaagaagac gctgaaatgg     420
gagccctcca ctgagaaaat gtatgtgcgt gatggagtgc tgacgggtga tgtagagatg     480
gctttgttgc ttgaaggaaa tgcccattac cgagggctga tcagccgccg caagttcaac     540
aaaaccggcc atgccttgcg tgcaattggc cgcctgtcca gcggaggctc tggcggttcc     600
ggcggttcag gtggatcaga ccagctgacc gaggagcaaa ttgcagaatt aaggaggcg      660
ttctctttgt ttgacaaaga tggcgacggt acaattacaa ccaaggaatt gggcacagta     720
atgcgctccc ttggacagaa tcccactgaa gccgaacttc aagacatgat caatgaggtt     780
gatgctgacg gggatgggac tatcgacttt cctgagtttc ttaccatgat ggctcgcaaa     840
atgaaggata cagacagtga ggaggaaatt cgtgaggcct tcgtgtgtt tgataaggac      900
gggaacggtt atatctcagc ggcggagctg cgtcacgtta tgaccaactt aggcgaaaag     960
ctgactgatg aagaagtcga tgagatgatc cgcgaggcgg acatcgatgg tgatggtcaa    1020
gtcaattatg aagagtttgt ggtgatgatg accgcgaagt gcaacttcag aactacttac    1080
aaagctaagg agaagggtgt caagttacca ggcgtgcact atgtggacca catcattgag    1140
attttaagcc atgacaaaga ttacaacaag gttaagatct atgagtatgc tgttgctcat    1200
tctggattgc ctgacaatgc cagacga                                        1227
```

<210> SEQ ID NO 48
<211> LENGTH: 409
<212> TYPE: PRT
<213> ORGANISM: Artificial Sequence
<220> FEATURE:
<223> OTHER INFORMATION: Synthetic

<400> SEQUENCE: 48

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
```

130                 135                 140
Glu Lys Met Tyr Val Arg Asp Gly Val Leu Thr Gly Asp Val Glu Met
145                 150                 155                 160

Ala Leu Leu Leu Glu Gly Asn Ala His Tyr Arg Gly Leu Ile Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Gly Gly Ser Asp Gln
                195                 200                 205

Leu Thr Glu Glu Gln Ile Ala Glu Phe Lys Glu Ala Phe Ser Leu Phe
            210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
            260                 265                 270

Phe Leu Thr Met Met Ala Arg Lys Met Lys Asp Thr Asp Ser Glu Glu
            275                 280                 285

Glu Ile Arg Glu Ala Phe Arg Val Phe Asp Lys Asp Gly Asn Gly Tyr
            290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
            340                 345                 350

Lys Cys Asn Phe Arg Thr Thr Tyr Lys Ala Lys Glu Lys Gly Val Lys
            355                 360                 365

Leu Pro Gly Val His Tyr Val Asp His Ile Ile Glu Ile Leu Ser His
            370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405

<210> SEQ ID NO 49
<211> LENGTH: 1227
<212> TYPE: DNA
<213> ORGANISM: Artificial Sequence
<220> FEATURE:
<223> OTHER INFORMATION: Synthetic

<400> SEQUENCE: 49
atggtgagtg cgattaagcc agacatgaag atcaaactgc gtatggaagg caacgtaaac    60
gggcaccact tgtgatcga cggagatggt acaggcaagc ttatgaggg aaaacagacc    120 atggatcttg aagtcaaaga gggcggacct ctgcctttg cctttgatat cctgaccact    180
gcattcctgt acggcaacag ggtattcgtg aaatatccag acaacataca agactatttt    240
aagcagtcgt ttcctaaggg gtattcgtgg aacgaagca tgactttcga agacgggggc    300
atttgctatg ccagaagcga cataacaatg aaggggaca cttctataa taagttcga    360 ttttatggta ccaactttcc cgccaatggt ccagttatgc agaagaagac gctgaaatgg    420
gagccctcca ctgagaaaat gtatgtgcgt gatggagtgc tgacgggtga tgtagagatg    480

-continued

```
gctttgttgc ttgaaggaaa tgcccattac cgagggctga tcagccgccg caagttcaac      540
aaaaccggcc atgccttgcg tgcaattggc cgcctgtcca gcggaggctc tggcggttcc      600
ggcggttcag gtggatcaga ccagctgacc gaggagcaaa ttgcagaatt taaggaggcg      660
ttctctttgt ttgacaaaga tggcgacggt acaattacaa ccaaggaatt gggcacagta      720
atgcgctccc ttggacagaa tcccactgaa gccgaacttc aagacatgat caatgaggtt      780
gatgctgacg gggatgggac tatcgacttt cctgagtttc ttaccatgat ggctcgcaaa      840
atgaaggata cagacagtga ggaggaaatt cgtgaggcct tcgtgtgtt tgataaggac       900 gggaacggtt atatctcagc ggcggagctg cgtcacgtta tgaccaactt aggcgaaaag      960
ctgactgatg aagaagtcga tgagatgatc cgcgaggcgg acatcgatgg tgatggtcaa     1020
gtcaattatg aagagtttgt ggtgatgatg accgcgaagt gcaccttcag aactacttac     1080
aaagctaagg agaagggtgt caagttacca ggcgtgcact atgtggacca caccattgag     1140
attttaagcc atgacaaaga ttacaacaag gttaagatct atgagtatgc tgttgctcat     1200
tctggattgc ctgacaatgc cagacga                                         1227
```

<210> SEQ ID NO 50
<211> LENGTH: 409
<212> TYPE: PRT
<213> ORGANISM: Artificial Sequence
<220> FEATURE:
<223> OTHER INFORMATION: Synthetic

<400> SEQUENCE: 50

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Gly Leu Ile Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
```

Met Arg Ser Leu Gly Gln Asn Pro Thr Glu Ala Glu Leu Gln Asp Met
225                 230                 235                 240

Ile Asn Glu Val Asp Ala Asp Gly Asp Gly Thr Ile Asp Phe Pro Glu
        245                 250                 255

Phe Leu Thr Met Met Ala Arg Lys Met Lys Asp Thr Asp Ser Glu Glu
            260                 265                 270

Glu Ile Arg Glu Ala Phe Arg Val Phe Asp Lys Asp Gly Asn Gly Tyr
275                 280                 285

Ile Ser Ala Ala Glu Leu Arg His Val Met Thr Asn Leu Gly Glu Lys
        290                 295                 300

Leu Thr Asp Glu Glu Val Asp Glu Met Ile Arg Glu Ala Asp Ile Asp
305                 310                 315                 320

Gly Asp Gly Gln Val Asn Tyr Glu Glu Phe Val Met Met Thr Ala
            325                 330                 335

Lys Cys Thr Phe Arg Thr Thr Tyr Lys Ala Lys Glu Lys Gly Val Lys
        340                 345                 350

Leu Pro Gly Val His Tyr Val Asp His Thr Ile Glu Ile Leu Ser His
    355                 360                 365

Asp Lys Asp Tyr Asn Lys Val Lys Ile Tyr Glu Tyr Ala Val Ala His
370                 375                 380

Ser Gly Leu Pro Asp Asn Ala Arg Arg
385                 390                 395                 400

405

<210> SEQ ID NO 51
<211> LENGTH: 1227
<212> TYPE: DNA
<213> ORGANISM: Artificial Sequence
<220> FEATURE:
<223> OTHER INFORMATION: Synthetic

<400> SEQUENCE: 51
atggtgagtg cgattaagcc agacatgaag atcaaactgc gtatggaagg caacgtaaac      60
gggcaccact tgtgatcga cggagatggt acaggcaagc cttatgaggg aaaacagacc      120
atggatcttg aagtcaaaga gggcggacct ctgccttttg cctttgatat cctgaccact      180
gcattcctgt acggcaacag ggtattcgtg aaatatccag acaacataca agactatttt      240
aagcagtcgt ttcctaaggg gtattcgtgg aacgaagca tgactttcga gacgggggc      300 atttgctatg ccagaagcga cataacaatg gaagggggaca ctttctataa taagttcga      360 ttttatggta ccaactttcc cgccaatggt ccagttatgc agaagaagac gctgaaatgg      420
gagccctcca ctgagaaaat gtatgtgcgt gatggagtgc tgacgggtga gtagagatg      480 gctttgttgc ttgaaggaaa tgccgtttac ggagggctga tcagccgccg caagttcaac      540
aaaaccggcc atgccttgcg tgcaattggc cgcctgtcca gcggaggctc tggcggttcc      600
ggcggttcag gtggatcaga ccagctgacc gaggagcaaa ttgcagaatt taaggaggcg      660
ttctctttgt ttgacaaaga tggcgacggt acaattacaa ccaaggaatt gggcacagta      720
atgcgctccc ttggacagaa tcccactgaa gccgaacttc aagacatgat caatgaggtt      780
gatgctgacg gggatgggac tatcgactt cctgagtttc ttaccatgat ggctcgcaaa      840
atgaaggata cagacagtga ggaggaaatt cgtgaggcct tcgtgtgtt tgataaggac      900 gggaacggtt atatctcagc ggcggagctg cgtcacgtta tgaccaactt aggcgaaaag      960
ctgactgatg aagaagtcga tgagatgatc cgcgaggcgg acatcgatgg tgatggtcaa      1020

```
gtcaattatg aagagtttgt ggtgatgatg accgcgaagt gcctcttcag aactacttac    1080
aaagctaagg agaagggtgt caagttacca ggcgtgcact atgtggacca caccattgag    1140
attttaagcc atgacaaaga ttacaacaag gttaagatct atgagtatgc tgttgctcat    1200
tctggattgc ctgacaatgc cagacga                                        1227
```

<210> SEQ ID NO 52
<211> LENGTH: 409
<212> TYPE: PRT
<213> ORGANISM: Artificial Sequence
<220> FEATURE:
<223> OTHER INFORMATION: Synthetic

<400> SEQUENCE: 52

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
        35                  40                  45

Gly Pro Leu Pro Phe Ala Phe Asp Ile Leu Thr Thr Ala Phe Leu Tyr
    50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala Val Tyr Gly Gly Leu Ile Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
            260                 265                 270

Phe Leu Thr Met Met Ala Arg Lys Met Lys Asp Thr Asp Ser Glu Glu
        275                 280                 285

Glu Ile Arg Glu Ala Phe Arg Val Phe Asp Lys Asp Gly Asn Gly Tyr
    290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
```

```
                   325                 330                 335
Gly Asp Gly Gln Val Asn Tyr Glu Glu Phe Val Val Met Met Thr Ala
            340                 345                 350

Lys Cys Leu Phe Arg Thr Thr Tyr Lys Ala Lys Glu Lys Gly Val Lys
        355                 360                 365

Leu Pro Gly Val His Tyr Val Asp His Thr Ile Glu Ile Leu Ser His
    370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405
```

<210> SEQ ID NO 53
<211> LENGTH: 1227
<212> TYPE: DNA
<213> ORGANISM: Artificial Sequence
<220> FEATURE:
<223> OTHER INFORMATION: Synthetic

<400> SEQUENCE: 53

| | | | | |
|---|---|---|---|---|
| atggtgagtg cgattaagcc agacatgaag atcaaactgc gtatggaagg caacgtaaac | 60 |
| gggcaccact ttgtgatcga cggagatggt acaggcaagc cttatgaggg aaaacagacc | 120 |
| atggatcttg aagtcaaaga gggcggacct ctgccttttg cctttgatat cctgaccact | 180 |
| gcattcctgt acggcaacag ggtattcgtg aaatatccag acaacataca agactatttt | 240 |
| aagcagtcgt ttcctaaggg gtattcgtgg aacgaagca tgactttcga agacgggggc | 300 |
| atttgctatg ccagaagcga cataacaatg aaggggaca ctttctataa taaagttcga | 360 |
| ttttatggta ccaactttcc cgccaatggt ccagttatgc agaagaagac gctgaaatgg | 420 |
| gagccctcca ctgagaaaat gtatgtgcgt gatggagtgc tgacgggtga tgtagagatg | 480 |
| gctttgttgc ttgaaggaaa tgccgtttac ggagggggga gcagccgccg caagttcaac | 540 |
| aaaaccggcc atgccttgcg tgcaattggc cgcctgtcca gcggaggctc tggcggttcc | 600 |
| ggcggttcag gtggatcaga ccagctgacc gaggagcaaa ttgcagaatt taaggaggcg | 660 |
| ttctctttgt tgacaaaga tggcgacggt acaattacaa ccaaggaatt gggcacagta | 720 |
| atgcgctccc ttggacagaa tcccactgaa gccgaacttc aagacatgat caatgaggtt | 780 |
| gatgctgacg gggatgggac tatcgacttt cctgagtttc ttaccatgat ggctcgcaaa | 840 |
| atgaaggata cagacagtga ggaggaaatt cgtgaggcct tcgtgtgtt tgataaggac | 900 |
| gggaacggtt atatctcagc ggcggagctg cgtcacgtta tgaccaactt aggcgaaaag | 960 |
| ctgactgatg aagaagtcga tgagatgatc cgcgaggcgg acatcgatgg tgatggtcaa | 1020 |
| gtcaattatg aagagtttgt ggtgatgatg accgcgaagt gcctcttcag aactacttac | 1080 |
| aaagctaagg agaagggtgt caagttacca ggcgtgcact atgtggacca tcattgag | 1140 |
| attttaagcc atgacaaaga ttacaacaag gttaagatct atgagtatgc tgttgctcat | 1200 |
| tctggattgc ctgacaatgc cagacga | 1227 |

<210> SEQ ID NO 54
<211> LENGTH: 409
<212> TYPE: PRT
<213> ORGANISM: Artificial Sequence
<220> FEATURE:
<223> OTHER INFORMATION: Synthetic

<400> SEQUENCE: 54

-continued

```
Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
            20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
            85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Glu Pro Ser Thr
            130                 135                 140

Glu Lys Met Tyr Val Arg Asp Gly Val Leu Thr Gly Asp Val Glu Met
145                 150                 155                 160

Ala Leu Leu Leu Glu Gly Asn Ala Val Tyr Gly Gly Ser Ser Arg
                165                 170                 175

Arg Lys Phe Asn Lys Thr Gly His Ala Leu Arg Ala Ile Gly Arg Leu
                180                 185                 190

Ser Ser Gly Gly Ser Gly Gly Ser Gly Gly Ser Asp Gln
            195                 200                 205

Leu Thr Glu Glu Gln Ile Ala Glu Phe Lys Glu Ala Phe Ser Leu Phe
    210                 215                 220

Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
                260                 265                 270

Phe Leu Thr Met Met Ala Arg Lys Met Lys Asp Thr Asp Ser Glu Glu
            275                 280                 285

Glu Ile Arg Glu Ala Phe Arg Val Phe Asp Lys Asp Gly Asn Gly Tyr
    290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
            340                 345                 350

Lys Cys Leu Phe Arg Thr Thr Tyr Lys Ala Lys Glu Lys Gly Val Lys
            355                 360                 365

Leu Pro Gly Val His Tyr Val Asp His Ile Ile Glu Ile Leu Ser His
    370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
            405
```

<210> SEQ ID NO 55
<211> LENGTH: 1096
<212> TYPE: DNA
<213> ORGANISM: Artificial Sequence
<220> FEATURE:
<223> OTHER INFORMATION: Synthetic

<400> SEQUENCE: 55

```
agtcaaagag ggcggacctc tgccttttgc ctttgatatc ctgaccactg cattcctgta      60
cggcaacagg gtattcgtga aatatccaga caacatacaa gactatttta agcagtcgtt     120
tcctaagggg tattcgtggg aacgaagcat gactttcgaa gacggggggca tttgctatgc    180
cagaagcgac ataacaatgg aaggggacac tttctataat aaagttcgat tttatggtac    240
caactttccc gccaatggtc agttatgca aagaagacg ctgaaatggc agccctccac      300
tgagaaaatg tatgtgcgtg atggagtgct gacgggtgat gtagagatgg ctttgttgct    360
tgaaggaaat gcccattacc gaggggggag cagccgccgc aagttcaaca aaaccggcca    420
tgccttgcgt gcaattggcc gcctgtccag cggaggctct ggcggttccg gcggttcagg    480
tggatcagac cagctgaccg aggagcaaat tgcagaattt aaggaggcgt tctctttgtt    540
tgacaaagat ggcgacggta caattacaac caaggaattg gcacagtaa tgcgctccct    600
tggacagaat cccactgaag ccgaacttca agacatgatc aatgaggttg atgctgacgg    660
ggatgggact atcgactttc tgagttttct taccatgatg gctcgcaaaa tgaaggatac    720
agacagtgag gaggaaattc gtgaggcctt tcgtgtgttt gataaggacg ggaacggtta    780
tatctcagcg gcggagctgc gtcacgttat gaccaactta ggcgaaaagc tgactgatga    840
agaagtcgat gagatgatcc gcgaggcgga catcgatggt gatggtcaag tcaattatga    900
agagtttgtg gtgatgatga ccgcgaagtg caccttcaga actacttaca agctaagga    960
gaagggtgtc aagttaccag gcgtgcacta tgtggaccac accattgaga tttaagcca    1020
tgacaaagat tacaacaagg ttaagatcta tgagtatgct gttgctcatt ctggattgcc    1080
tgacaatgcc agacga                                                    1096
```

<210> SEQ ID NO 56
<211> LENGTH: 409
<212> TYPE: PRT
<213> ORGANISM: Artificial Sequence
<220> FEATURE:
<223> OTHER INFORMATION: Synthetic

<400> SEQUENCE: 56

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala

|  |  |  | 115 |  |  |  | 120 |  |  |  | 125 |  |
|---|---|---|---|---|---|---|---|---|---|---|---|---|

Asn Gly Pro Val Met Gln Lys Lys Thr Leu Lys Trp Gln Pro Ser Thr
        130                135              140

Glu Lys Met Tyr Val Arg Asp Gly Val Leu Thr Gly Asp Val Glu Met
145               150              155              160

Ala Leu Leu Leu Glu Gly Asn Ala His Tyr Arg Gly Gly Ser Ser Arg
               165              170              175

Arg Lys Phe Asn Lys Thr Gly His Ala Leu Arg Ala Ile Gly Arg Leu
        180                185              190

Ser Ser Gly Gly Ser Gly Gly Ser Gly Gly Ser Asp Gln
            195                200              205

Leu Thr Glu Glu Gln Ile Ala Glu Phe Lys Glu Ala Phe Ser Leu Phe
        210                215              220

Asp Lys Asp Gly Asp Gly Thr Ile Thr Thr Lys Glu Leu Gly Thr Val
225               230              235              240

Met Arg Ser Leu Gly Gln Asn Pro Thr Glu Ala Glu Leu Gln Asp Met
               245              250              255

Ile Asn Glu Val Asp Ala Asp Gly Asp Gly Thr Ile Asp Phe Pro Glu
        260                265              270

Phe Leu Thr Met Met Ala Arg Lys Met Lys Asp Thr Asp Ser Glu Glu
            275                280              285

Glu Ile Arg Glu Ala Phe Arg Val Phe Asp Lys Asp Gly Asn Gly Tyr
        290                295              300

Ile Ser Ala Ala Glu Leu Arg His Val Met Thr Asn Leu Gly Glu Lys
305               310              315              320

Leu Thr Asp Glu Glu Val Asp Glu Met Ile Arg Glu Ala Asp Ile Asp
            325                330              335

Gly Asp Gly Gln Val Asn Tyr Glu Glu Phe Val Val Met Met Thr Ala
               340              345              350

Lys Cys Thr Phe Arg Thr Thr Tyr Lys Ala Lys Glu Lys Gly Val Lys
            355                360              365

Leu Pro Gly Val His Tyr Val Asp His Thr Ile Glu Ile Leu Ser His
        370                375              380

Asp Lys Asp Tyr Asn Lys Val Lys Ile Tyr Glu Tyr Ala Val Ala His
385               390              395              400

Ser Gly Leu Pro Asp Asn Ala Arg Arg
               405

```
<210> SEQ ID NO 57
<211> LENGTH: 1227
<212> TYPE: DNA
<213> ORGANISM: Artificial Sequence
<220> FEATURE:
<223> OTHER INFORMATION: Synthetic

<400> SEQUENCE: 57
atggtgagtg cgattaagcc agacatgaag atcaaactgc gtatggaagg caacgtaaac      60
gggcaccact tgtgatcga cggagatggt acaggcaagc ttatgaggg aaaacagacc      120 atggatcttg aagtcaaaga gggcggacct ctgcctttttg cctttgatat cctgaccact      180
gcattcctgt acggcaacag ggtattcgtg aaatatccag acaacataca agactatttt      240
aagcagtcgt ttcctaaggg gtattcgtgg gaacgaagca tgactttcga agacgggggc      300
atttgctatg ccagaagcga cataacaatg gaaggggaca cttctctataa taaagttcga      360 ttttatggta ccaactttcc cgccaatggt ccagttatgc agaagaagac gctgaaatgg      420
```

```
gagccctcca ctgagaaaat gtatgtgcgt gatggagtgc tgacgggtga tgtagagatg    480
gctttgttgc ttgaaggaaa tgcccattac cgagggggga tcagccgccg caagttcaac    540
aaaaccggcc atgccttgcg tgcaattggc cgcctgtcca gcggaggctc tggcggttcc    600
ggcggttcag gtggatcaga ccagctgacc gaggagcaaa ttgcagaatt taaggaggcg    660
ttctctttgt ttgacaaaga tggcgacggt acaattacaa ccaaggaatt gggcacagta    720
atgcgctccc ttggacagaa tcccactgaa gccgaacttc aagacatgat caatgaggtt    780
gatgctgacg gggatgggac tatcgacttt cctgagtttc ttaccatgat ggctcgcaaa    840
atgaaggata cagacagtga ggaggaaatt cgtgaggcct ttcgtgtgtt tgataaggac    900
gggaacggtt atatctcagc ggcggagctg cgtcacgtta tgaccaactt aggcgaaaag    960
ctgactgatg aagaagtcga tgagatgatc cgcgaggcgg acatcgatgg tgatggtcaa   1020
gtcaattatg aagagtttgt ggtgatgatg accgcgaagt gcctcttcag aactacttac   1080
aaagctaagg agaagggtgt caagttacca ggcgtgcact atgtggacca caccattgag   1140
attttaagcc atgacaaaga ttacaacaag gttaagatct atgagtatgc tgttgctcat   1200
tctggattgc tgacaatgc cagacga                                        1227

<210> SEQ ID NO 58
<211> LENGTH: 409
<212> TYPE: PRT
<213> ORGANISM: Artificial Sequence
<220> FEATURE:
<223> OTHER INFORMATION: Synthetic

<400> SEQUENCE: 58

Met Val Ser Ala Ile Lys Pro Asp Met Lys Ile Lys Leu Arg Met Glu
1               5                   10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe Leu Tyr
        50                  55                  60

Gly Asn Arg Val Phe Val Lys Tyr Pro Asp Asn Ile Gln Asp Tyr Phe
65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Ser Asp Ile Thr Met Glu Gly
            100                 105                 110

Asp Thr Phe Tyr Asn Lys Val Arg Phe Tyr Gly Thr Asn Phe Pro Ala
        115                 120                 125

Asn Gly Pro Val Met Gln Lys Thr Leu Lys Trp Glu Pro Ser Thr
    130                 135                 140

Glu Lys Met Tyr Val Arg Asp Gly Val Leu Thr Gly Asp Val Glu Met
145                 150                 155                 160

Ala Leu Leu Leu Glu Gly Asn Ala His Tyr Arg Gly Ile Ser Arg
                165                 170                 175

Arg Lys Phe Asn Lys Thr Gly His Ala Leu Arg Ala Ile Gly Arg Leu
            180                 185                 190

Ser Ser Gly Gly Ser Gly Gly Ser Gly Gly Ser Asp Gln
        195                 200                 205

Leu Thr Glu Glu Gln Ile Ala Glu Phe Lys Glu Ala Phe Ser Leu Phe
```

-continued

```
             210                 215                    220
Asp Lys Asp Gly Asp Gly Thr Ile Thr Thr Lys Glu Leu Gly Thr Val
225                 230                 235                 240

Met Arg Ser Leu Gly Gln Asn Pro Thr Glu Ala Glu Leu Gln Asp Met
                245                 250                 255

Ile Asn Glu Val Asp Ala Asp Gly Asp Gly Thr Ile Asp Phe Pro Glu
                260                 265                 270

Phe Leu Thr Met Met Ala Arg Lys Met Lys Asp Thr Asp Ser Glu Glu
            275                 280                 285

Glu Ile Arg Glu Ala Phe Arg Val Phe Asp Lys Asp Gly Asn Gly Tyr
        290                 295                 300

Ile Ser Ala Ala Glu Leu Arg His Val Met Thr Asn Leu Gly Glu Lys
305                 310                 315                 320

Leu Thr Asp Glu Glu Val Asp Glu Met Ile Arg Glu Ala Asp Ile Asp
                325                 330                 335

Gly Asp Gly Gln Val Asn Tyr Glu Glu Phe Val Val Met Met Thr Ala
                340                 345                 350

Lys Cys Leu Phe Arg Thr Thr Tyr Lys Ala Lys Glu Lys Gly Val Lys
            355                 360                 365

Leu Pro Gly Val His Tyr Val Asp His Thr Ile Glu Ile Leu Ser His
        370                 375                 380

Asp Lys Asp Tyr Asn Lys Val Lys Ile Tyr Glu Tyr Ala Val Ala His
385                 390                 395                 400

Ser Gly Leu Pro Asp Asn Ala Arg Arg
                405
```